US008686003B2

(12) United States Patent
Millan et al.

(10) Patent No.: US 8,686,003 B2
(45) Date of Patent: Apr. 1, 2014

(54) TISSUE NON-SPECIFIC ALKALINE PHOSPHATASE INHIBITORS AND USES THEREOF FOR TREATING VASCULAR CALCIFICATION

(75) Inventors: Jose Luis Millan, La Jolla, CA (US); Eduard Sergienko, La Jolla, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 0 days.

(21) Appl. No.: 13/313,756

(22) Filed: Dec. 7, 2011

(65) Prior Publication Data

US 2012/0095044 A1     Apr. 19, 2012

Related U.S. Application Data

(63) Continuation of application No. 12/117,570, filed on May 8, 2008, now Pat. No. 8,119,693.

(60) Provisional application No. 60/928,400, filed on May 8, 2007.

(51) Int. Cl.
*A61K 31/47* (2006.01)
*A61K 31/44* (2006.01)

(52) U.S. Cl.
USPC ............................................ 514/313; 514/352

(58) Field of Classification Search
None
See application file for complete search history.

(56) References Cited

U.S. PATENT DOCUMENTS

| | | | |
|---|---|---|---|
| 5,602,136 | A | 2/1997 | Ruhter |
| 6,598,772 | B1 | 7/2003 | Wilfer |
| 2004/0152739 | A1 | 8/2004 | Hanau |
| 2004/0197335 | A1 | 10/2004 | Slavin |
| 2006/0004043 | A1 | 1/2006 | Bhagwat |
| 2006/0056980 | A1 | 3/2006 | Yoo |
| 2006/0258723 | A1 | 11/2006 | Hamanaka |

FOREIGN PATENT DOCUMENTS

| | | |
|---|---|---|
| WO | 02092020 | 11/2002 |
| WO | 03057225 | 7/2003 |
| WO | 2006039480 | 4/2006 |

OTHER PUBLICATIONS

Schoppet M, Shanahan CM. Role for alkaline phosphatase as an inducer of vascular calcification in renal failure? Kidney Int. May 2008;73(9):989-91.*
Sergienko E, Su Y, Chan X, Brown B, Hurder A, Narisawa S, Milián JL. Identification and characterization of novel tissue-nonspecific alkaline phosphatase inhibitors with diverse modes of action. J Biomol Screen. Aug. 2009;14(7):824-37. Epub Jun. 25, 2009.*
Dahl, et al., "Discovery and validation of a series of Aryl Sulfonamides as selective inhibitors of tissue-nonspecific alkaline phosphatase (TNAP)", J Medical Chemistry, 52:6919-25 (2009).
Di Mauro,et al., "Kinetic characterization of hypophosphatasia mutations with physiological substrates", J. Bone & Min. Res. 17: 1383-1391 (2002).
Harmey, et al., "Concerted regulation of inorganic pyrophosphate and osteopontin by Akp2, Enppl and Ank. An integrated model of the pathogenesis of mineralization disorders", Am J Pathol 164: 1199-1209 (2004).
Harmey, et al., Elevated osteopontin levels contribute to the hypophosphatasia phenotype in Akp2–/– mice. J Bone Min Res 21: 1377-1386 (2006).
Hessle, et al., "Tissue-nonspecific alkaline phosphatase and plasma cell membrane glycoprotein-1 are central antagonistic regulators of bone mineralization", Proc Natl Aced Sci USA 99:9445-9449 (2002).
Hilaire, et al, "NTSE mutations and arterial calcifications", N Engl J Med, 364:432-42 (2011).
Hoylaerts, et al., "Mammalian alkaline phosphatase catalysis requires active site structure stabilization via the N-terminal amino acid microenvironment", Biochemistry 45:9756-9766 (2006).
Hoylaerts, et al., "Molecular mechanism of uncompetitive inhibition of human placental and germ cell alkaline phosphatase", Biochem J 286:23-30 (1992).
Johnson, et al., "Tissue-nonspecific alkaline phosphatase (TNAP) and plasma cell membrane glycaproteln-1 (PC-1) act as selective and mutual antagonists of mineralizing activity by murine osteoblasts", Am J Phys Regulatory and integrative Physiology 279: R1365-1377 (2000).
Kozlenkov, et al., "Residues determining the binding specificity of uncompetitive inhibitors to tissue-nonspecific alkaline phosphatase", J Bone Min Res 19:1862-1872 (2004).
Lomashvili, et al., "Phosphate-induced vascular calcification: role of pyrophosphate and osteopontin", J Am. Soc. Nephrol. 15: 1392-1401 (2004).
Lomashvili, et al., "Upreulation of alkaline phosphatase and pyrophosphate hydrolysis: Potential mechanism for uremic vascular calcification", Intl. Soc Nephrology, 73(9):1024-30 (2008).
Murshed, et al., "Unique coexpression in osteoblasts of broadly expressed genes accounts for the spatial restriction of ECM mineralization to bone", Genes & Dev. 19:1093-1104 (2005).
Narisawa, et al., "Novel inhibitors of alkaline phosphatase suppress vascular smooth muscle cell calcification", J Bone Miner Res., 22:1700-10 (2007).
O\Neill and Lomashvili, "Recent progress in the treatment of vascular calcification", Kidney Intl 78:1232-39 (2010).
O\Neill, et al., "Treatment with pyrophosphate inhibits uremic vascular calcification", Kidney Intl., 79:512-517 (2011).
Schoppet and Shanahan, "Role for alkaline phosphatase as an inducer of cascular calcification in renal failure" , Kidney Intl., 73:989-991 (2008).
Speer, et al., Inactivation of the osteopontin gene enhances vascular calcification of matrix Gla protein-deficient mice: evidence for osteopontin as an inducible inhibitor of vascular calcification in vivo. J Exp Med 196:1047-1055 (2002).

(Continued)

*Primary Examiner* — Paul Zarek
(74) *Attorney, Agent, or Firm* — Pabst Patent Group LLP

(57) ABSTRACT

Disclosed herein are compounds that are tissue-nonspecific alkaline phosphatase inhibitors. The disclosed compounds are used to treat, prevent, or abate vascular calcification, arterial calcification and other cardiovascular diseases.

14 Claims, 11 Drawing Sheets

(56) References Cited

OTHER PUBLICATIONS

Steitz, et al., "Osteopontin inhibits mineral deposition and promotes regression of ectopic calcification", Am J Pathol 161:2035-2046 (2002).

Wennberg, et al., "Functional characterization of osteoblasts and osteoclasts from alkaline phosphatase knockout mice", J Bone Min Res 15:1879-1888 (2000).

Mathieu, et al., "Calcification of human valve interstitial cells is dependent on alkaline phosphatase activity", J Heart Valve Disease, 14(3):353-7 (2005).

Paget, et al., "Inhibition of serum phosphatse activity by sulfanilamide and sulfapyridine", Comptes rendus des séances de la societe de biologie et de ses filiales, 138:415-16 coden (1944) Abstract only.

European Search Report EP 11 19 1931 mailed Feb. 10, 2012.

International Search Report for corresponding PCT Application PCT/US2008/63106, mailed Jan. 12, 2009.

* cited by examiner

TISSUE NON-SPECIFIC ALKALINE PHOSPHATASE INHIBITORS AND USES THEREOF FOR TREATING VASCULAR CALCIFICATION

CROSS-REFERENCE TO RELATED APPLICATIONS

This application is a continuation of U.S. application Ser. No. 12/117,570, filed May 8, 2008, which claims the benefit of U.S. Provisional Application No. 60/928,400 filed May 8, 2007. application Ser. No. 12/117,570, filed May 8, 2008, and Provisional Application No. 60/928,400, filed May 8, 2007, are incorporated herein by reference in their entirety.

STATEMENT REGARDING FEDERALLY SPONSORED RESEARCH

Research leading to this invention was funded in part by the National Institutes of Health, grant no. NIH-DE12889. The U.S. Government has certain rights in this invention.

FIELD

Disclosed herein are compounds that are tissue-nonspecific alkaline phosphatase inhibitors. The disclosed compounds are used to treat, prevent, or abate vascular calcification, arterial calcification and other cardiovascular diseases.

BACKGROUND

Vascular calcification occurs when hydroxyapatite (HA) is deposited in cardiovascular tissues such as arteries and heart valves. HA can be a significant risk factor in the pathogenesis of cardiovascular disease and has been associated with myocardial infarction and coronary death (Detrano R C, Doherty T M, Davies M J, Stary H C 2000 "Predicting coronary events with coronary calcium: pathophysiologic and clinical problems." Curr Probl Cardiol 25:374-402). The mechanisms of pathological vascular calcification are believed to be similar to normal embryonic bone formation (Doherty T M, Uzui H, Fitzpatrick L A, Tripathi P V, Dunstan C R, Asotra K, Rajavashisth T B 2002 "Rationale for the role of osteoclast-like cells in arterial calcification." Faseb J 16:577-582). Studies have demonstrated an association between low bone mass and an increased risk of cardiovascular disease (von der Recke P, Hansen M A, Hassager C 1999 "The association between low bone mass at the menopause and cardiovascular mortality." Am J Med 106:273-278).

The link between cardiovascular disease and bone formation has been verified in vivo. Matrix Gla Protein (MGP)-deficient mice (Mgp–/–), for example, display an osteopenic bone phenotype with arterial calcification (Speer M Y, McKee M D, Guldberg R E, Liaw L, Yang H Y, Tung E, Karsenty G, Giachelli C M 2002 "Inactivation of the osteopontin gene enhances vascular calcification of matrix Gla protein-deficient mice: evidence for osteopontin as an inducible inhibitor of vascular calcification in vivo." J Exp Med 196:1047-1055). Mutations affecting the osteoclastic lineage, such as in osteoprotegerin (OPG) knockout mice, which have an osteoporotic phenotype, are also associated with arterial calcification (Bucay N, Sarosi I, Dunstan C R, Morony S, Tarpley J, Capparelli C, Scully S, Tan H L, Xu W, Lacey D L, Boyle W J, Simonet W S 1998 osteoprotegerin-deficient mice develop early onset osteoporosis and arterial calcification. Genes Dev 12:1260-1268). In addition, osteopontin (OPN), a mineralization inhibitor, is known to have dual roles in bone and heart (Steitz S A, Speer M Y, McKee M D, Liaw L, Almeida M, Yang H, Giachelli C M 2002 "Osteopontin inhibits mineral deposition and promotes regression of ectopic calcification." Am J Pathol 161:2035-2046). OPN is expressed in osteoblasts as well as in activated inflammatory cells in injured arteries and appears to play a protective role against arterial calcification, as OPN null mice are compromised when responding to cardiovascular challenge (Myers D L, Harmon K J, Lindner V, Liaw L 2003 Alterations of arterial physiology in osteopontin-null mice. Arterioscler Thromb Vasc Biol 23:1021-1028).

These observations support the contention that bone mineralization and arterial calcification share similar underlying pathologies. Furthermore, mice lacking NPP1 (Enpp1–/–), a major generator of the calcification inhibitor inorganic pyrophosphate (PPi), spontaneously develop articular cartilage, perispinal and aortic calcification at a young age (Okawa A, Nakamura I, Goto S, Moriya H, Nakamura Y, Ikegawa S 1998 "Mutation in Npps in a mouse model of ossification of the posterior longitudinal ligament of the spine." Nat Genet. 19:271-273). These mice share similar phenotypic features with a human disease, idiopathic infantile arterial calcification (IIAC) (Rutsch F, Vaingankar S, Johnson K, Goldfine I, Maddux B, Schauerte P, Kalhoff H, Sano K, Boisvert W A, Superti-Furga A, Terkeltaub R 2001 PC-1 nucleoside triphosphate pyrophosphohydrolase deficiency in idiopathic infantile arterial calcification." Am J Pathol 158:543-554; Rutsch F, Ruf N, Vaingankar S, Toliat M R, Suk A, Hohne W, Schauer G, Lehmann M, Roscioli T, Schnabel D, Epplen J T, Knisely A, Superti-Furga A, McGill J, Filippone M, Sinaiko A R, Vallance H, Hinrichs B, Smith W, Ferre M, Terkeltaub R, Nurnberg P 2003 "Mutations in ENPP1 are associated with 'idiopathic' infantile arterial calcification." Nat Genet. 34:379-381). Moreover, in another mouse model with depressed extracellular PPi (ePPi) levels, due to defective transport function of the transmembrane protein ANK (ank/ank mutant mice), soft tissue ossification is found, similarly to that in Enpp1–/– mice (Ho A M, Johnson M D, Kingsley D M 2000 "Role of the mouse ank gene in control of tissue calcification and arthritis." Science 289:265-270-13; Harmey D, Hessle L, Narisawa S, Johnson K, Terkeltaub R, Milián J L 2004 "Concerted regulation of inorganic pyrophosphate and osteopontin by Akp2, Enpp1 and Ank. An integrated model of the pathogenesis of mineralization disorders." Am J Pathol 164: 1199-1209; Johnson K, Polewski M, van Etten D, Terkeltaub R 2005 "Chondrogenesis mediated by PPi depletion promotes spontaneous aortic calcification in NPP1–/– mice." Arterioscler Thromb Vasc Biol 25:686-691).

Alkaline phosphatases (E.C.3.1.3.1) (APs) are dimeric enzymes present in most organisms (Milián J L 2006 "Mammalian alkaline phosphatases. From biology to applications in medicine and biotechnology." Wiley-VCH Verlag GmbH & Co, Weinheim, Germany pp. 1-322). They catalyze the hydrolysis of phosphomonoesters with release of inorganic phosphate (Pi) and alcohol. In humans, three of the four isozymes are tissue-specific, i.e., the intestinal (IAP), placental (PLAP), and germ cell (GCAP) APs, while the fourth AP is tissue-nonspecific (TNAP) and is expressed in bone, liver and kidney.

Recent studies have provided compelling evidence that a major role for TNAP in bone tissue is to hydrolyze ePPi to avoid accumulation of this mineralization inhibitor, thus ensuring normal bone mineralization (Johnson K A, Hessle L, Wennberg C, Mauro S, Narisawa S, Goding J, Sano K, Milián J L, Terkeltaub R 2000 "Tissue-nonspecific alkaline phosphatase (TNAP) and plasma cell membrane glycoprotein-1 (PC-1) act as selective and mutual antagonists of mineralizing activity by murine osteoblasts." Am J Phys Regulatory and Integrative Physiology 279: R1365-1377-17; Hessle L, Johnson K A, Anderson H C, Narisawa S, Sali A, Goding J W, Terkeltaub R, Milián J L 2002 "Tissue-nonspecific alkaline phosphatase and plasma cell membrane glycoprotein-1 are central antagonistic regulators of bone mineralization." Proc Natl Acad Sci USA 99:9445-9449; Johnson K, Goding J, Van Etten D, Sali A, Hu S I, Farley D, Krug H, Hessle L, Milián J L, Terkeltaub R 2003 "Linked deficiencies in extracellular PP(i) and osteopontin mediate pathologic calcification associated with defective PC-1 and ANK expression." J Bone Min Res 18:994-1004). Normalization of ePPi levels in NPP1 null and ANK-deficient mice improves their soft-tissue ossification abnormalities (Johnson K A, Hessle L, Wennberg C, Mauro S, Narisawa S, Goding J, Sano K, Milián J L, Terkeltaub R 2000 "Tissue-nonspecific alkaline phosphatase (TNAP) and plasma cell membrane glycoprotein-1 (PC-1) act as selective and mutual antagonists of mineralizing activity by murine osteoblasts." Am J Phys Regulatory and Integrative Physiology 279: R1365-1377, 16; Hessle L, Johnson K A, Anderson H C, Narisawa S, Sali A, Goding J W, Terkeltaub R, Milián J L 2002 "Tissue-nonspecific alkaline phosphatase and plasma cell membrane glycoprotein-1 are central antagonistic regulators of bone mineralization." Proc Natl Acad Sci USA 99:9445-9449). Crossbreeding either the Enpp1-/- or the ank/ank mice to mice deficient in TNAP (Akp2-/-) mice normalizes ePPi levels and induces a secondary up-regulation of OPN levels (Johnson K, Goding J, Van Etten D, Sali A, Hu S I, Farley D, Krug H, Hessle L, Milián J L, Terkeltaub R 2003 "Linked deficiencies in extracellular PP(i) and osteopontin mediate pathologic calcification associated with defective PC-1 and ANK expression." J Bone Min Res 18:994-1004).

Importantly, these studies have indicated that TNAP may be a useful therapeutic target for the treatment of diseases such as ankylosis and osteoarthritis, but also arterial calcification. Indeed, substantial evidence points to the presence of TNAP-rich vesicles at sites of mineralization in human arteries. The presence of TNAP-enriched matrix vesicles (MVs) in human atherosclerotic lesions suggests an active role in the promotion of the accompanying vascular calcification (Hsu H H, Camacho N P 1999 "Isolation of calcifiable versicles from human atherosclerotic aortas." Atherosclerosis 143:353-362; Hui M, Li S Q, Holmyard D, Cheng P 1997 "Stable transfection of nonosteogenic cell lines with tissue nonspecific alkaline phosphatase enhances mineral deposition both in the presence and absence of beta-glycerophosphate: possible role for alkaline phosphatase in pathological mineralization." Calcified Tissue International 60:467-72; Hui M, Tenenbaum H C 1998 "New face of an old enzyme: alkaline phosphatase may contribute to human tissue aging by inducing tissue hardening and calcification." Anatomical Record 253:91-94. Tanimura A, McGregor D H, Anderson H C 1986 "Calcification in atherosclerosis. I. Human studies." J Exp Pathol 2:261-273. Tanimura A, McGregor D H, Anderson H C 1986 "Calcification in atherosclerosis. II. Animal studies." J Exp Pathol 2:275-297). Increased expression of TNAP accelerates calcification by bovine vascular smooth muscle cells (VSMCs) (Shioi A, Nishizawa Y, Jono S, Koyama H, Hosoi M, Morii H 1995 Beta-glycerophosphate accelerates calcification in cultured bovine vascular smooth muscle cells. Arterioscler Thromb Vasc Biol 15:2003-2009) and macrophages may induce a calcifying phenotype in human VSMCs by activating TNAP in the presence of IFNγ and 1,25 (OH)$_2$D$_3$ (Shioi A, Katagi M, Okuno Y, Mori K, Jono S, Koyama H, Nishizawa Y 2002 "Induction of bone-type alkaline phosphatase in human vascular smooth muscle cells: roles of tumor necrosis factor-alpha and oncostatin M derived from macrophages." Circ Res 91:9-16). Calcification of rat aorta in culture and of human valve interstitial cells has been shown to be dependent on TNAP activity (Lomashvili K, Cobbs S, Hennigar R, Hardcastle K, O'Neill W C 2004 "Phosphate-induced vascular calcification: role of pyrophosphate and osteopontin." J. Am. Soc. Nephrol. 15: 1392-1401; Mathieu P, Voisine P, Pepin A, Shetty R, Savard N, Dagenais F 2005 "Calcification of human valve interstitial cells is dependent on alkaline phosphatase activity." J Heart Valve Disease 14:353-357).

BRIEF SUMMARY

In accordance with the purpose of this invention, as embodied and broadly described herein, this invention relates tissue-nonspecific alkaline phosphatase inhibitors and uses thereof to treat, prevent, or abate vascular calcification, arterial calcification or other cardiovascular diseases Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION

Figure 1A:
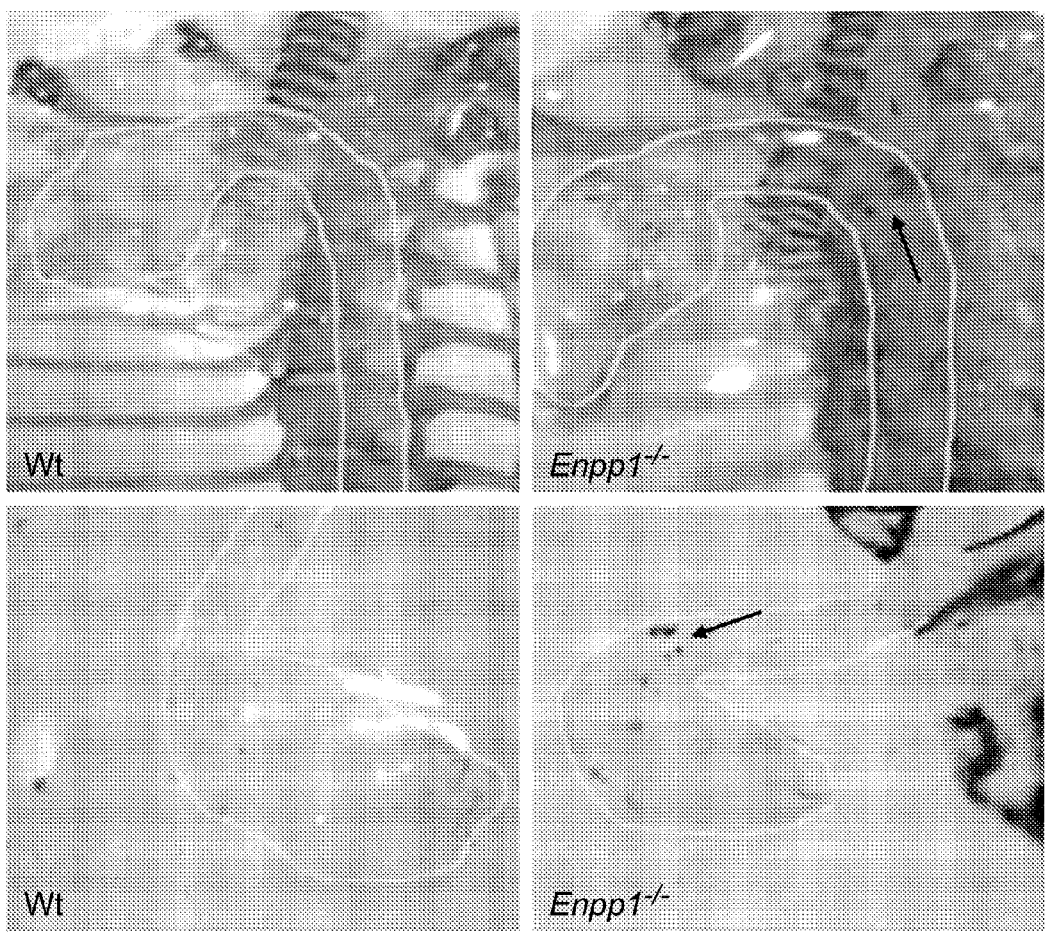
FIG. 1A shows whole mount preparations of the heart and aorta of Enpp1$^{-/-}$ mice reveal multiple foci of aortic calcification. The preparations from control mice (Wt) do not show signs of aortic calcification.

The disclosed method and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a compound is disclosed and discussed and a number of modifications that can be made to a number of molecules including the compound are discussed, each and every combination and permutation of compound and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

A. Compositions

1. TNAP Inhibitors

Disclosed herein are compounds that can inhibit tissue-nonspecific alkaline phosphatases (TNAPs). These compounds can be used to treat or prevent vascular calcification, arterial calcification and cardiovascular diseases in a patient having such conditions or diseases or at risk for such conditions or diseases.

The disclosed compounds can comprise:

A) rings containing two or more nitrogen atoms;

B) aryl sulfonamides; and

C) compounds that inhibit tissue-nonspecific alkaline phosphatases having an IC$_{50}$ of less than or equal to 20 µM wherein the compounds comprise one or more aryl phosphonate or phosphonic acid units.

The disclosed compounds include the following compounds having 2 or 3 nitrogen atoms in a heteroaryl ring:

i) pyrazoles having the formula:

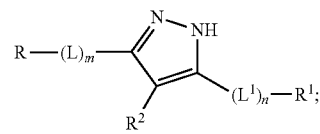

ii) fused rings comprising a pyrazole ring having the formula:

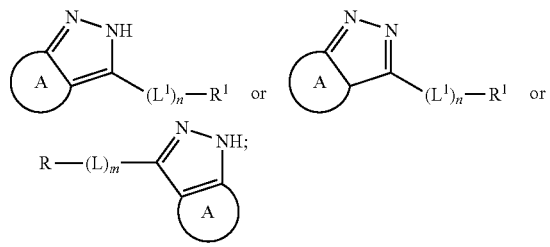

iii) [1,2,4]triazoles having the formula:

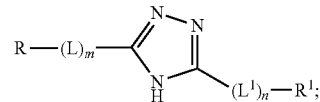

iv) fused rings comprising a [1,2,4]triazole ring having the formula:

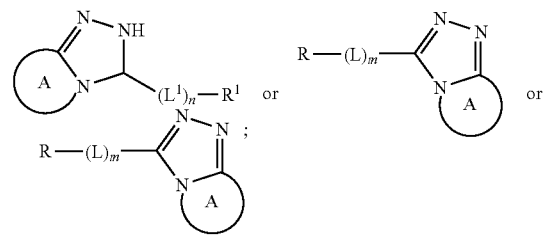

v) imidazoles having the formula:

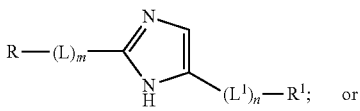

or vi) fused rings comprising a imidazole ring having the formula:

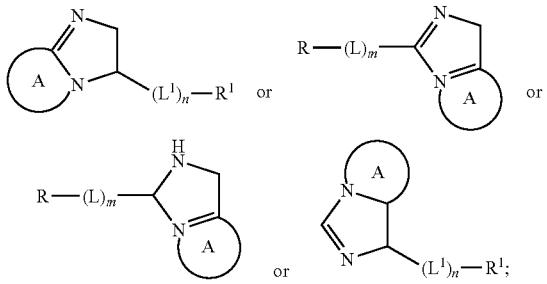

wherein R is chosen from:
i) hydrogen;
ii) $C_1$-$C_{12}$ substituted or unsubstituted linear, branched, or cyclic alkyl;
iii) $C_2$-$C_{12}$ substituted or unsubstituted linear or branched alkenyl;
iv) $C_2$-$C_{12}$ substituted or unsubstituted linear or branched alkynyl;
v) substituted or unsubstituted aryl;
vi) substituted or unsubstituted heteroaryl;
vii) substituted or unsubstituted heterocyclic;
viii) —NHC(O)CH$_3$; or
ix) —C(O)OCH$_3$;
x) —C(O)OH;
$R^1$ is chosen from:
i) hydrogen;
ii) $C_1$-$C_{12}$ substituted or unsubstituted linear, branched, or cyclic alkyl;
iii) $C_2$-$C_{12}$ substituted or unsubstituted linear or branched alkenyl;
iv) $C_2$-$C_{12}$ substituted or unsubstituted linear or branched alkynyl;
v) substituted or unsubstituted aryl;
vi) substituted or unsubstituted heteroaryl;
vii) substituted or unsubstituted heterocyclic;
viii) —NHC(O)CH$_3$;
ix) —C(O)OCH$_3$;
x) —C(O)OH;
xi) —OH; or
xii) —NH$_2$;
$R^2$ is:
i) hydrogen;
ii) halogen; or
iii) R and $R^2$ or $R^1$ and $R^2$ can be taken together to form one or more 5-member or 6-member substituted or unsubstituted cycloalkyl fused rings, substituted or unsubstituted aryl fused rings, 5-member or 6-member heteroaryl fused rings having one or more atoms chosen from nitrogen, oxygen, and sulfur, or substituted or unsubstituted 5-member, 6-member, or 7-member heterocyclic fused rings having one or more atoms chosen from nitrogen, oxygen, and sulfur;

L is a linking unit having the formula:

each $R^{3a}$, $R^{3b}$, $R^{4a}$, and $R^{4b}$ are each independently chosen from:
i) hydrogen;
ii) $C_1$-$C_4$ linear or branched alkyl;
iv) phenyl;
v) hydroxyl; or
vi) cyano;
vii) or two adjacent $R^{3a}$ units or two adjacent $R^{3b}$ units can be taken together to form a double bond;
$R^5$ is chosen from:
ii) —NR$^6$—;
iii) —NR$^6$C(O)—;
iv) —C(O)NR$^6$—;
v) —C(O)—;
vi) —OC(O)—;
vii) —C(O)O—;
vii) —NHC(O)NH—;
viii) —NH(=NR$^6$)NH—;
ix) —O—;
x) —S—; or
xi) —CR$^6$=CR$^6$—;
$R^6$ is chosen from hydrogen or methyl;
the index x is from 0 to 6;
the index y from 0 to 6;
each index z is 0 or 1;
$L^1$ is a linking unit having the formula:

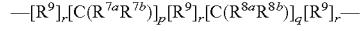

each $R^{7a}$, $R^{7b}$, $R^{8a}$, and $R^{8b}$ are each independently chosen from:
i) hydrogen;
ii) $C_1$-$C_4$ linear or branched alkyl;
iii) phenyl;
iv) hydroxyl; or
v) cyano;
each $R^9$ is chosen from:
i) —NR$^{10}$—;
ii) —NR$^{10}$C(O)—;
iii) —C(O)NR$^{10}$—;
iv) —C(O)—;
v) —OC(O)—;
vi) —C(O)O—;
vii) —NHC(O)NH—;
viii) —C(O)NHC(O)NH—;
ix) —NH(=NR$^{10}$NH—;
x) —O—;
xi) —S—; or
xii) —CR$^{10}$=CR$^{10}$—;
each $R^{10}$ is chosen from hydrogen or methyl;
the index p is from 0 to 6;
the index q from 0 to 6; and
each index r is 0 or 1.

In addition to the pyrazole, [1,2,4]triazole, and imidazole ring systems described above, the disclosed compounds can further comprise one or more ring systems having greater than 4 nitrogen atoms or ring systems comprising sulfur and oxygen atoms in the rings as disclosed herein below and in the examples.

The following are further non-limiting examples of ring systems that the disclosed compounds comprise:

i) 7H-pyrazolo[4,3-e][1,2,4]triazole[1,5-c]pyrimidines, for example:

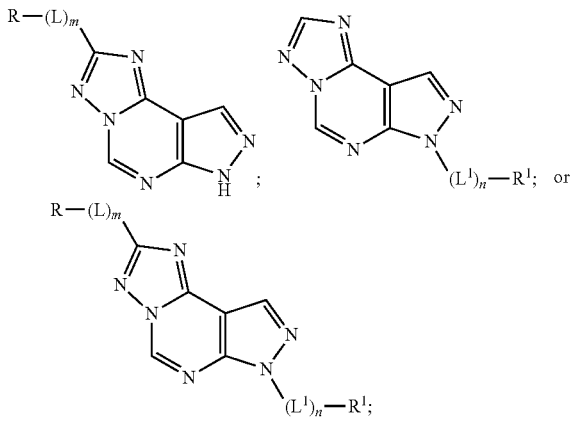

i) 3a,6-dihdyroimidazo[4,5-c]pyrazole[3,4-b]pyridines, for example:

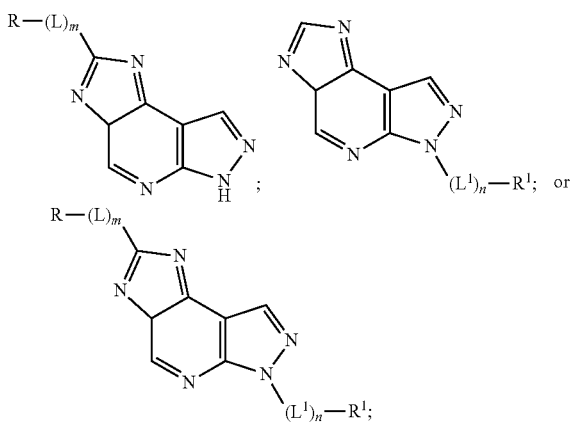

i) 5a,6-dihydro-1H-[1,2,4]triazole[3,4-b]purines, for example:

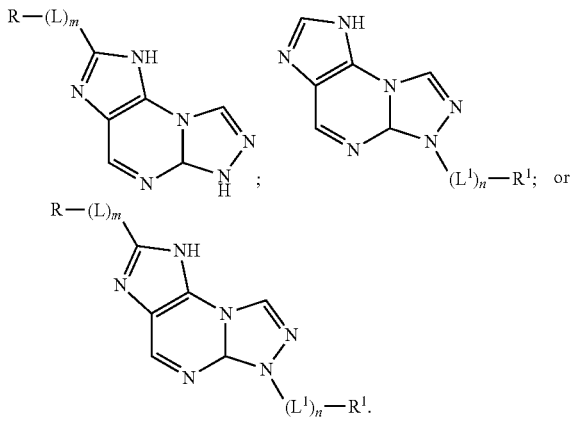

i. R Units

A first category of R units relate to compounds wherein R is a substituted or unsubstituted aryl ring that can have one or more substitutions for hydrogen atoms. A first aspect of aryl R units relates to substituted and unsubstituted phenyl rings having the formula:

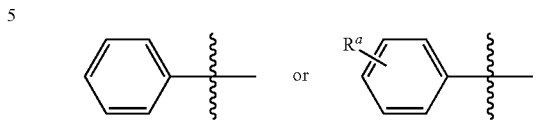

wherein $R^a$ represents from 1 to 5 substitutions for hydrogen.

One embodiment of this aspect relates to compounds wherein R is an unsubstituted phenyl ring. The following are non-limiting examples of this embodiment.

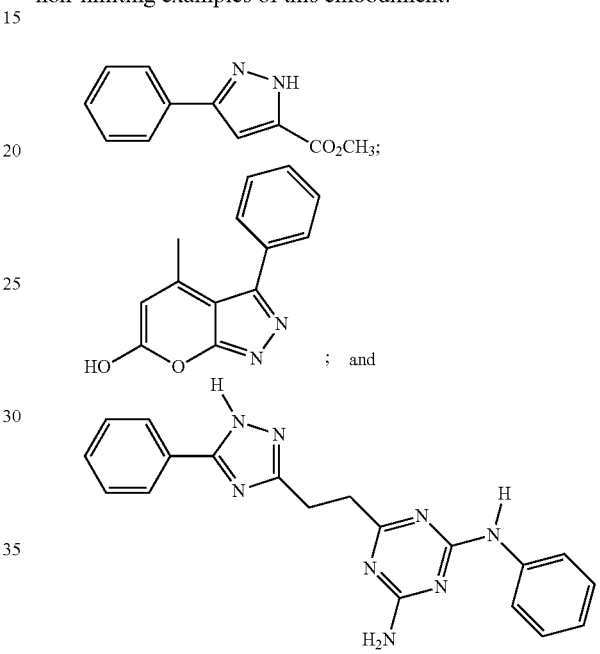

Another embodiment of this aspect relates to compounds wherein R is a substituted phenyl ring wherein the substitutions are chosen from:
i) halogen;
ii) $C_1$-$C_4$ alkyl;
iii) $C_1$-$C_4$ alkoxy;
iv) amino;
v) mono-$C_1$-$C_4$ alkylamino;
vi) di-$C_1$-$C_4$ alkylamino;
vii) nitro; and
viii) cyano.

One iteration of this embodiment relates to compounds wherein R is a mono-substituted phenyl ring non-limiting examples of which include 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-hydroxyphenyl, 3-hydroxyphenyl, 4-hydroxyphenyl, 2-methoxyphenyl, 2-methylphenyl, 3-methylphenyl, 4-methylphenyl, 3-methoxyphenyl, 4-methoxyphenyl, 2-aminophenyl, 3-aminophenyl, 4-aminophenyl, 2-(methylamino)phenyl, 3-(methylamino)phenyl, 4-(methylamino)phenyl, 2-(dimethylamino)phenyl, 3-(dimethylamino)phenyl, 4-(dimethylamino)phenyl, 2-nitrophenyl, 3-nitrophenyl, 4-nitrophenyl, 2-cyanophenyl, 3-cyanophenyl, and 4-cyanophenyl.

Another iteration of this embodiment relates to compounds wherein R is a mono-substituted phenyl ring non-limiting examples of which include 2,3-difluorophenyl, 2,4-difluorophenyl, 2,5-difluorophenyl, 2,6-difluorophenyl, 3,4-difluorophenyl, 3,5-difluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3-dibromophenyl, 2,4-dibromophenyl, 2,5-dibromophenyl, 2,6-dibromophenyl, 3,4-dibromophenyl, 3,5-dibromophenyl, 2,3-dihydroxyphenyl, 2,4-dihydroxyphenyl, 2,5-dihydroxyphenyl, 2,6-dihydroxyphenyl, 3,4-dihydroxyphenyl, 3,5-dihydroxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3-diaminophenyl, 2,4-diaminophenyl, 2,5-diaminophenyl, 2,6-diaminophenyl, 3,4-diaminophenyl, and 3,5-diaminophenyl.

Another aspect of this category relates to substituted and unsubstituted naphthalene rings having the formula:

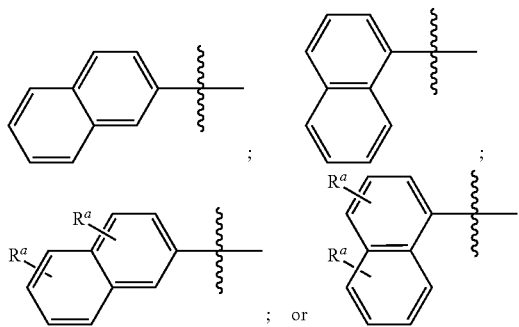

wherein $R^a$ represents from 1 to 7 substitutions for hydrogen

One embodiment of this aspect relates to compounds wherein R is an unsubstituted naphthalene ring. The following are non-limiting examples of this embodiment.

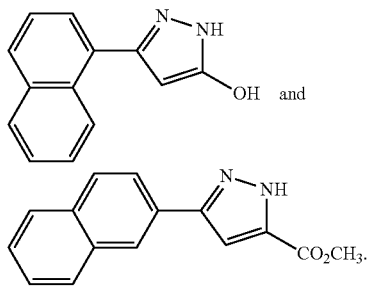

Another embodiment of this aspect relates to compounds wherein R is a substituted naphthalene ring wherein the substitutions are chosen from:
  ix) halogen;
  x) $C_1$-$C_4$ alkyl;
  xi) $C_1$-$C_4$ alkoxy;
  xii) amino;
  xiii) mono-$C_1$-$C_4$ alkylamino;
  xiv) di-$C_1$-$C_4$ alkylamino;
  xv) nitro; and
  xvi) cyano.

One iteration of this embodiment relates to compounds wherein R is a mono-substituted naphthalene-1-yl ring non-limiting examples of which include 2-fluoronaphthalen-1-yl, 3-fluoronaphthalen-1-yl, 4-fluoronaphthalen-1-yl, 5-fluoronaphthalen-1-yl, 6-fluoronaphthalen-1-yl, 7-fluoronaphthalen-1-yl, 8-fluoronaphthalen-1-yl, 2-chloronaphthalen-1-yl, 3-chloro-naphthalen-1-yl, 4-chloronaphthalen-1-yl, 5-chloronaphthalen-1-yl, 6-chloronaphthalen-1-yl, 7-chloronaphthalen-1-yl, 8-chloronaphthalen-1-yl,2-bromonaphthalen-1-yl, 3-bromonaphthalen-1-yl, 4-bromonaphthalen-1-yl, 5-bromonaphthalen-1-yl, 6-bromonaphthalen-1-yl, 7-bromo-naphthalen-1-yl, 8-bromonaphthalen-1-yl, 2-methylnaphthalen-1-yl, 3-methylnaphthalen-1-yl, 4-methylnaphthalen-1-yl, 5-methylnaphthalen-1-yl, 6-methylnaphthalen-1-yl, 7-methyl-naphthalen-1-yl, 8-methylnaphthalen-1-yl, 2-methoxynaphthalen-1-yl, 3-methoxynaphthalen-1-yl, 4-methoxynaphthalen-1-yl, 5-methoxynaphthalen-1-yl, 6-methoxynaphthalen-1-yl, 7-methoxynaphthalen-1-yl, 8-methoxynaphthalen-1-yl, 2-cyanonaphthalen-1-yl, 3-cyano-naphthalen-1-yl, 4-cyanonaphthalen-1-yl, 5-cyanonaphthalen-1-yl, 6-cyanonaphthalen-1-yl, 7-cyanonaphthalen-1-yl, 8-cyanonaphthalen-1-yl, 2-nitronaphthalen-1-yl, 3-nitronaphthalen-1-yl, 4-nitronaphthalen-1-yl, 5-nitronaphthalen-1-yl, 6-nitronaphthalen-1-yl, 7-nitronaphthalen-1-yl, and 8-nitronaphthalen-1-yl.

Another iteration of this embodiment relates to compounds wherein R is a mono-substituted naphthalene-2-yl ring non-limiting examples of which include 1-fluoronaphthalen-2-yl, 3-fluoronaphthalen-2-yl, 4-fluoronaphthalen-2-yl, 5-fluoronaphthalen-2-yl, 6-fluoro-naphthalen-2-yl, 7-fluoronaphthalen-2-yl, 8-fluoronaphthalen-2-yl, 1-chloronaphthalen-2-yl, 3-chloronaphthalen-2-yl, 4-chloronaphthalen-2-yl, 5-chloronaphthalen-2-yl, 6-chloronaphthalen-2-yl, 7-chloronaphthalen-2-yl, 8-chloronaphthalen-2-yl, 1-bromonaphthalen-2-yl, 3-bromo-naphthalen-2-yl, 4-bromonaphthalen-2-yl, 5-bromonaphthalen-2-yl, 6-bromonaphthalen-2-yl, 7-bromonaphthalen-2-yl, 8-bromonaphthalen-2-yl, 1-methylnaphthalen-2-yl, 3-methyl-naphthalen-2-yl, 4-methylnaphthalen-2-yl, 5-methylnaphthalen-2-yl, 6-methylnaphthalen-2-yl, 7-methylnaphthalen-2-yl, 8-methylnaphthalen-2-yl, 1-methoxynaphthalen-2-yl, 3-methoxy-naphthalen-2-yl, 4-methoxynaphthalen-2-yl, 5-methoxynaphthalen-2-yl, 6-methoxynaphthalen-2-yl, 7-methoxynaphthalen-2-yl, 8-methoxynaphthalen-2-yl, 1-cyanonaphthalen-2-yl, 3-cyano-naphthalen-2-yl, 4-cyanonaphthalen-2-yl, 5-cyanonaphthalen-2-yl, 6-cyanonaphthalen-2-yl, 7-cyanonaphthalen-2-yl, 8-cyanonaphthalen-2-yl, 1-nitronaphthalen-2-yl, 3-nitronaphthalen-2-yl, 4-nitronaphthalen-2-yl, 5-nitronaphthalen-2-yl, 6-nitronaphthalen-2-yl, 7-nitronaphthalen-2-yl, and 8-nitronaphthalen-2-yl.

Another category of R units relates to R units that are hydrogen. Non-limiting examples of this category include:

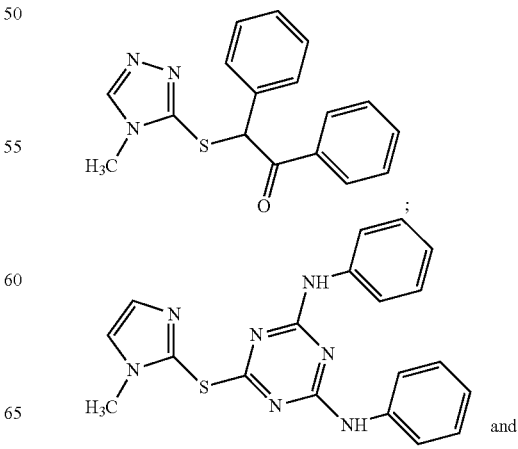

-continued

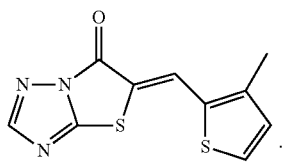

A further category of R units relates to R units that are substituted or unsubstituted heteroaryl rings. One embodiment relates to substituted or unsubstituted 5-member heteroaryl or heterocyclic rings. Non-limiting examples of this embodiment includes:

i) a pyrrolidinyl ring having the formula:

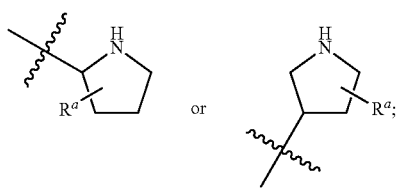

i) a pyrrolyl ring having the formula:

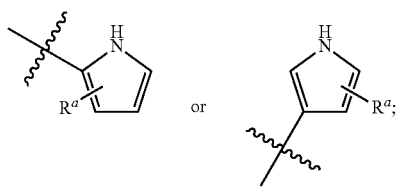

i) a 4,5-dihydroimidazolyl ring having the formula:

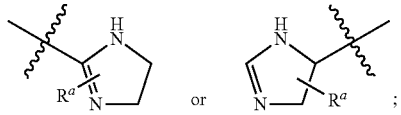

i) a pyrazolyl ring having the formula:

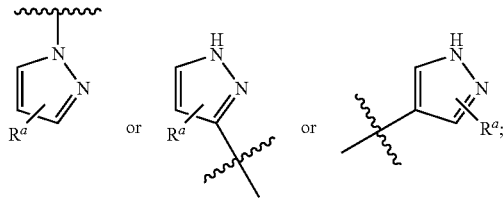

i) an imidazolyl ring having the formula:

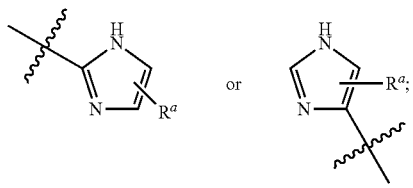

i) a [1,2,3]triazolyl ring having the formula:

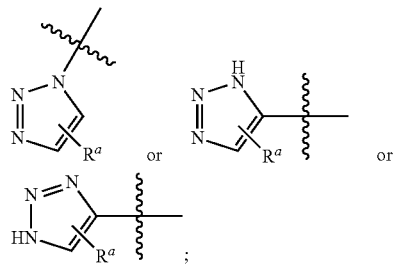

i) a [1,2,4]triazolyl ring having the formula:

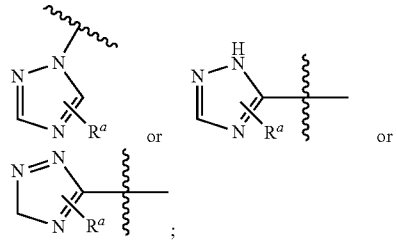

viii) a tetrazolyl ring having the formula:

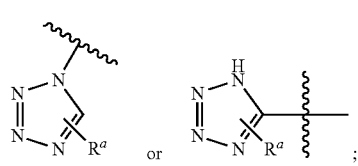

ix) a [1,3,4] or [1,2,4]oxadiazolyl ring having the formula:

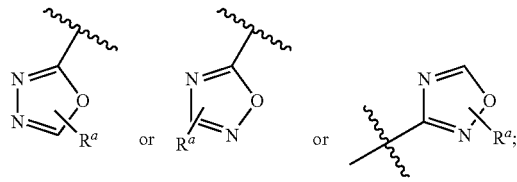

x) a pyrrolidinonyl ring having the formula:

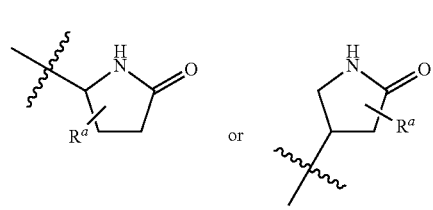

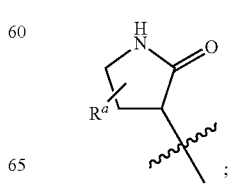

xi) a imidazolidinonyl ring having the formula:

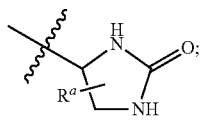

xii) a imidazol-2-only ring having the formula:

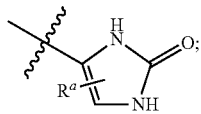

xiii) a oxazolyl ring having the formula:

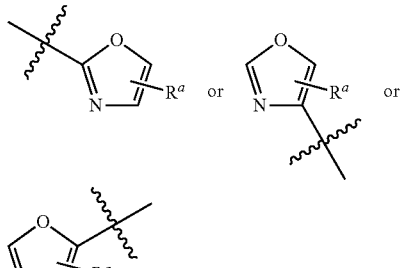

xiv) a isoxazolyl ring having the formula:

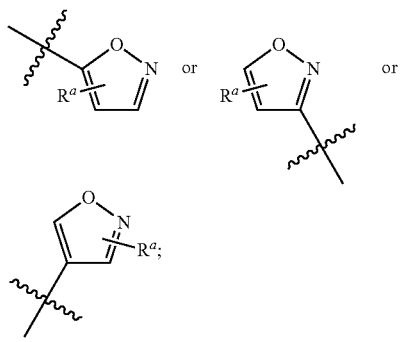

xv) a thiazolyl ring having the formula:

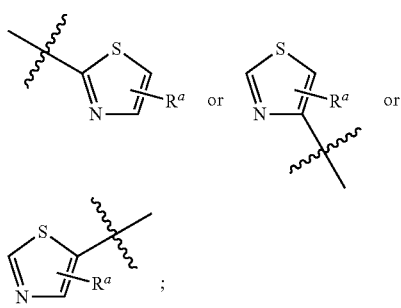

xvi) a furanly ring having the formula:

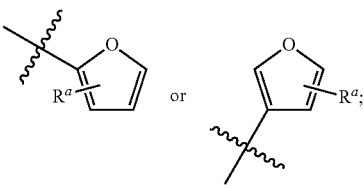

xvii) a thiophenyl having the formula:

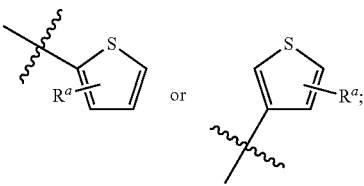

wherein $R^a$ represents from 1 to 3 substitutions for hydrogen. Non-limiting examples of substitutions for hydrogen include:
   i) halogen;
   ii) $C_1$-$C_4$ alkyl;
   iii) $C_1$-$C_4$ alkoxy;
   iv) amino;
   v) mono-$C_1$-$C_4$ alkylamino;
   vi) di-$C_1$-$C_4$ alkylamino;
   vii) nitro; and
   viii) cyano.

Non-limiting examples of this category include:

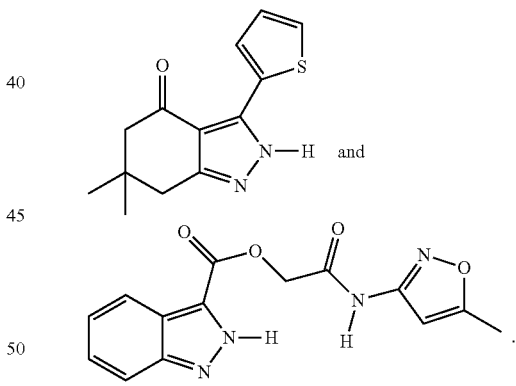

Another embodiment relates to substituted or unsubstituted 6-member heteroaryl or heterocyclic rings. Non-limiting examples of this embodiment includes:
   i) a morpholinyl ring having the formula:

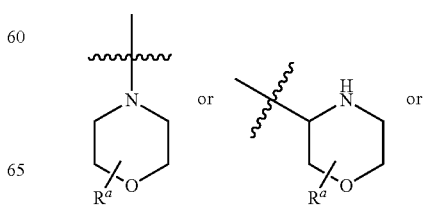

-continued

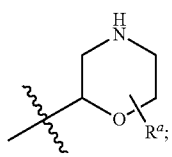

ii) a piperidinyl ring having the formula:

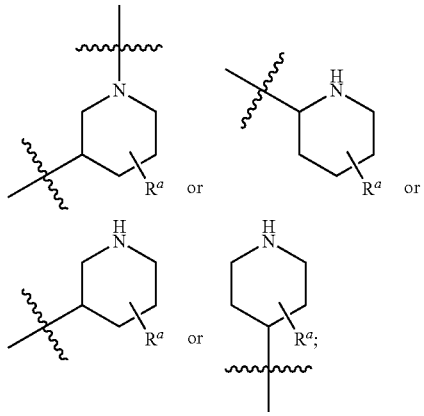

iii) a pyridinyl ring having the formula:

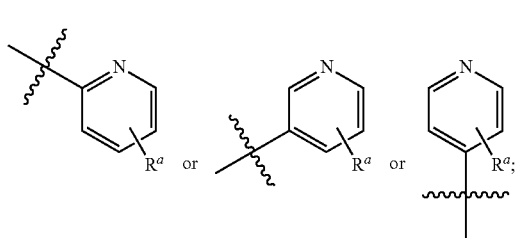

iv) a pyrimidinyl ring having the formula:

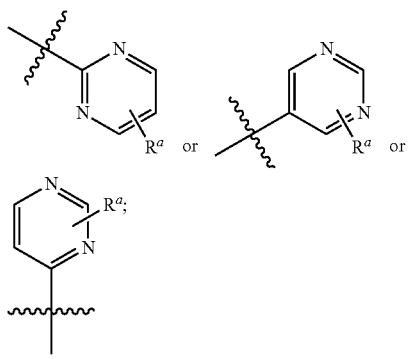

v) a piperazinyl ring having the formula:

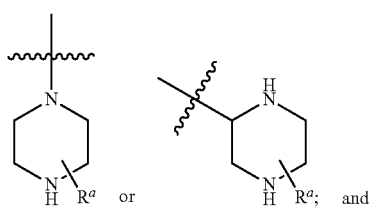

vi) a triazinyl ring having the formula:

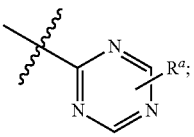

wherein $R^a$ represents from 1 to 5 substitutions for hydrogen. Non-limiting examples of substitutions for hydrogen include:
  i) halogen;
  ii) $C_1$-$C_4$ alkyl;
  iii) $C_1$-$C_4$ alkoxy;
  iv) amino;
  v) mono-$C_1$-$C_4$ alkylamino;
  vi) di-$C_1$-$C_4$ alkylamino;
  vii) nitro; and
  viii) cyano.

Another category of R units relates to substituted or unsubstituted $C_7$, $C_8$ or $C_9$ heterocyclic or heteroaryl fused rings, non-limiting examples of which can be independently chosen from:

i) benzoimidazolyl rings having the formula:

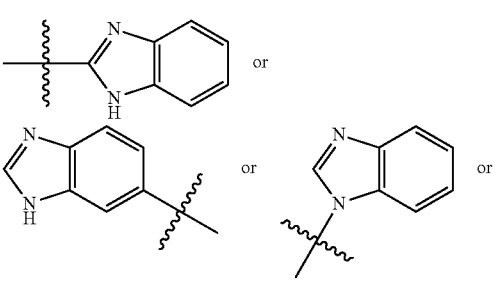

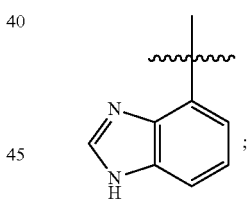

;

ii) benzothiazolyl rings having the formula:

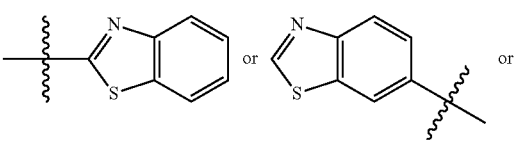

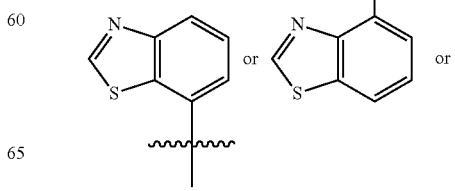

-continued

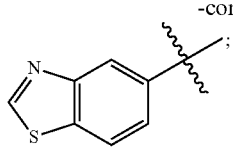

iii) benzoxazolyl rings having the formula:

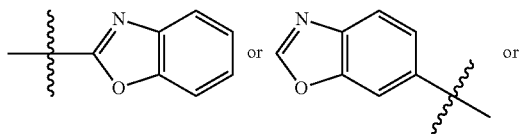

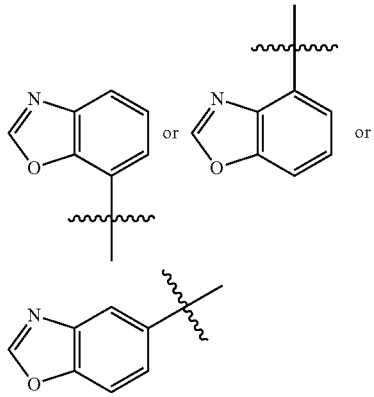

iv) quinazolinyl rings having the formula:

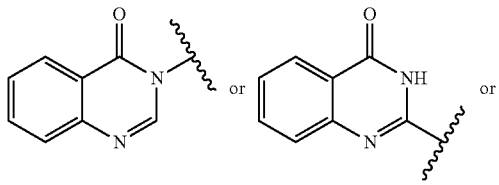

v) 2,3-dihydrobenzo[1,4]dioxinyl rings having the formula:

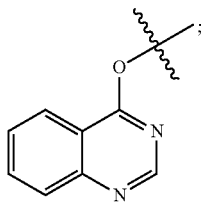

vi) tetrahydroquinolinyl rings having the formula:

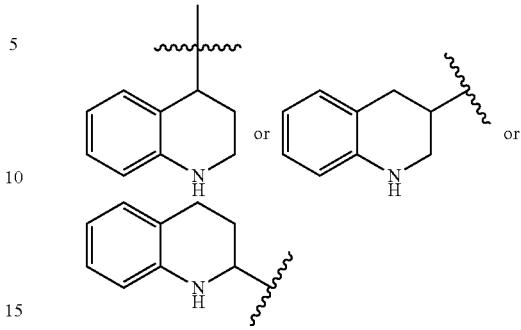

wherein $R^a$ represents one or more substitutions for hydrogen. Non-limiting examples of substitutions for hydrogen include
  i) halogen;
  ii) $C_1$-$C_4$ alkyl;
  iii) $C_1$-$C_4$ alkoxy;
  iv) amino;
  v) mono-$C_1$-$C_4$ alkylamino;
  vi) di-$C_1$-$C_4$ alkylamino;
  vii) nitro; and
  viii) cyano.

A non-limiting example of this category includes:

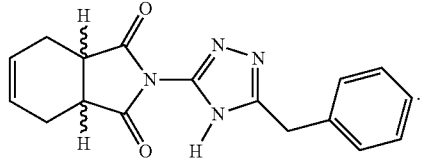 [SMILES: O=C1C2CC=CCC2C(=O)N1c1nnc(Cc2ccccc2)[nH]1]

ii. $R^1$ Units

A first category of $R^1$ units relate to compounds wherein $R^1$ is a substituted or unsubstituted aryl ring that can have one or more substitutions for hydrogen atoms. A first aspect of aryl R units relates to substituted and unsubstituted phenyl rings having the formula:

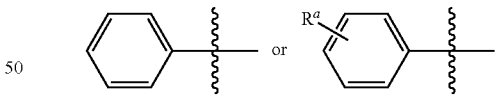

wherein $R^a$ represents from 1 to 5 substitutions for hydrogen.

One embodiment of this aspect relates to compounds wherein $R^1$ is an unsubstituted phenyl ring. The following are non-limiting examples of this embodiment.

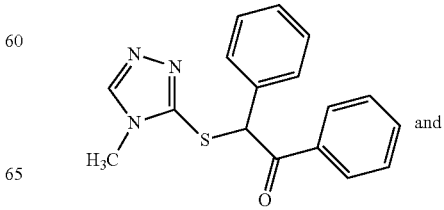

-continued

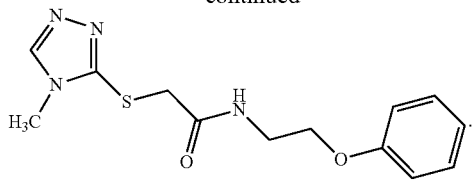

Another embodiment of this aspect relates to compounds wherein $R^1$ is a substituted phenyl ring wherein the substitutions are chosen from:
 i) halogen;
 ii) $C_1$-$C_4$ alkyl;
 iii) $C_1$-$C_4$ alkoxy;
 iv) amino;
 v) mono-$C_1$-$C_4$ alkylamino;
 vi) di-$C_1$-$C_4$ alkylamino;
 vii) nitro; and
 viii) cyano.

One iteration of this embodiment relates to compounds wherein $R^1$ is a mono-substituted phenyl ring non-limiting examples of which include 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-hydroxyphenyl, 3-hydroxyphenyl, 4-hydroxyphenyl, 2-methoxyphenyl, 2-methylphenyl, 3-methylphenyl, 4-methylphenyl, 3-methoxyphenyl, 4-methoxyphenyl, 2-aminophenyl, 3-aminophenyl, 4-aminophenyl, 2-(methylamino)phenyl, 3-(methylamino)phenyl, 4-(methylamino)phenyl, 2-(dimethylamino)phenyl, 3-(dimethylamino)phenyl, 4-(dimethylamino)phenyl, 2-nitrophenyl, 3-nitrophenyl, 4-nitrophenyl, 2-cyanophenyl, 3-cyanophenyl, and 4-cyanophenyl.

Another iteration of this embodiment relates to compounds wherein $R^1$ is a mono-substituted phenyl ring non-limiting examples of which include 2,3-difluorophenyl, 2,4-difluorophenyl, 2,5-difluorophenyl, 2,6-difluorophenyl, 3,4-difluorophenyl, 3,5-difluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3-dibromophenyl, 2,4-dibromophenyl, 2,5-dibromophenyl, 2,6-dibromophenyl, 3,4-dibromophenyl, 3,5-dibromophenyl, 2,3-dihydroxyphenyl, 2,4-dihydroxyphenyl, 2,5-dihydroxyphenyl, 2,6-dihydroxyphenyl, 3,4-dihydroxyphenyl, 3,5-dihydroxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3-diaminophenyl, 2,4-diaminophenyl, 2,5-diaminophenyl, 2,6-diaminophenyl, 3,4-diaminophenyl, and 3,5-diaminophenyl.

A non-limiting example of this embodiment includes:

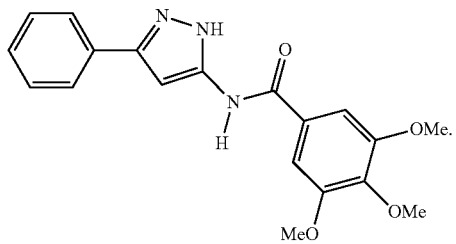 [SMILES: COc1cc(C(=O)Nc2cc(-c3ccccc3)n[nH]2)cc(OC)c1OC]

A further category of $R^1$ units relates to $R^1$ units that are substituted or unsubstituted heteroaryl rings. One embodiment relates to substituted or unsubstituted 5-member heteroaryl or heterocyclic rings. Non-limiting examples of this embodiment includes:

i) a pyrrolidinyl ring having the formula:

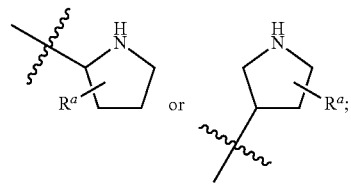

ii) a pyrrolyl ring having the formula:

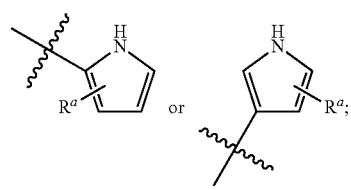

iii) a 4,5-dihydroimidazolyl ring having the formula:

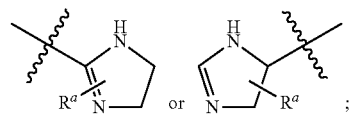

iv) a pyrazolyl ring having the formula:

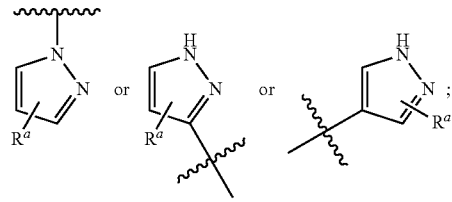

v) an imidazolyl ring having the formula:

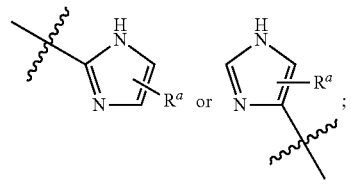

vi) a [1,2,3]triazolyl ring having the formula:

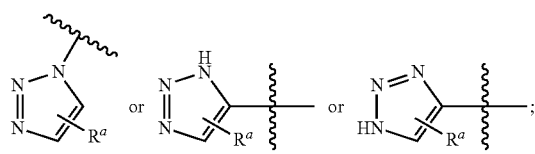

vii) a [1,2,4]triazolyl ring having the formula:

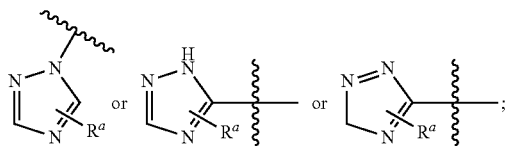

viii) a tetrazolyl ring having the formula:

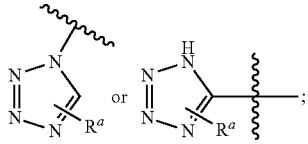

ix) a [1,3,4] or [1,2,4]oxadiazolyl ring having the formula:

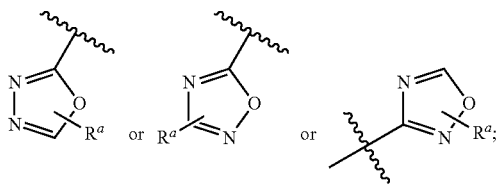

x) a pyrrolidinonyl ring having the formula:

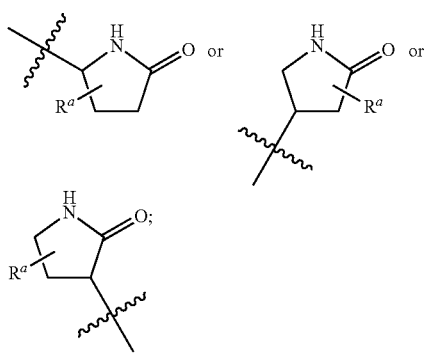

xi) a imidazolidinonyl ring having the formula:

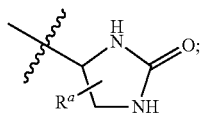

xii) a imidazol-2-only ring having the formula:

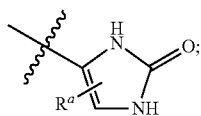

xiii) a oxazolyl ring having the formula:

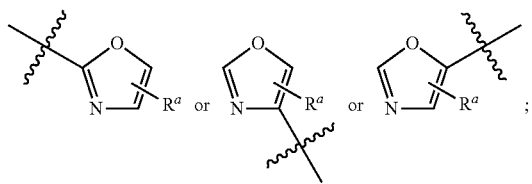

xiv) a isoxazolyl ring having the formula:

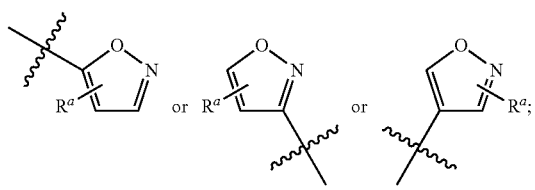

xv) a thiazolyl ring having the formula:

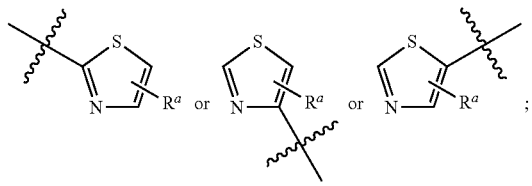

xvi) a furanly ring having the formula:

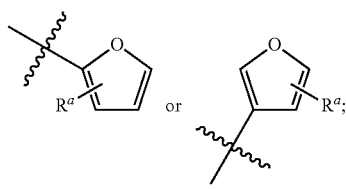

xvii) a thiophenyl having the formula:

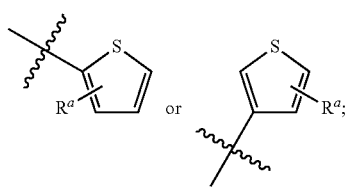

wherein $R^a$ represents from 1 to 3 substitutions for hydrogen. Non-limiting examples of substitutions for hydrogen include:
  i) halogen;
  ii) $C_1$-$C_4$ alkyl;
  iii) $C_1$-$C_4$ alkoxy;
  iv) amino;
  v) mono-$C_1$-$C_4$ alkylamino;
  vi) di-$C_1$-$C_4$ alkylamino;
  vii) nitro; and
  viii) cyano.

Non-limiting examples of this category include:

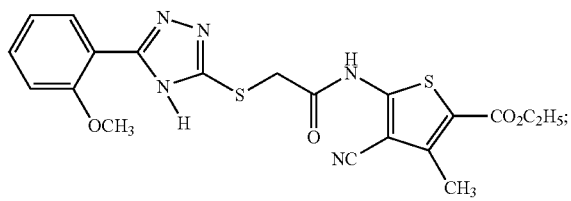

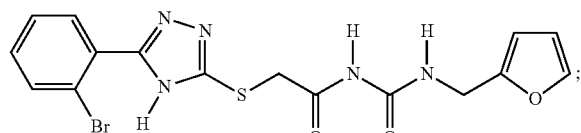

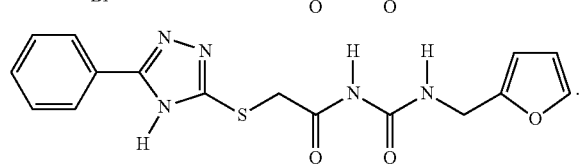

Another embodiment relates to substituted or unsubstituted 6-member heteroaryl or heterocyclic rings. Non-limiting examples of this embodiment includes:

i) a morpholinyl ring having the formula:

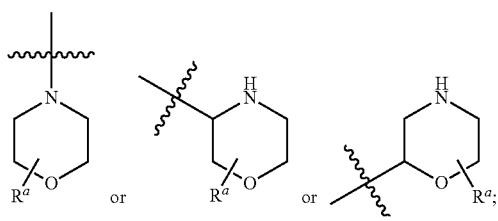

ii) a piperidinyl ring having the formula:

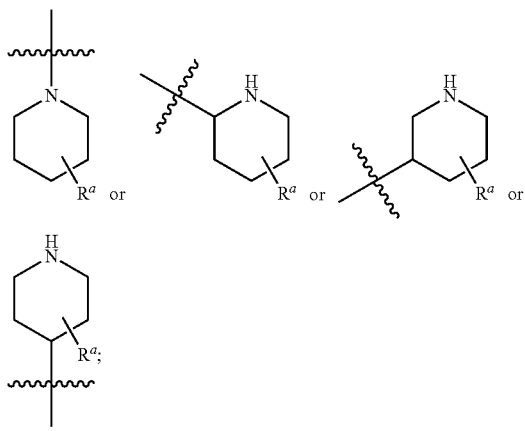

iii) a pyridinyl ring having the formula:

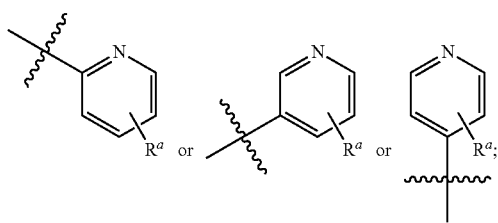

iv) a pyrimidinyl ring having the formula:

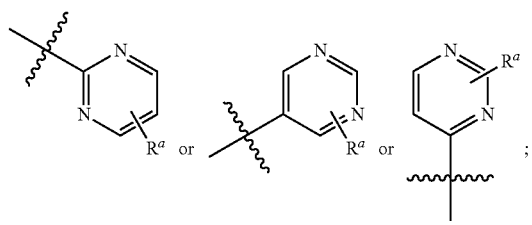

v) a piperazinyl ring having the formula:

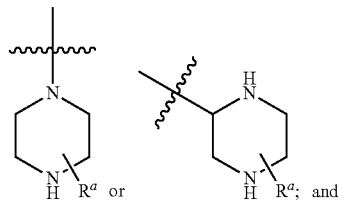

vi) a triazinyl ring having the formula:

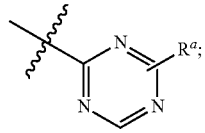

wherein $R^a$ represents from 1 to 5 substitutions for hydrogen. Non-limiting examples of substitutions for hydrogen include:
  i) halogen;
  ii) $C_1$-$C_4$ alkyl;
  iii) $C_1$-$C_4$ alkoxy;
  iv) amino;
  v) mono-$C_1$-$C_4$ alkylamino;
  vi) di-$C_1$-$C_4$ alkylamino;
  vii) nitro; and
  viii) cyano.

Non-limiting examples of this category include:

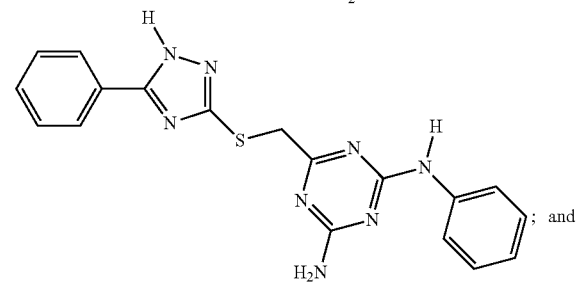

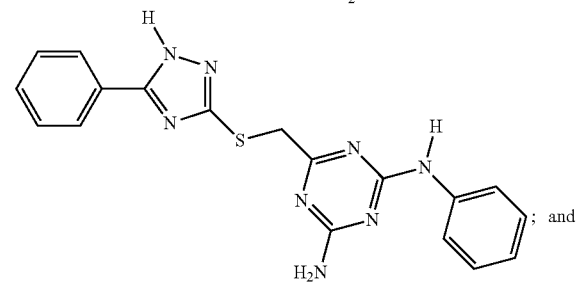

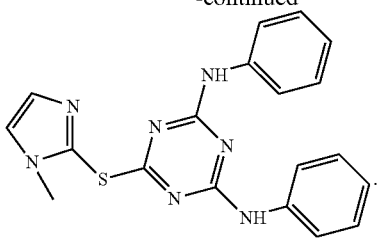

Another category of R¹ units relates to substituted or unsubstituted $C_7$, $C_8$ or $C_9$ heterocyclic or heteroaryl fused rings, non-limiting examples of which can be independently chosen from:

i) benzoimidazolyl rings having the formula:

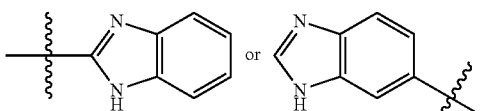

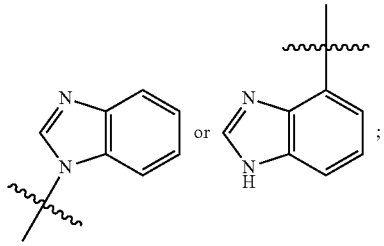

ii) benzothiazolyl rings having the formula:

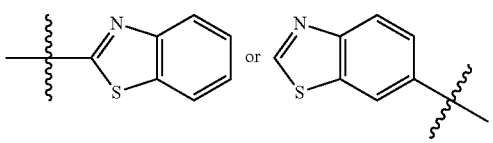

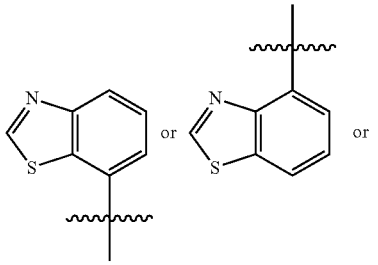

iii) benzoxazolyl rings having the formula:

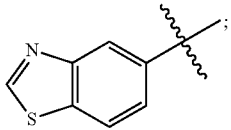

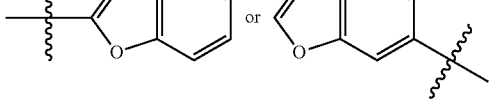

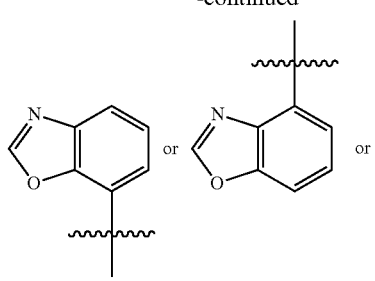

iv) quinazolinyl rings having the formula:

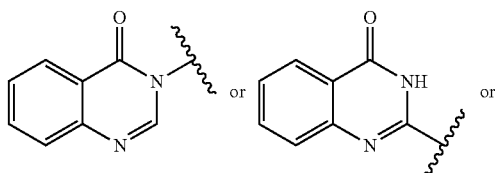

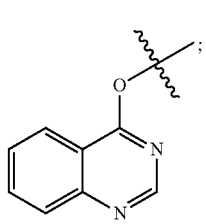

v) 2,3-dihydrobenzo[1,4]dioxinyl rings having the formula:

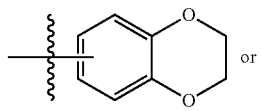

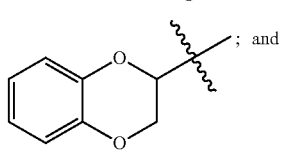

vi) tetrahydroquinolinyl rings having the formula:

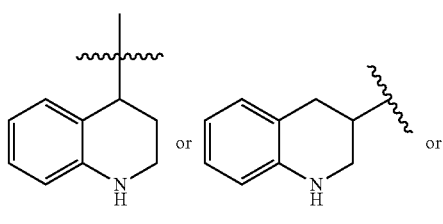

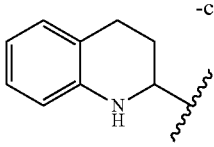

wherein $R^a$ represents one or more substitutions for hydrogen. Non-limiting examples of substitutions for hydrogen include
   i) halogen;
   ii) $C_1$-$C_4$ alkyl;
   iii) $C_1$-$C_4$ alkoxy;
   iv) amino;
   v) mono-$C_1$-$C_4$ alkylamino;
   vi) di-$C_1$-$C_4$ alkylamino;
   vii) nitro; and
   viii) cyano.

A yet further category of $R^1$ units relates to $R^1$ units chosen from:
   i) —NHC(O)CH$_3$;
   ii) —C(O)OCH$_3$;
   iii) —C(O)OH;
   iv) —OH; or
   v) —NH$_2$.

Non-limiting examples of this category include:

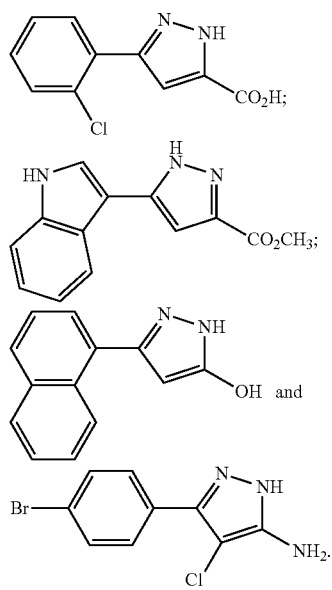

iii. $R^2$ Units

One category of $R^2$ units relate to compounds wherein R and $R^2$ or $R^1$ and $R^2$ can be taken together to form ring A comprising one or more 5-member or 6-member substituted or unsubstituted cycloalkyl fused rings, substituted or unsubstituted aryl fused rings, 5-member or 6-member heteroaryl fused rings having one or more atoms chosen from nitrogen, oxygen, and sulfur, or substituted or unsubstituted 5-member, 6-member, or 7-member heterocyclic fused rings having one or more atoms chosen from nitrogen, oxygen, and sulfur;

One embodiment of this category relates to R and $R^2$ units that are taken together to form a ring system having the formula:

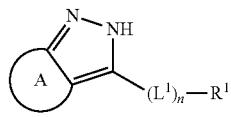

wherein $R^1$, $L^1$, and the index n are the same as defined herein above. One iteration of this embodiment relates to ring systems wherein the A ring is a substituted of unsubstituted cycloalkyl ring wherein the ring can further comprise a double bond. Non-limiting examples include:

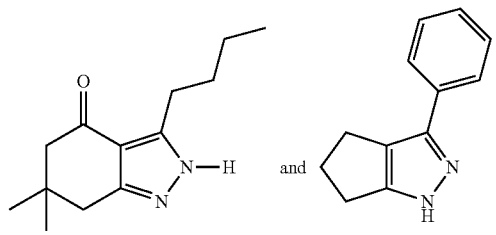

Another iteration of this embodiment relates to ring systems wherein the A ring is a substituted of unsubstituted aryl ring. Non-limiting examples include:

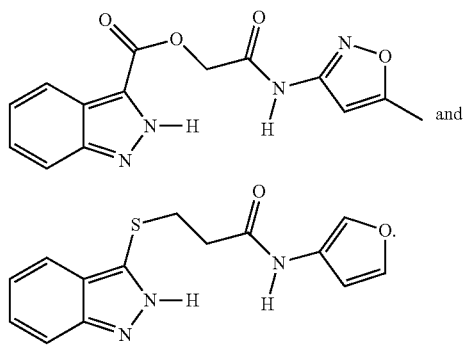

A further iteration of this embodiment relates to ring systems wherein the A ring is a substituted of unsubstituted heteroaryl or heterocyclic ring. Non-limiting examples include:

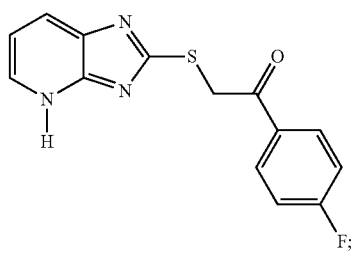

31

-continued

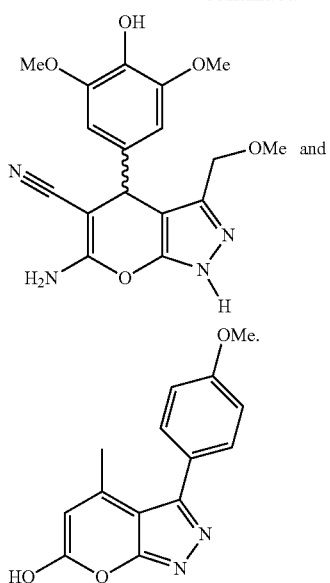

Another category relates to $R^1$ and $R^2$ or R and $R^2$ units that are taken together to form a ring system having the formula:

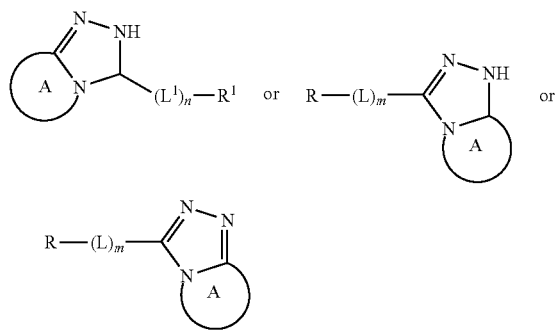

wherein R, $R^1$, L, $L^1$, and the indices m and n are further defined herein. The A ring is a substituted or unsubstituted cycloalkyl ring, aryl ring, heterocyclic ring, or heteroaryl ring. Non-limiting examples of this category include:

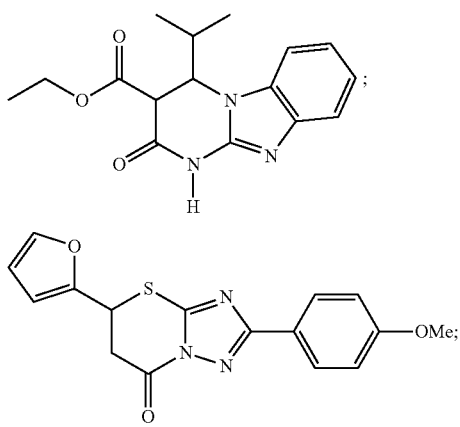

32

-continued

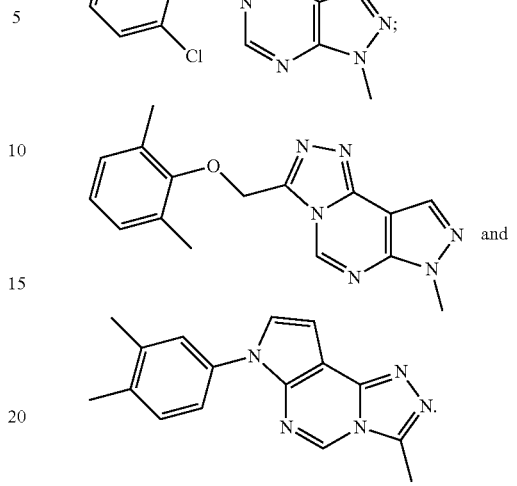

iv. L Units

L units are linking units that can connect R units to the nitrogen containing rings disclosed herein. L units can also be part of the formation of rings wherein R and $R^2$ units are taken together to form ring A that comprises one or more 5-member or 6-member substituted or unsubstituted cycloalkyl fused rings, substituted or unsubstituted aryl fused rings, 5-member or 6-member heteroaryl fused rings having one or more atoms chosen from nitrogen, oxygen, and sulfur, or substituted or unsubstituted 5-member, 6-member, or 7-member heterocyclic fused rings having one or more atoms chosen from nitrogen, oxygen, and sulfur.

L units have the formula:

wherein each $R^{3a}$, $R^{3b}$, $R^{4a}$, and $R^{4b}$ are each independently chosen from:
  i) hydrogen;
  ii) $C_1$-$C_4$ linear or branched alkyl;
  iii) phenyl;
  iv) hydroxyl; or
  v) cyano;
  vi) or two adjacent $R^{3a}$ units or two adjacent $R^{3b}$ units can be taken together to form a double bond;
the index x is an integer from 0 to 6 and the index y is an integer from 0 to 6.
$R^5$ is a connecting unit each of which are independently chosen from:
  i) —$NR^6$—;
  ii) —$NR^6C(O)$—;
  iii) —$C(O)NR^6$—;
  iv) —C(O)—;
  v) —OC(O)—;
  vi) —C(O)O—;
  vii) —NHC(O)NH—;
  viii) —NH(=$NR^6$)NH—;
  ix) —O—;
  x) —S—; or
  xi) —$CR^6$=$CR^6$—;
$R^6$ is chosen from hydrogen or methyl. When the index z is equal to 0 a particular $R^5$ unit is absent, when z is equal to 1 then a particular $R^5$ unit is present.

One category of L units relates to linking units having the formula:

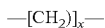—[CH$_2$]$_x$— wherein the index x is from 1 to 6. Examples of this category include:
i) —CH$_2$—;
ii) —CH$_2$CH$_2$—;
iii) —CH$_2$CH$_2$CH$_2$—;
iv) —CH$_2$CH$_2$CH$_2$CH$_2$—;
v) —CH$_2$CH$_2$CH$_2$CH$_2$CH$_2$—; and
vi) —CH$_2$CH$_2$CH$_2$CH$_2$CH$_2$CH$_2$—.

Another category of L units relates to linking units having the formula:

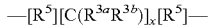—[R$^5$][C(R$^{3a}$R$^{3b}$)]$_x$[R$^5$]— wherein each R$^{3a}$ and R$^{3b}$ is independently hydrogen or methyl, and R$^5$ is chosen from
i) —NR$^6$C(O)—;
ii) —C(O)NR$^6$—;
iii) —C(O)—;
iv) —OC(O)—;
v) —C(O)O—;
vi) —O—; or
vii) —S—.

One embodiment of this category relates to linking units having the formula:

—S[CH$_2$)]$_x$NHC(O)— wherein x is from 2 to 6. Examples of this embodiment include:
i) —SCH$_2$CH$_2$NHC(O)—;
ii) —SCH$_2$CH$_2$CH$_2$NHC(O)—;
iii) —SCH$_2$CH$_2$CH$_2$CH$_2$NHC(O)—; and
iv) —SCH$_2$CH$_2$CH$_2$CH$_2$CH$_2$NHC(O)—.

Another embodiment of this category relates to linking units having the formula:

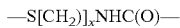—S[CH$_2$)]$_x$C(O)NH— wherein x is from 2 to 6. Examples of this embodiment include:
i) —SCH$_2$CH$_2$C(O)NH—;
ii) —SCH$_2$CH$_2$CH$_2$C(O)NH—;
iii) —SCH$_2$CH$_2$CH$_2$CH$_2$C(O)NH—; and
iv) —SCH$_2$CH$_2$CH$_2$CH$_2$CH$_2$C(O)NH—.

A further embodiment of this category relates to linking units having the formula:

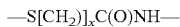—O[CH$_2$)]$_x$NHC(O)— wherein x is from 2 to 6. Examples of this embodiment include:
i) —OCH$_2$CH$_2$NHC(O)—;
ii) —OCH$_2$CH$_2$CH$_2$NHC(O)—;
iii) —OCH$_2$CH$_2$CH$_2$CH$_2$NHC(O)—; and
iv) —OCH$_2$CH$_2$CH$_2$CH$_2$CH$_2$NHC(O)—.

A yet further embodiment of this category relates to linking units having the formula:

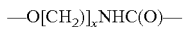—S[CH$_2$)]$_x$C(O)— wherein x is from 2 to 6. Examples of this embodiment include:
i) —SCH$_2$CH$_2$C(O)—;
ii) —SCH$_2$CH$_2$CH$_2$C(O)—;
iii) —SCH$_2$CH$_2$CH$_2$CH$_2$C(O)—; and
iv) —SCH$_2$CH$_2$CH$_2$CH$_2$CH$_2$C(O)—.

A still yet further embodiment of this category relates to linking units having the formula:

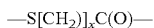—O[CH$_2$)]$_x$C(O)— wherein x is from 2 to 6. Examples of this embodiment include:
i) —OCH$_2$CH$_2$C(O)—;
ii) —OCH$_2$CH$_2$CH$_2$C(O)—;
iii) —OCH$_2$CH$_2$CH$_2$CH$_2$C(O)—; and
iv) —OCH$_2$CH$_2$CH$_2$CH$_2$CH$_2$C(O)—.

A further category of L units relates to linking units having the formula:

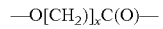—[R$^5$][C(R$^{3a}$R$^{3b}$)]$_x$[R$^5$][C(R$^{4a}$R$^{4b}$)]$_y$[R$^5$]$_z$— wherein each R$^{3a}$, R$^{3b}$, R$^{4a}$, and R$^{4b}$ is independently hydrogen or methyl, and R$^5$ is chosen from
i) —NR$^6$C(O)—;
ii) —C(O)NR$^6$—;
iii) —C(O)—;
iv) —OC(O)—;
v) —C(O)O—;
vi) —O—; or
vii) —S—;
and the index z is 0 or 1.

One embodiment of this category relates to linking units having the formula:

—S[CH$_2$)]$_x$NHC(O)[CH$_2$)]$_y$— wherein x is from 2 to 6. Examples of this embodiment include:
i) —SCH$_2$CH$_2$NHC(O)CH$_2$CH$_2$—;
ii) —SCH$_2$CH$_2$CH$_2$NHC(O)CH$_2$—;
iii) —SCH$_2$CH$_2$CH$_2$CH$_2$NHC(O)CH$_2$CH$_2$—; and
iv) —SCH$_2$CH$_2$CH$_2$NHC(O)CH$_2$CH$_2$—.

Another embodiment of this category relates to linking units having the formula:

—S[CH$_2$)]$_x$C(O)[CH$_2$)]$_y$— wherein x is from 2 to 6. Examples of this embodiment include:
i) —SCH$_2$CH$_2$C(O)CH$_2$CH$_2$—;
ii) —SCH$_2$CH$_2$CH$_2$C(O)CH$_2$—;
iii) —SCH$_2$CH$_2$CH$_2$CH$_2$C(O)CH$_2$CH$_2$—; and
iv) —SCH$_2$CH$_2$CH$_2$C(O)CH$_2$CH$_2$—.

A further embodiment of this category relates to linking units having the formula:

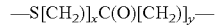—S[CH$_2$)]$_x$NHC(O)[CH$_2$)]$_y$— wherein x is from 2 to 6. Examples of this embodiment include:
i) —SCH$_2$CH$_2$NHC(O)CH$_2$CH$_2$—;
ii) —SCH$_2$CH$_2$CH$_2$NHC(O)CH$_2$—;
iii) —SCH$_2$CH$_2$CH$_2$CH$_2$NHC(O)CH$_2$CH$_2$—; and
iv) —SCH$_2$CH$_2$CH$_2$NHC(O)CH$_2$CH$_2$—.

A yet further embodiment of this category relates to linking units having the formula:

—S[CH$_2$)]$_x$NHC(O)[CH$_2$)]$_y$S— wherein x is from 2 to 6. Examples of this embodiment include:
v) —SCH$_2$CH$_2$NHC(O)CH$_2$CH$_2$S—;
vi) —SCH$_2$CH$_2$CH$_2$NHC(O)CH$_2$—S;
vii) —SCH$_2$CH$_2$CH$_2$CH$_2$NHC(O)CH$_2$CH$_2$S—; and
viii) —SCH$_2$CH$_2$CH$_2$NHC(O)CH$_2$CH$_2$S—.

A yet another embodiment of this category relates to linking units having the formula:

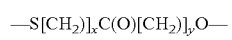—S[CH$_2$)]$_x$C(O)[CH$_2$)]$_y$O— wherein x is from 2 to 6. Examples of this embodiment include:
v) —SCH$_2$CH$_2$C(O)CH$_2$CH$_2$O—;
vi) —SCH$_2$CH$_2$CH$_2$C(O)CH$_2$O—;
vii) —SCH$_2$CH$_2$CH$_2$CH$_2$C(O)CH$_2$CH$_2$O—; and
viii) —SCH$_2$CH$_2$CH$_2$C(O)CH$_2$CH$_2$O—.

A yet still further embodiment of this category relates to linking units having the formula:

—S[CH$_2$)]$_x$NHC(O)[CH$_2$)]$_y$O— wherein x is from 2 to 6. Examples of this embodiment include:
v) —SCH$_2$CH$_2$NHC(O)CH$_2$CHO$_2$—;
vi) —SCH$_2$CH$_2$CH$_2$NHC(O)CH$_2$O—;
vii) —SCH$_2$CH$_2$CH$_2$CH$_2$NHC(O)CH$_2$CH$_2$O—; and
viii) —SCH$_2$CH$_2$CH$_2$NHC(O)CH$_2$CH$_2$O—.

v. L$^1$ Units

L$^1$ units are linking units that can connect R units to the nitrogen containing rings disclosed herein. L$^1$ units can also be part of the formation of rings wherein R$^1$ and R$^2$ units are taken together to form ring A that comprises one or more 5-member or 6-member substituted or unsubstituted cycloalkyl fused rings, substituted or unsubstituted aryl fused rings, 5-member or 6-member heteroaryl fused rings having one or more atoms chosen from nitrogen, oxygen, and sulfur, or substituted or unsubstituted 5-member, 6-member, or 7-member heterocyclic fused rings having one or more atoms chosen from nitrogen, oxygen, and sulfur.

L$^1$ units have the formula:

—[R$^9$]$_r$[C(R$^{7a}$R$^{7b}$)]$_p$[R$^9$]$_r$[C(R$^{8a}$R$^{8b}$)]$_q$[R$^9$]$_r$— wherein each R$^{7a}$, R$^{7b}$, R$^{8a}$, and R$^{8b}$ are each independently chosen from:
i) hydrogen;
ii) C$_1$-C$_4$ linear or branched alkyl;
iii) phenyl;
iv) hydroxyl; or
v) cyano;
vi) or two adjacent R$^{7a}$ units or two adjacent R$^{7b}$ units can be taken together to form a double bond;
the index p is an integer from 0 to 6 and the index q is an integer from 0 to 6.

R$^9$ is a connecting unit each of which are independently chosen from:
i) —NR$^{10}$—;
ii) —NR$^{10}$C(O)—;
iii) —C(O)NR$^{10}$—;
iv) —C(O)—;
v) —OC(O)—;
vi) —C(O)O—;
vii) —NHC(O)NH—;
viii) —NH(=NR$^{10}$)NH—;
ix) —O—;
x) —S—; or
xi) —CR$^{10}$=CR$^{10}$—;

R$^{10}$ is chosen from hydrogen or methyl. When the index r is equal to 0 a particular R$^9$ unit is absent, when z is equal to 1 then a particular R$^9$ unit is present.

One category of L units relates to linking units having the formula:

—[CH$_2$)]$_p$— wherein the index p is from 1 to 6. Examples of this category include:
i) —CH$_2$—;
ii) —CH$_2$CH$_2$—;
iii) —CH$_2$CH$_2$CH$_2$—;
iv) —CH$_2$CH$_2$CH$_2$CH$_2$—;
v) —CH$_2$CH$_2$CH$_2$CH$_2$CH$_2$—; and
vi) —CH$_2$CH$_2$CH$_2$CH$_2$CH$_2$CH$_2$—.

Another category of L units relates to linking units having the formula:

—[R$^9$][C(R$^{7a}$R$^{7b}$)]$_p$[R$^9$]— wherein each R$^{7a}$ and R$^{7b}$ is independently hydrogen or methyl, and R$^9$ is chosen from
i) —NR$^6$C(O)—;
ii) —C(O)NR$^6$—;
iii) —C(O)—;
iv) —OC(O)—;
v) —C(O)O—;
vi) —O—; or
vii) —S—.

One embodiment of this category relates to linking units having the formula:

—S[CH$_2$)]$_p$NHC(O)— wherein x is from 2 to 6. Examples of this embodiment include:
i) —SCH$_2$CH$_2$NHC(O)—;
ii) —SCH$_2$CH$_2$CH$_2$NHC(O)—;
iii) —SCH$_2$CH$_2$CH$_2$CH$_2$NHC(O)—; and
iv) —SCH$_2$CH$_2$CH$_2$CH$_2$CH$_2$NHC(O)—.

Another embodiment of this category relates to linking units having the formula:

—S[CH$_2$)]$_p$C(O)NH— wherein x is from 2 to 6. Examples of this embodiment include:
i) —SCH$_2$CH$_2$C(O)NH—;
ii) —SCH$_2$CH$_2$CH$_2$C(O)NH—;
iii) —SCH$_2$CH$_2$CH$_2$CH$_2$C(O)NH—; and
iv) —SCH$_2$CH$_2$CH$_2$CH$_2$CH$_2$C(O)NH—.

A further embodiment of this category relates to linking units having the formula:

—O[CH$_2$)]$_p$NHC(O)— wherein x is from 2 to 6. Examples of this embodiment include:
i) —OCH$_2$CH$_2$NHC(O)—;
ii) —OCH$_2$CH$_2$CH$_2$NHC(O)—;
iii) —OCH$_2$CH$_2$CH$_2$CH$_2$NHC(O)—; and
iv) —OCH$_2$CH$_2$CH$_2$CH$_2$CH$_2$NHC(O)—.

A yet further embodiment of this category relates to linking units having the formula:

—S[CH$_2$)]$_p$C(O)— wherein x is from 2 to 6. Examples of this embodiment include:
i) —SCH$_2$CH$_2$C(O)—;
ii) —SCH$_2$CH$_2$CH$_2$C(O)—;
iii) —SCH$_2$CH$_2$CH$_2$CH$_2$C(O)—; and
iv) —SCH$_2$CH$_2$CH$_2$CH$_2$CH$_2$C(O)—.

A still yet further embodiment of this category relates to linking units having the formula:

—O[CH$_2$)]$_p$C(O)— wherein x is from 2 to 6. Examples of this embodiment include:
i) —OCH$_2$CH$_2$C(O)—;
ii) —OCH$_2$CH$_2$CH$_2$C(O)—;
iii) —OCH$_2$CH$_2$CH$_2$CH$_2$C(O)—; and
iv) —OCH$_2$CH$_2$CH$_2$CH$_2$CH$_2$C(O)—.

A further category of L units relates to linking units having the formula:

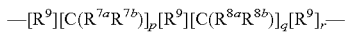

wherein each $R^{7a}$, $R^{7b}$, $R^{8a}$, and $R^{8b}$ is independently hydrogen or methyl, and $R^9$ is chosen from
i) —$NR^6C(O)$—;
ii) —$C(O)NR^6$—;
iii) —$C(O)$—;
iv) —$OC(O)$—;
v) —$C(O)O$—;
vi) —O—; or
vii) —S—;
and the index r is 0 or 1.

One embodiment of this category relates to linking units having the formula:

wherein x is from 2 to 6. Examples of this embodiment include:
i) —$SCH_2CH_2NHC(O)CH_2CH_2$—;
ii) —$SCH_2CH_2CH_2NHC(O)CH_2$—;
iii) —$SCH_2CH_2CH_2CH_2NHC(O)CH_2CH_2$—; and
iv) —$SCH_2CH_2CH_2NHC(O)CH_2CH_2$—.

Another embodiment of this category relates to linking units having the formula:

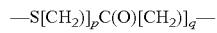

wherein x is from 2 to 6. Examples of this embodiment include:
i) —$SCH_2CH_2C(O)CH_2CH_2$—;
ii) —$SCH_2CH_2CH_2C(O)CH_2$—;
iii) —$SCH_2CH_2CH_2CH_2C(O)CH_2CH_2$—; and
iv) —$SCH_2CH_2CH_2C(O)CH_2CH_2$—.

A further embodiment of this category relates to linking units having the formula:

wherein x is from 2 to 6. Examples of this embodiment include:
i) —$SCH_2CH_2NHC(O)CH_2CH_2$—;
ii) —$SCH_2CH_2CH_2NHC(O)CH_2$—;
iii) —$SCH_2CH_2CH_2CH_2NHC(O)CH_2CH_2$—; and
iv) —$SCH_2CH_2CH_2NHC(O)CH_2CH_2$—.

A yet further embodiment of this category relates to linking units having the formula:

wherein x is from 2 to 6. Examples of this embodiment include:
i) —$SCH_2CH_2NHC(O)CH_2CH_2S$—;
ii) —$SCH_2CH_2CH_2NHC(O)CH_2$—S;
iii) —$SCH_2CH_2CH_2CH_2NHC(O)CH_2CH_2S$—; and
iv) —$SCH_2CH_2CH_2NHC(O)CH_2CH_2S$—.

A yet another embodiment of this category relates to linking units having the formula:

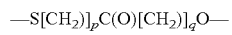

wherein x is from 2 to 6. Examples of this embodiment include:
i) —$SCH_2CH_2C(O)CH_2CH_2O$—;
ii) —$SCH_2CH_2CH_2C(O)CH_2O$—;
iii) —$SCH_2CH_2CH_2CH_2C(O)CH_2CH_2O$—; and
iv) —$SCH_2CH_2CH_2C(O)CH_2CH_2O$—.

A yet still further embodiment of this category relates to linking units having the formula:

wherein x is from 2 to 6. Examples of this embodiment include:
i) —$SCH_2CH_2NHC(O)CH_2CHO_2$—;
ii) —$SCH_2CH_2CH_2NHC(O)CH_2O$—;
iii) —$SCH_2CH_2CH_2CH_2NHC(O)CH_2CH_2O$—; and
iv) —$SCH_2CH_2CH_2NHC(O)CH_2CH_2O$—.

One category of tissue-nonspecific alkaline phosphatase inhibitors relates to pyrazoles having the formula:

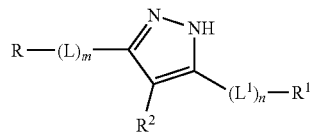

wherein R, $R^1$, $R^2$, L, $L^1$, m, and n are defined herein above.

One embodiment of this category relates to pyrazoles having the formula:

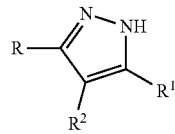

wherein R is substituted or unsubstituted aryl or heteroaryl; $R^1$ is chosen from hydrogen, —$NH_2$, —OH, —$C(O)OCH_3$, or —$C(O)OH$. Non-limiting examples of this embodiment include:

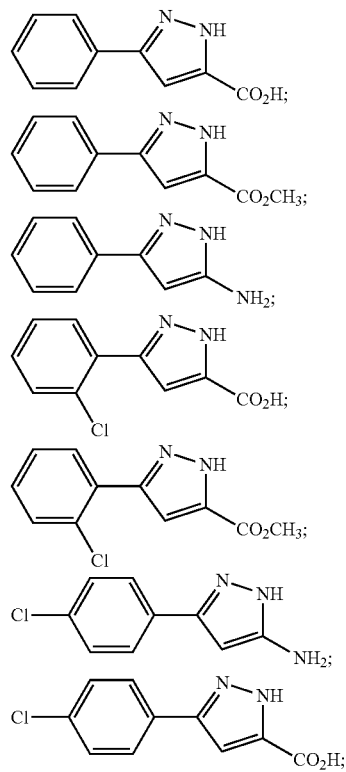

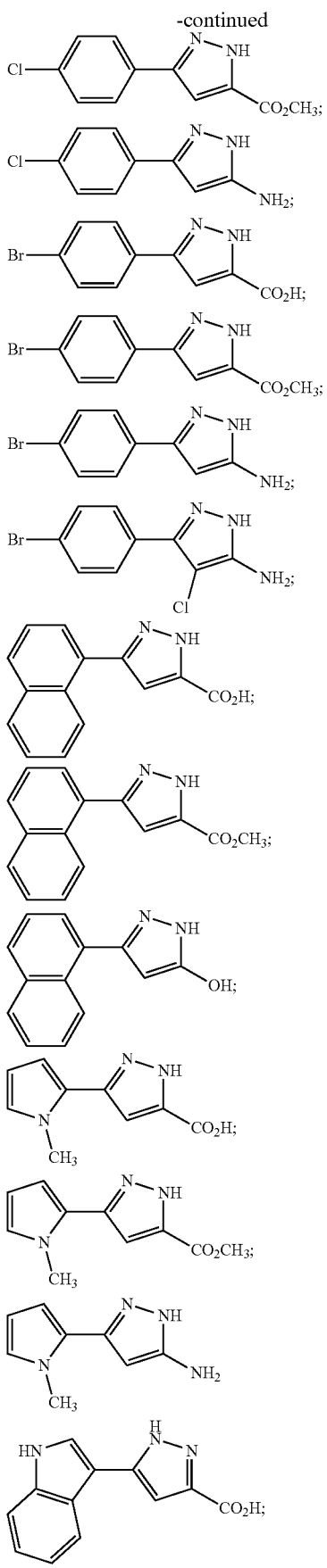

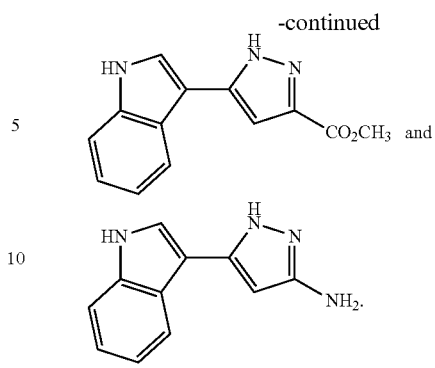

Further non-limiting examples of this embodiment include 3-phenyl-1H-pyrazol-5-ol, 3-(3-chlorophenyl)-1H-pyrazole-5-carboxylic acid, methyl 3-(3-chlorophenyl)-1H-pyrazole-5-carboxylate, 3-(3-chlorophenyl)-1H-pyrazole-5-amine, 3-(3-bromophenyl)-1H-pyrazole-5-carboxylic acid, methyl 3-(3-bromophenyl)-1H-pyrazole-5-carboxylate, 3-(1H-pyrrol-2-yl)-1H-pyrazole-5-carboxylic acid, methyl 3-(1H-pyrrol-2-yl)-1H-pyrazole-5-carboxylate, 3-(1H-pyrrol-2-yl)-1H-pyrazole-5-amine, 3-(1H-furan-2-yl)-1H-pyrazole-5-carboxylic acid, methyl 3-(1H-furan-2-yl)-1H-pyrazole-5-carboxylate, 3-(1H-furan-2-yl)-1H-pyrazole-5-amine, 3-(1H-pyrrol-3-yl)-1H-pyrazole-5-carboxylic acid, methyl 3-(1H-pyrrol-3-yl)-1H-pyrazole-5-carboxylate, 3-(1H-pyrrol-3-yl)-1H-pyrazole-5-amine, 3-(1H-furan-3-yl)-1H-pyrazole-5-carboxylic acid, methyl 3-(1H-furan-3-yl)-1H-pyrazole-5-carboxylate, and 3-(1H-furan-3-yl)-1H-pyrazole-5-amine.

The following table provides exemplary $IC_{50}$ values for various tissue-nonspecific alkaline phosphatase inhibitors according to this embodiment.

TABLE A

| No. | Compound | $IC_{50}$ |
|---|---|---|
| A1 | 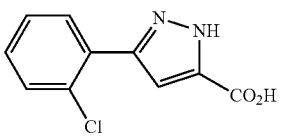 [SMILES: O=C(O)c1cc(-c2ccccc2Cl)n[nH]1]<br>3-(2-chlorophenyl)-1H-pyrazole-5-carboxylic acid | 0.68 |
| A2 | 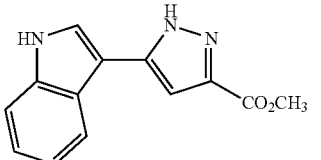<br>methyl 3-(1H-indol-3-yl)-1H-pyrazole-5-carboxylate | 0.81 |
| A3 | 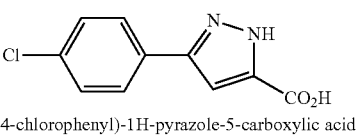<br>3-(4-chlorophenyl)-1H-pyrazole-5-carboxylic acid | 0.95 |
| A4 | 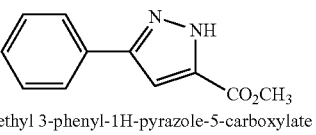<br>methyl 3-phenyl-1H-pyrazole-5-carboxylate | 0.97 |

TABLE A-continued

| No. | Compound | IC$_{50}$ |
|---|---|---|
| A5 | 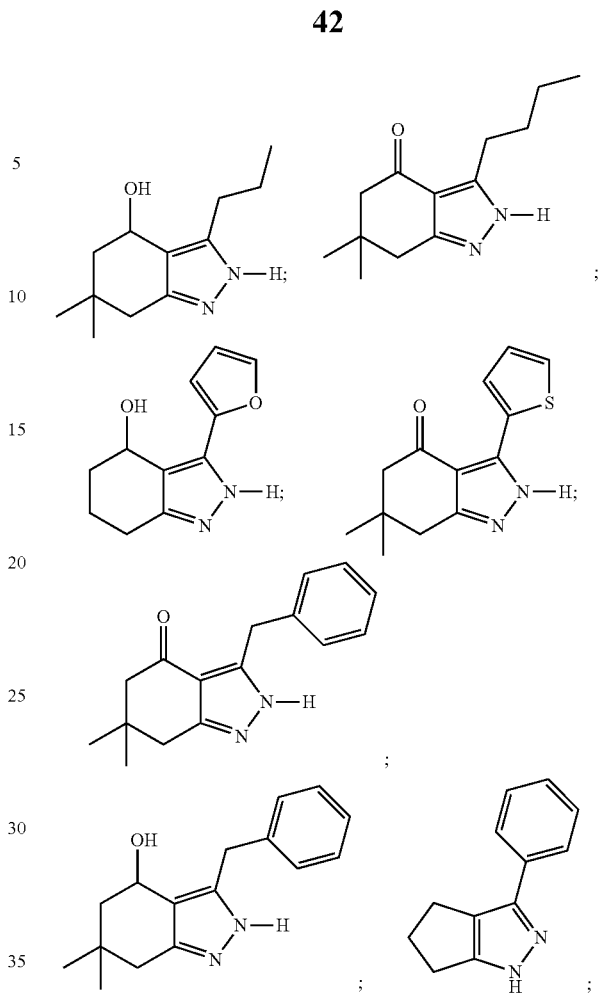 3-(napthalen-1-yl)-1H-pyrazol-5-ol | 3.24 |
| A6 | 3-(4-bromophenyl)-4-chloro-1-H-pyrazol-5-amine | 6.51 |
| A7 | 3-(1-methyl-1H-pyrrol-2-yl)-1H-pyrazole-5-carboxylate | 10.15 |
| A8 | methyl 3-(4-bromophenyl)-1H-pyrazole-5-carboxylate | 0.31 |

Another embodiment of this category relates to pyrazoles having the formula:

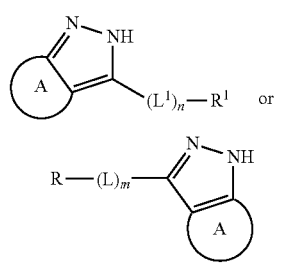

wherein R and R$^2$ are taken together to form ring A comprising one or more 5-member or 6-member substituted or unsubstituted cycloalkyl fused rings, substituted or unsubstituted aryl fused rings, 5-member or 6-member heteroaryl fused rings having one or more atoms chosen from nitrogen, oxygen, and sulfur, or substituted or unsubstituted 5-member, 6-member, or 7-member heterocyclic fused rings having one or more atoms chosen from nitrogen, oxygen, and sulfur.

One iteration of this embodiment relates to compounds wherein ring A is a substituted or unsubstituted cycloalkyl ring and R$^1$, L$^1$ and the index n are the same as defined herein above. Non-limiting examples of this iteration include compounds having the formula:

Another iteration of this embodiment relates to compounds wherein ring A is a substituted or unsubstituted heterocyclic ring and R$^1$, L$^1$ and the index n are the same as defined herein above. Non-limiting examples of this iteration include compounds having the formula:

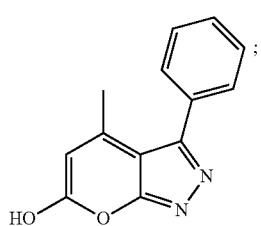

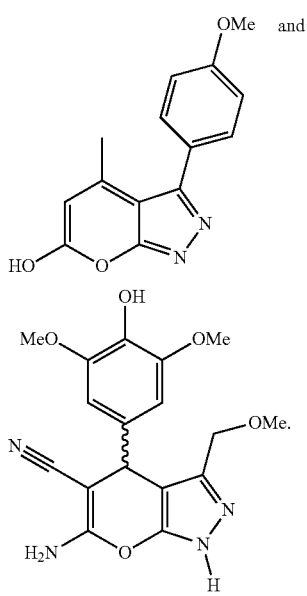

A further iteration of this embodiment relates to compounds wherein ring A is a substituted or unsubstituted aryl ring and $R^1$, $L^1$ and the index n are the same as defined herein above. Non-limiting examples of this iteration include compounds having the formula:

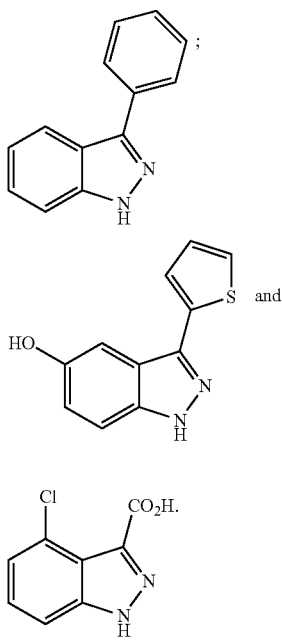

A still further iteration of this embodiment relates to compounds wherein ring A is a combination of a substituted or unsubstituted cycloalkyl ring and a substituted or unsubstituted aryl ring and $R^1$, $L^1$ and the index n are the same as defined herein above. Non-limiting examples of this iteration include compounds having the formula:

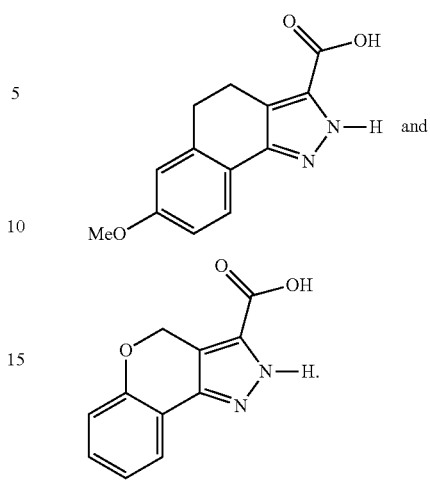

The following table provides exemplary $IC_{50}$ values for various tissue-nonspecific alkaline phosphatase inhibitors according to this embodiment.

TABLE B

| No. | Compound | $IC_{50}$ |
|---|---|---|
| B1 | 3-butyl-6,6-dimethyl-6,7-dihydro-2H-indazol-4(5H)-one | 1.51 |
| B2 | 6,6-dimethyl-3-(thiophen-2-yl)-6,7-dihydro-2H-indazol-4(5H)-one | 3.67 |
| B3 | 3-benzyl-6,6-dimethyl-6,7-dihydro-2H-indazol-4(5H)-one | 0.57 |

TABLE B-continued

| No. | Compound | IC$_{50}$ |
|---|---|---|
| B4 | 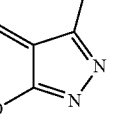  4-methyl-3-phenylpyrano[2,3-c]pyrazol-6-ol | 0.99 |
| B5 | 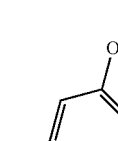  3-(4-methoxyphenyl)-4-methylpyrano[2,3-c]pyrazol-6-ol | 1.35 |
| B6 | 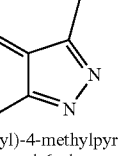  6-amino-4-(4-hydroxy-3,5-dimethoxyphenyl)-3-(methoxymethyl)-1,4-dihydropyrano[2,3-c]pyrazole-5-carbonitrile | 5.25 |
| B7 | 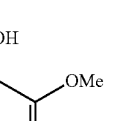  3-phenyl-1,4,5,6-tetrahydrocyclopenta[c]pyrazole | 1.21 |
| B8 | 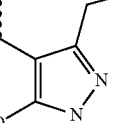  2-(5-methylisoxazol-3-ylamino)-2-oxoethyl 2H-indazole-3-carboxylate | 9.43 |
| B9 | 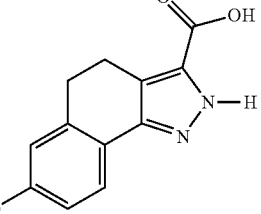  7-methoxy-4,5-dihydro-2H-benzo[g]indazole-3-carboxylic acid | 0.32 |
| B10 | 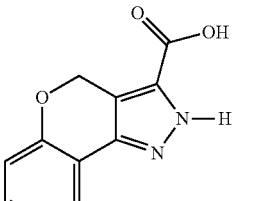  2,4-dihydrochromeno[4,3-c]pyrazole-3-carboxylic acid | 1.35 |
| B11 | 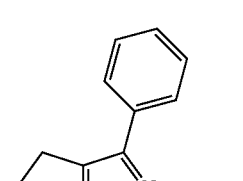  3-phenyl-1,4,5,6-tetrahydrocyclopenta[c]pyrazole | 3.4 |

Another category of tissue-nonspecific alkaline phosphatase inhibitors relates to [1,2,4]triazoles having the formula:

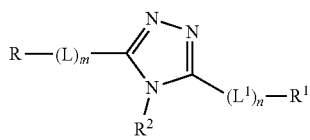

One embodiment of this category relates to compounds having the formula:

wherein R is substituted or unsubstituted phenyl;
R$^1$ is substituted or unsubstituted heteroaryl;
each R$^9$ is independently chosen from:
  i) —NHC(O)—;
  ii) —C(O)NH—;
  iii) —C(O)—;
  iv) —NHC(O)NH—;
  v) —C(O)NHC(O)NH—;
  vi) —NH(=NR$^{10}$NH—; or
  vii) —O—;
the index p is from 1 to 3; the index q is from 1 to 3; and the index r is 1 or 0.

The following are non-limiting examples of this embodiment:

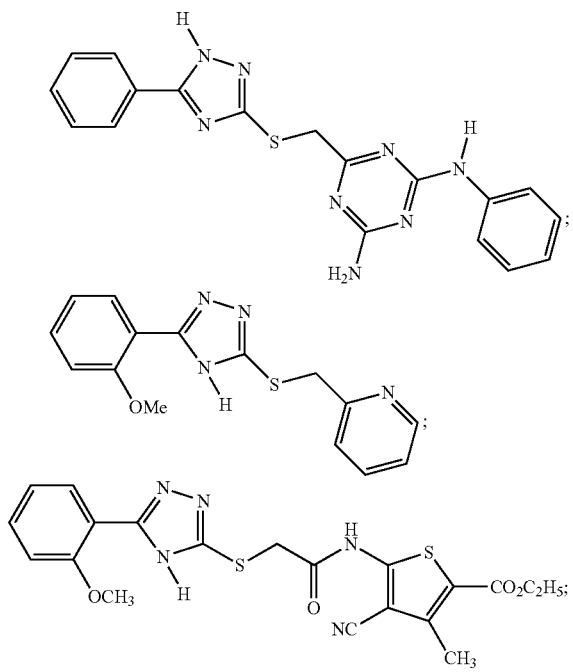

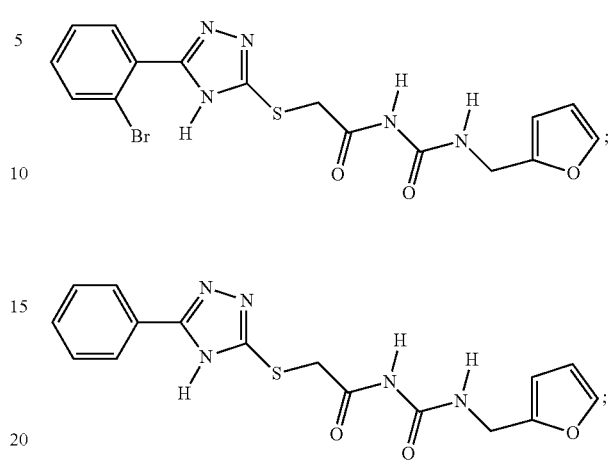

The following table provides exemplary IC$_{50}$ values for various tissue-nonspecific alkaline phosphatase inhibitors according to this embodiment.

TABLE C

| No. | Compound | IC$_{50}$ |
|---|---|---|
| C1 | N$^2$-phenyl-6-[(5-phenyl-1H-1,2,4-triazol-3-ylthio)methyl]-1,3,5-triazine-2,4-diamine | 2.02 |
| C2 | 2-((5-(2-methoxyphenyl)-4H-1,2,4-triazol-3-ylthio)methyl)pyridine | 3.79 |
| C3 | ethyl 4-cyano-5-{2-[5-(2-methoxyphenyl)-4H-1,2,4-triazol-3-ylthio]acetamide}-3-methylthiophene-2-carboxylate | 5.39 |

TABLE C-continued

| No. | Compound | IC$_{50}$ |
|---|---|---|
| C4 | 2-[5-(2-bromophenyl)-4H-1,2,4-triazol-3-ylthio]-N-(furan-2-ylmethylcarbamoyl)acetamide | 2.54 |
| C5 | N-(furan-2-ylmethylcarbamoyl)-2-(5-phenyl-4H-1,2,4-triazol-3-ylthio)acetamide | 1.57 |

Another embodiment of this category relates to compounds having the formula:

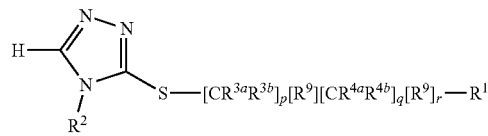

wherein $R^1$ is:
  ix) substituted or unsubstituted aryl; or
  x) substituted or unsubstituted heteroaryl;
$R^2$ is hydrogen or methyl;
each $R^{3a}$, $R^{3b}$, $R^{4a}$, and $R^{4b}$ are each independently chosen from:
  i) hydrogen;
  ii) $C_1$-$C_4$ linear or branched alkyl;
  iii) phenyl;
  iv) hydroxyl; or
  v) cyano;
  vi) or two adjacent $R^{3a}$ units or two adjacent $R^{3b}$ units can be taken together to form a double bond;
each $R^9$ is independently chosen from:
  i) —NHC(O)—;
  ii) —C(O)NH—;
  iii) —C(O)—;
  iv) —NHC(O)NH—;
  v) —C(O)NHC(O)NH—;
  vi) —NH(=NR$^{10}$NH—; or
  vii) —O—;
the index p is from 1 to 3; the index q is from 1 to 3; and the index r is 1 or 0.

The following are non-limiting examples of this embodiment:

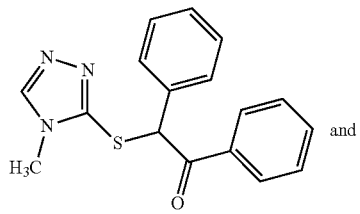
and
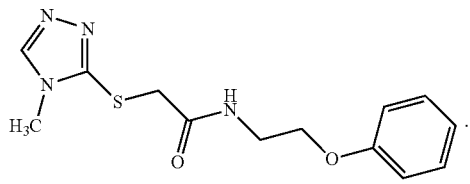

The following table provides exemplary IC$_{50}$ values for various tissue-nonspecific alkaline phosphatase inhibitors according to this embodiment.

TABLE D

| No. | Compound | IC$_{50}$ |
|---|---|---|
| D1 | N$^2$-phenyl-6-[(5-phenyl-1H-1,2,4-triazol-3-ylthio)methyl]-1,3,5-triazine-2,4-diamine | K$_i$ = 5.6 |

TABLE D-continued

| No. | Compound | IC$_{50}$ |
|---|---|---|
| D2 | 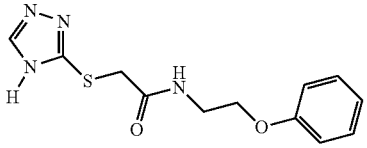 [SMILES: O=C(CSc1nnc[nH]1)NCCOc1ccccc1] 2-((5-(2-methoxyphenyl)-4H-1,2,4-triazol-3-ylthio)methyl)pyridine | K$_i$ = 5.6 |

A yet further category of compounds disclosed herein relates to imidazoles having the formula:

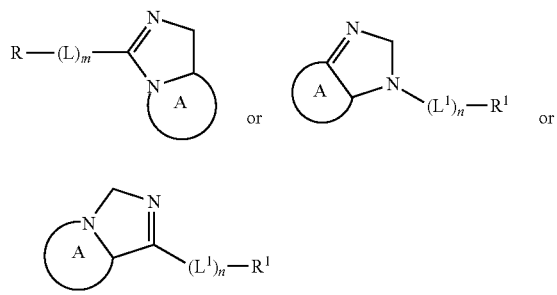

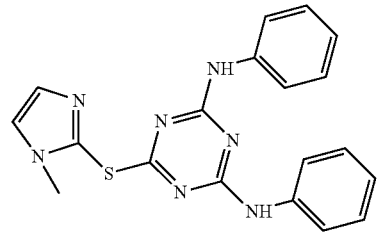

wherein A is a ring comprising one or more cycloalkyl, heterocyclic, or heteroaryl rings and R, R$^1$, L, L$^1$, and the indices m and n are defined herein above.

The following table provides further exemplary IC$_{50}$ values for various tissue-nonspecific alkaline phosphatase inhibitors according to the present disclosure.

TABLE E

| No. | Compound | IC$_{50}$ |
|---|---|---|
| E1 | 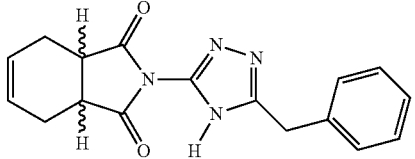 6-(1-methyl-1H-imidazol-2-ylthio)-N$^2$,N$^4$-diphenyl-1,3,5-triazine-2,4-diamine | K$_i$ = 5.6 |
| E2 | 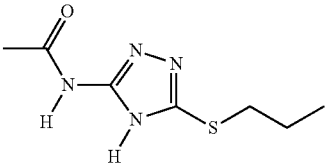 2-(5-benzyl-4H-1,2,4-triazol-3-yl)-3a,4,7,7a-tetrahydro-1H-isoindole-1,3(2H)-dione | 0.33 |
| E3 | 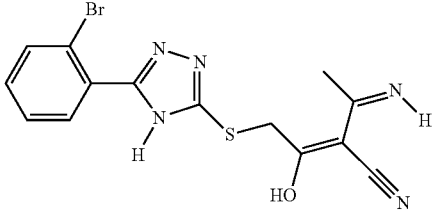 N-(5-(propylthio)-4H-1,2,4-triazol-3-yl)acetamide | 0.68 |
| E4 | 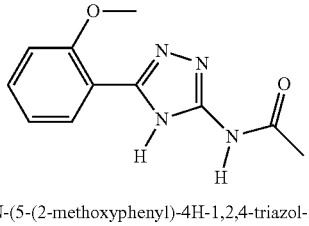 (Z)-4-(5-(2-bromophenyl)-4H-1,2,4-triazol-3-ylthio)-3-hydroxy-2-(1-iminoethyl)but-2-enenitrile | 1.06 |
| E5 | 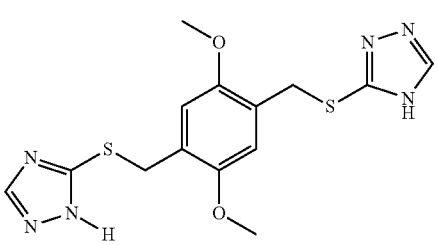 N-(5-(2-methoxyphenyl)-4H-1,2,4-triazol-3-yl)acetamide | 1.99 |
| E6 | 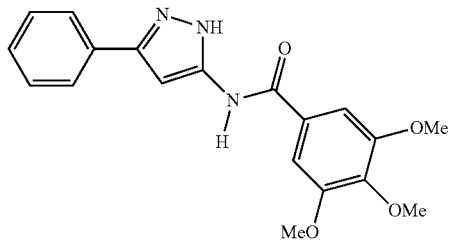 3,3'-(2,5-dimethoxy-1,4-phenylene)-bis(methylene)bis(sulfanediyl)bis(4H-1,2,4-triazole) | 1.99 |
| E7 | 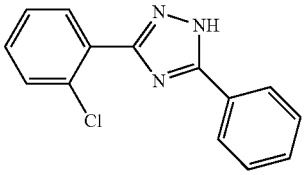 3,4,5-trimethoxy-N-(3-phenyl-1H-pyrazol-5-yl)benzamide | 2.39 |
| E8 | 3-(2-chlorophenyl)-5-phenyl-1H-1,2,4-triazole | 2.47 |

TABLE E-continued

| No. | Compound | IC$_{50}$ |
|---|---|---|
| E9 | 5-(furan-2-yl)-2-(4-methoxyphenyl)-5H-[1,2,4]triazolo[5,1-b][1,3]thiazin-7(6H)-one | 3.82 |
| E10 | (ethyl ester pyrimido-benzimidazole structure) | 3.94 |
| E11 | 5-(allylthio)-3-(4-methoxyphenyl)-1H-1,2,4-triazole | 4.35 |
| E12 | 2-(4H-imidazo[4,5-b]pyridin-2-ylthio)-1-(2,5-dimethoxyphenyl)ethanone | 4.68 |
| E13 | 5-chloro-1-phenyl-1H-benzo[d]imidazol-2-ol | 5.34 |
| E14 | 3-(2-chlorophenyl)-7-methyl-7H-pyrazolo[4,3-e][1,2,4]triazolo[4,3-c]pyrimidine | 5.83 |
| E15 | 2-(4H-imidazo[4,5-b]pyridin-2-ylthio)-1-(4-fluorophenyl)ethanone | 6.26 |
| E16 | 3-((2,6-dimethylphenoxy)methyl)-7-methyl-7H-pyrazolo[4,3-e][1,2,4]triazolo[4,3-c]pyrimidine | 6.89 |
| E17 | 7-(3,4-dimethylphenyl)-3-methyl-7H-pyrrolo[3,2-e][1,2,4]triazolo[4,3-c]pyrimidine | 7.92 |
| E18 | 5-(2-(3,4-dihydroxyphenyl)-2-oxoethylthio)-2-isopropylimidazo[1,2-c]quinazolin-3(2H)-one | 10.28 |
| E19 | (Z)-5-((3-methylthiophen-2-yl)methylene)thiazolo[3,2-b][1,2,4]triazol-6(5H)-one | 11.28 |

TABLE E-continued

| No. | Compound | IC$_{50}$ |
|---|---|---|
| E20 | 7-(3,4-dimethylphenyl)-2-methyl-7H-pyrazolo[4,3-e][1,2,4]triazolo[1,5-c]pyrimidine | 13 |
| E21 | 7-methyl-2-phenethyl-7H-pyrazolo[4,3-e][1,2,4]triazolo[1,5-c]pyrimidine | 16 |
| E22 | | 9.5 |

A still yet further category of tissue-nonspecific alkaline phosphatase inhibitors relates to aryl sulphonamides having the formula:

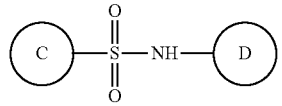

wherein C is a substituted or unsubstituted $C_6$ of $C_{10}$ aryl ring; D is a substituted or unsubstituted $C_5$-$C_9$ heteroaryl ring; wherein further the substitutions are each independently chosen from:
i) halogen;
ii) hydroxy
iii) $C_1$-$C_4$ alkyl;
iv) $C_1$-$C_4$ alkoxy;
v) substituted or unsubstituted heterocyclic;
vi) substituted or unsubstituted heteroaryl;
vii) substituted or unsubstituted aryl;
viii) amino;
ix) mono-$C_1$-$C_4$ alkylamino;
x) di-$C_1$-$C_4$ alkylamino;
xi) nitro; and
xii) cyano.

One embodiment of this category relates to compounds having the formula:

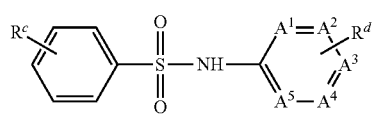

wherein $A^1$, $A^2$, $A^3$, $A^4$, and $A^5$ each independently represent —CH— or —N—; $R^c$ represents from 1 to 5 optionally present substitutions for hydrogen, and $R^d$ represents from 1 to 4 optionally present substitutions for hydrogen. Non-limiting examples of compounds according to this embodiment have the formula:

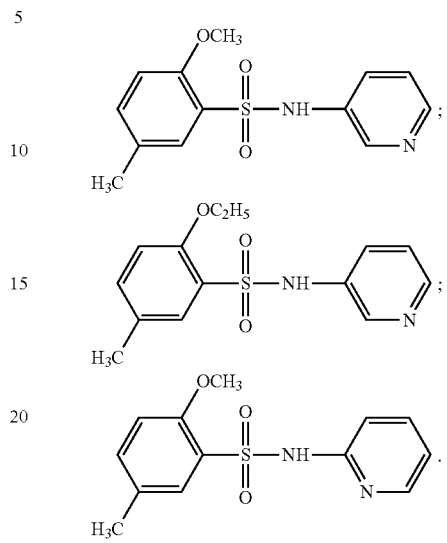

A further embodiment of this category relates to compounds having the formula:

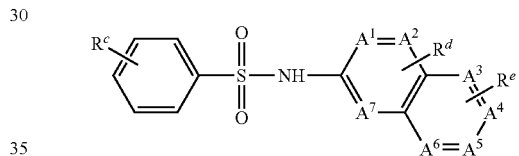

wherein $A^1$, $A^2$, $A^3$, $A^4$, $A^5$, $A^6$, and $A^7$ each independently represent —CH— or —N—; $R^c$ represents from 1 to 5 optionally present substitutions for hydrogen, and $R^d$ and $R^e$ represents from 1 to 4 optionally present substitutions for hydrogen. Non-limiting examples of compounds according to this embodiment include 2-dimethoxy-N-(quinolin-3-yl)benzene-sulfonamide have the formula:

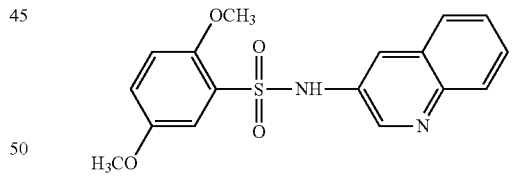

Another embodiment of this category of tissue-nonspecific alkaline phosphatase inhibitors relates to aryl sulphonamides having the formula:

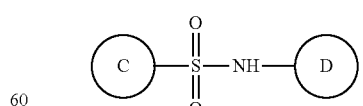

wherein C is a substituted or unsubstituted $C_6$ of $C_{10}$ aryl ring; D is a substituted or unsubstituted aryl ring; wherein further the substitutions are each independently chosen from:
i) halogen;
ii) hydroxy iii) $C_1$-$C_4$ alkyl;

iv) $C_1$-$C_4$ alkoxy;

v) substituted or unsubstituted heterocyclic;

vi) substituted or unsubstituted heteroaryl;

vii) substituted or unsubstituted aryl;

viii) amino;

ix) mono-$C_1$-$C_4$ alkylamino;

x) di-$C_1$-$C_4$ alkylamino;

xi) nitro; and xii) cyano.

A non-limiting example of this embodiment includes N-[3-1H-1,2,4,-triazol-3-ylthio)-4-hydroxyphenyl)-2,5-dimethyoxybenzenesulfonamide having the formula:

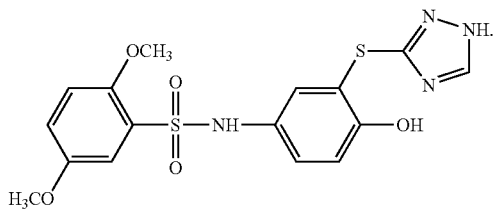 [SMILES: COc1ccc(OC)c(S(=O)(=O)Nc2ccc(O)c(Sc3nc[nH]n3)c2)c1]

The following table provides further exemplary $IC_{50}$ values for various tissue-nonspecific alkaline phosphatase inhibitors according to the present disclosure.

TABLE F

| No. | Compound | $IC_{50}$ |
|---|---|---|
| F1 | 2,5-dimethoxy-N-(quinolin-3-yl)benzene-sulfonamide | 0.15 |
| F2 | 2-methoxy-5-methyl-N-(pyridine-3-yl)benzenesulfonamide | 0.75 |
| F3 | 2-ethoxy-5-methyl-N-(pyridine-3-yl)benzenesulfonamide | 1.93 |

TABLE F-continued

| No. | Compound | $IC_{50}$ |
|---|---|---|
| F4 | N-[(3-1H-1,2,4-triazol-3-ylthio)-4-hydroxyphenyl]-2,5-dimethoxybenzenesulfonamide | 8.45 |

A still further category of tissue-nonspecific alkaline phosphatase inhibitors relates to tethered aryl bisphosphonic acids having the formula:

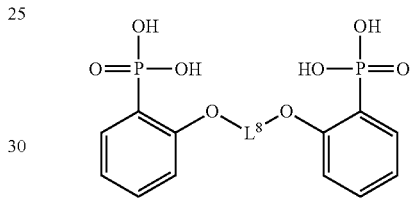

wherein $L^8$ represents a polyalkylene or polyalkyleneoxy linking unit having from 2 to 20 carbon atoms and from 1 to 10 oxygen atoms. Non limiting examples of this category include 2,2'-[2,2'-oxybis(ethane-2,1-diyl)bis(oxy)]bis(2,1-phenylene)diphosphonic acid and 2,2'-(pentane-1,5-diylbis(oxy))bis(2,1-phenylene)diphosphonic acid having the formula:

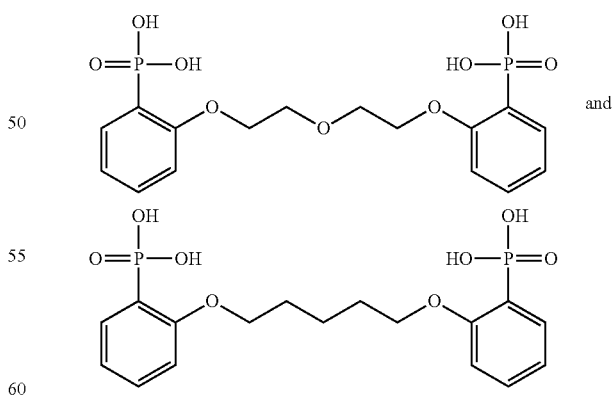

and

The following table provides exemplary $IC_{50}$ values for various tissue-nonspecific alkaline phosphatase inhibitors according to this category.

TABLE G

| No. | Compound | IC$_{50}$ |
|---|---|---|
| G1 | 2,2'-[2,2'-oxybis(ethane-2,1-diyl)bis(oxy)]bis(2,1-phenylene)diphosphonic acid | 1.66 |
| G2 | 2,2'-(pentane-1,5-diylbis(oxy))bis(2,1-phenylene)disphosphonic acid | 2.05 |

A still yet further category of tissue-nonspecific alkaline phosphatase inhibitors relates to compounds, for example, 4-{2-[2-(3,4-dihydroxyphenyl)-2-oxoethylthio]-4-oxo-quinazolin-3(4H)-yl}-N-[(tetrahydrofuran-2-yl)methyl]butanamide having the formula:

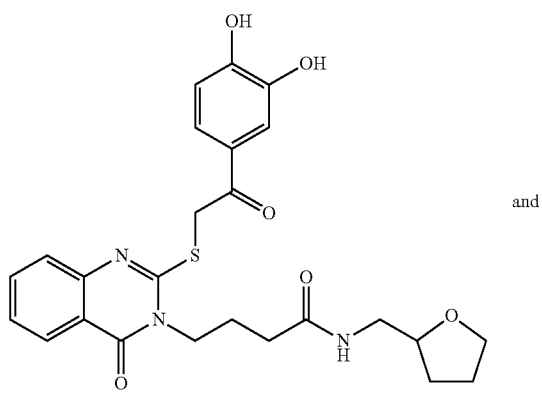 [SMILES: O=C(CCCn1c(SCC(=O)c2ccc(O)c(O)c2)nc2ccccc2c1=O)NCC1CCCO1]

and (E)-2-cyano-3-(3,4-dihydroxyphenyl)-N-(3-phenylpropyl)acrylamide having the formula:

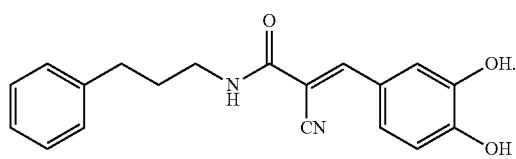 [SMILES: N#C/C(=C\c1ccc(O)c(O)c1)C(=O)NCCCc1ccccc1]

The following table provides exemplary IC$_{50}$ values for various tissue-nonspecific alkaline phosphatase inhibitors according to this category.

TABLE H

| No. | Compound | IC$_{50}$ |
|---|---|---|
| H1 | 4-{2-[2-(3,4-dihydroxyphenyl)-2-oxoethylthio]-4-oxoquinazolin-3(4H)-yl}-N-[(tetrahydrofuran-2-yl)methyl]butanamide | 4.66 |
| H2 | (E)-2-cyano-3-(3,4-dihydroxyphenyl)-N-(3-phenylpropyl)acrylamide | 5.16 |

Disclosed herein are compositions comprising the disclosed tissue-nonspecific alkaline phosphatase inhibitors, as such, the compositions comprise: an effective amount of one or more tissue nonspecific alkaline phosphatase inhibitors; and a pharmaceutically accepted carrier, excipient, and/or diluent.

2. Dosage Forms
i. Prodrugs

Prodrugs, as disclosed herein, can be prepared methods known in the art (e.g., by modifying a functional group present in a compound or drug in such a way that the modifications can be cleaved, either in routine manipulation in vivo, to the parent compound). Prodrugs include compounds disclosed herein wherein the carbonyl, carboxylic acid, hydroxy or amino group can be bonded to any group that, when the prodrug is administered to a subject, cleaves to form a free carbonyl, carboxylic acid, hydroxy or amino group. Examples of pro-drugs include, but are not limited to, compounds comprising an acetate, formate and/or benzoate derivatives of an alcohol and an amine functional group.

Pro-drugs include known hydroxyl and amino derivatives, such as, for example, esters prepared by reaction of the parent hydroxyl compound with a suitable carboxylic acid, or amides prepared by reaction of the parent amino compound with a suitable carboxylic acid. Simple aliphatic or aromatic esters derived from hydroxyl groups pendent on or in the compounds employed are suitable prodrugs. In some aspects, it can be suitable to prepare double ester type prodrugs such as (acyloxy) alkyl esters or ((alkoxycarbonyl)oxy)alkyl esters. Specific suitable esters as pro-drugs comprise methyl, ethyl, propyl, isopropyl, n-butyl, isobutyl, tert-butyl, morpholinoethyl, and the like.

A review of metabolic reactions and enzyme reactions involved in the hydrolysis of drugs and prodrugs can be found in "Hydrolysis in Drug and Pro-drug Metabolism: Chemistry, Biochemistry, and Enzymology" (2003), which is hereby incorporated into this specification by reference. Additional references useful in designing prodrugs, as disclosed herein, include, e.g., "Biological Approaches to the Controlled Delivery of Drugs" (1988); "Design of Biobiological agent Properties through Pro-drugs and Analogs" (1977); "Pro-drugs: Topical and Ocular Drug Delivery" (1992); "Enzyme-Pro-drug Strategies for Cancer Therapy" (1999); "Design of Pro-drugs" (1986); "Textbook of Drug Design and Development" (1991); "Conversion of Non-Toxic Pro-drugs to Active, Anti-Neoplastic Drugs Selectively in Breast Cancer Metastases" (2000); and "Marine lipids for prodrugs, of compounds and other biological agent applications" (2000).

Prodrugs, as disclosed herein, can comprise any suitable functional group that can be chemically or metabolically cleaved by solvolysis or under physiological conditions to provide the biologically active compound. Suitable functional groups include, e.g., carboxylic esters, amides, and thioesters. Depending on the reactive functional group(s) of the biologically active compound, a corresponding functional group of a suitable linker precursor can be selected to provide, e.g., an ester linkage, thioester linkage, or amide linkage in the prodrug.

3. Carriers

The disclosed TNAP inhibitors can be combined, conjugated or coupled with or to carriers and other compositions to aid administration, delivery or other aspects of the inhibitors and their use. For convenience, such composition will be referred to herein as carriers. Carriers can, for example, be a small molecule, pharmaceutical drug, fatty acid, detectable marker, conjugating tag, nanoparticle, or enzyme.

The disclosed compositions can be used therapeutically in combination with a pharmaceutically acceptable carrier. By "pharmaceutically acceptable" is meant a material that is not biologically or otherwise undesirable, i.e., the material can be administered to a subject, along with the composition, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds can be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The materials may be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

The carrier molecule can be covalently linked to the disclosed inhibitors. The carrier molecule can be linked to the amino terminal end of the disclosed peptides. The carrier molecule can be linked to the carboxy terminal end of the disclosed peptides. The carrier molecule can be linked to an amino acid within the disclosed peptides. The herein provided compositions can further comprise a linker connecting the carrier molecule and disclosed inhibitors. The disclosed inhibitors can also be conjugated to a coating molecule such as bovine serum albumin (BSA) (see Tkachenko et al., (2003) J Am Chem Soc, 125, 4700-4701) that can be used to coat microparticles, nanoparticles of nanoshells with the inhibitors.

Protein crosslinkers that can be used to crosslink the carrier molecule to the inhibitors, such as the disclosed peptides, are known in the art and are defined based on utility and structure and include DSS (Disuccinimidylsuberate), DSP (Dithiobis(succinimidylpropionate)), DTSSP (3,3'-Dithiobis (sulfosuccinimidylpropionate)), SULFO BSOCOES (Bis[2-(sulfosuccinimdooxycarbonyloxy)ethyl]sulfone), BSOCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio) propionamido]butane), BSSS (Bis(sulfosuccinimdyl) suberate), SMPB (Succinimdyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl)aminobenzoate), SULFO SIAB (N-Sulfosuccinimidyl(4-iodoacetyl)aminobenzoate), SMCC (Succinimidyl-4-(N-maleimidomethyl)cyclohexane-1-carboxylate), SULFO SMCC (Sulfosuccinimidyl-4-(N-maleimidomethyl)cyclohexane-1-carboxylate), NHS LC SPDP (Succinimidyl-6-[3-(2-pyridyldithio) propionamido) hexanoate), SULFO NHS LC SPDP (Sulfosuccinimidyl-6-[3-(2-pyridyldithio) propionamido) hexanoate), SPDP (N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl)cyclohexane-1-carboxylic acid hydrazide hydrochloride), MBH (m-Maleimidobenzoic acid hydrazidehydrochloride), SULFO EMCS(N-(epsilon-Maleimidocaproyloxy) sulfosuccinimide), EMCS(N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent) (Methyl-p-hydroxybenzimidate hydrochloride, 98%), DMA (Dimethyladipimidate hydrochloride).

i. Nanoparticles, Microparticles, and Microbubbles

The term "nanoparticle" refers to a nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, fullerene-like materials, inorganic nanotubes, dendrimers (such as with covalently attached metal chelates), nanofibers, nanohoms, nano-onions, nanorods, nanoropes and quantum dots. A nanoparticle can produce a detectable signal, for example, through absorption and/or emission of photons (including radio frequency and visible photons) and plasmon resonance.

Microspheres (or microbubbles) can also be used with the methods disclosed herein. Microspheres containing chromophores have been utilized in an extensive variety of applications, including photonic crystals, biological labeling, and flow visualization in microfluidic channels. See, for example, Y. Lin, et al., Appl. Phys Lett. 2002, 81, 3134; D. Wang, et al., Chem. Mater. 2003, 15, 2724; X. Gao, et al., J. Biomed. Opt. 2002, 7, 532; M. Han, et al., Nature Biotechnology. 2001, 19, 631; V. M. Pai, et al., Mag. & Magnetic Mater. 1999, 194, 262, each of which is incorporated by reference in its entirety. Both the photostability of the chromophores and the monodispersity of the microspheres can be important.

Nanoparticles, such as, for example, silica nanoparticles, metal nanoparticles, metal oxide nanoparticles, or semiconductor nanocrystals can be incorporated into microspheres. The optical, magnetic, and electronic properties of the nanoparticles can allow them to be observed while associated with the microspheres and can allow the microspheres to be identified and spatially monitored. For example, the high photostability, good fluorescence efficiency and wide emission tunability of colloidally synthesized semiconductor nanocrystals can make them an excellent choice of chromophore. Unlike organic dyes, nanocrystals that emit different colors (i.e. different wavelengths) can be excited simultaneously with a single light source. Colloidally synthesized semiconductor nanocrystals (such as, for example, core-shell CdSe/ZnS and CdS/ZnS nanocrystals) can be incorporated into microspheres. The microspheres can be monodisperse silica microspheres.

The nanoparticle can be a metal nanoparticle, a metal oxide nanoparticle, or a semiconductor nanocrystal. The metal of the metal nanoparticle or the metal oxide nanoparticle can include titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, scandium, yttrium, lanthanum, a lanthanide series or actinide series element (e.g., cerium, praseodymium, neodymium, promethium, samarium, europium, gadolinium, terbium, dysprosium, holmium, erbium, thulium, ytterbium, lutetium, thorium, protactinium, and uranium), boron, aluminum, gallium, indium, thallium, silicon, germanium, tin, lead, antimony, bismuth, polonium, magnesium, calcium, strontium, and barium. In certain embodiments, the metal can be iron, ruthenium, cobalt, rhodium, nickel, palladium, platinum, silver, gold, cerium or samarium. The metal oxide can be an oxide of any of these materials or combination of materials. For example, the metal can be gold, or the metal oxide can be an iron oxide, a cobalt oxide, a zinc oxide, a cerium oxide, or a titanium oxide. Preparation of metal and metal oxide nanoparticles is described, for example, in U.S. Pat. Nos. 5,897,945 and 6,759,199, each of which is incorporated by reference in its entirety.

For example, a TNAP inhibtor can be immobilized on silica nanoparticles (SNPs). SNPs have been widely used for biosensing and catalytic applications owing to their favorable surface area-to-volume ratio, straightforward manufacture and the possibility of attaching fluorescent labels, magnetic nanoparticles (Yang, H. H. et al. 2005) and semiconducting nanocrystals (Lin, Y. W., et al. 2006).

The nanoparticle can also be, for example, a heat generating nanoshell. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells.

Targeting molecules can be attached to the disclosed compositions and/or carriers. For example, the targeting molecules can be antibodies or fragments thereof, ligands for specific receptors, or other proteins specifically binding to the surface of the cells to be targeted.

ii. Liposomes "Liposome" as the term is used herein refers to a structure comprising an outer lipid bi- or multi-layer membrane surrounding an internal aqueous space. Liposomes can be used to package any biologically active agent for delivery to cells.

Materials and procedures for forming liposomes are well-known to those skilled in the art. Upon dispersion in an appropriate medium, a wide variety of phospholipids swell, hydrate and form multilamellar concentric bilayer vesicles with layers of aqueous media separating the lipid bilayers. These systems are referred to as multilamellar liposomes or multilamellar lipid vesicles ("MLVs") and have diameters within the range of 10 nm to 100 µm. These MLVs were first described by Bangham, et al., J. Mol. Biol. 13:238-252 (1965). In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically active materials is then added to the film. Large MLVs are produced upon agitation. When smaller MLVs are desired, the larger vesicles are subjected to sonication, sequential filtration through filters with decreasing pore size or reduced by other forms of mechanical shearing. There are also techniques by which MLVs can be reduced both in size and in number of lamellae, for example, by pressurized extrusion (Barenholz, et al., FEBS Lett. 99:210-214 (1979)).

Liposomes can also take the form of unilamnellar vesicles, which are prepared by more extensive sonication of MLVs, and consist of a single spherical lipid bilayer surrounding an aqueous solution. Unilamellar vesicles ("ULVs") can be small, having diameters within the range of 20 to 200 nm, while larger ULVs can have diameters within the range of 200 nm to 2 µm. There are several well-known techniques for making unilamellar vesicles. In Papahadjopoulos, et al., Biochim et Biophys Acta 135:624-238 (1968), sonication of an aqueous dispersion of phospholipids produces small ULVs having a lipid bilayer surrounding an aqueous solution. Schneider, U.S. Pat. No. 4,089,801 describes the formation of liposome precursors by ultrasonication, followed by the addition of an aqueous medium containing amphiphilic compounds and centrifugation to form a biomolecular lipid layer system.

Small ULVs can also be prepared by the ethanol injection technique described by Batzri, et al., Biochim et Biophys Acta 298:1015-1019 (1973) and the ether injection technique of Deamer, et al., Biochim et Biophys Acta 443:629-634 (1976). These methods involve the rapid injection of an organic solution of lipids into a buffer solution, which results in the rapid formation of unilamellar liposomes. Another technique for making ULVs is taught by Weder, et al. in "Liposome Technology", ed. G. Gregoriadis, CRC Press Inc., Boca Raton, Fla., Vol. I, Chapter 7, pg. 79-107 (1984). This detergent removal method involves solubilizing the lipids and additives with detergents by agitation or sonication to produce the desired vesicles.

Papahadjopoulos, et al., U.S. Pat. No. 4,235,871, describes the preparation of large ULVs by a reverse phase evaporation technique that involves the formation of a water-in-oil emulsion of lipids in an organic solvent and the drug to be encapsulated in an aqueous buffer solution. The organic solvent is removed under pressure to yield a mixture which, upon agitation or dispersion in an aqueous media, is converted to large ULVs. Suzuki et al., U.S. Pat. No. 4,016,100, describes another method of encapsulating agents in unilamellar vesicles by freezing/thawing an aqueous phospholipid dispersion of the agent and lipids.

In addition to the MLVs and ULVs, liposomes can also be multivesicular. Described in Kim, et al., Biochim et Biophys Acta 728:339-348 (1983), these multivesicular liposomes are spherical and contain internal granular structures. The outer membrane is a lipid bilayer and the internal region contains small compartments separated by bilayer septum. Still yet another type of liposomes are oligolamellar vesicles ("OLVs"), which have a large center compartment surrounded by several peripheral lipid layers. These vesicles, having a diameter of 2-15 µm, are described in Callo, et al., Cryobiology 22(3):251-267 (1985).

Mezei, et al., U.S. Pat. Nos. 4,485,054 and 4,761,288 also describe methods of preparing lipid vesicles. More recently, Hsu, U.S. Pat. No. 5,653,996 describes a method of preparing liposomes utilizing aerosolization and Yiournas, et al., U.S. Pat. No. 5,013,497 describes a method for preparing liposomes utilizing a high velocity-shear mixing chamber. Methods are also described that use specific starting materials to produce ULVs (Wallach, et al., U.S. Pat. No. 4,853,228) or OLVs (Wallach, U.S. Pat. Nos. 5,474,848 and 5,628,936).

A comprehensive review of all the aforementioned lipid vesicles and methods for their preparation are described in "Liposome Technology", ed. G. Gregoriadis, CRC Press Inc., Boca Raton, Fla., Vol. I, II & III (1984). This and the aforementioned references describing various lipid vesicles suitable for use in the invention are incorporated herein by reference.

Fatty acids (i.e., lipids) that can be conjugated to the provided compositions include those that allow the efficient incorporation of the proprotein convertase inhibitors into liposomes. Generally, the fatty acid is a polar lipid. Thus, the fatty acid can be a phospholipid The provided compositions can comprise either natural or synthetic phospholipid. The phospholipids can be selected from phospholipids containing saturated or unsaturated mono or disubstituted fatty acids and combinations thereof. These phospholipids can be dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. The phospholipids can also be synthetic. Synthetic phospholipids are readily available commercially from various sources, such as AVANTI Polar Lipids (Albaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18 or C20 chains length in either or both the PS or PC. Synthetic phospholipids can have dioleoyl (18:1)-PS; palmitoyl (16:0)-oleoyl (18:1)-PS, dimyristoyl (14:0)-PS; dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents. Thus, as an example, the provided compositions can comprise palmitoyl 16:0.

iii. In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

B. Methods

The TNAP inhibitors disclosed herein can be used to treat or prevent vascular calcification. Thus, disclosed herein is a method for treating or preventing vascular calcification in a subject, comprising administering to the subject a TNAP inhibitor disclosed herein.

1. Vascular Calcification

Vascular calcification, a well-recognized and common complication of chronic kidney disease (CKD), increases the risk of cardiovascular morbidity and mortality (Giachelli, C. J. Am. Soc. Nephrol. 15: 2959-64, 2004; Raggi, P. et al. J. Am. Coll. Cardiol. 39: 695-701, 2002). While the causes of vascular calcification in CKD remain to be elucidated, associated risk factors include age, gender, hypertension, time on dialysis, diabetes and glucose intolerance, obesity, and cigarette smoking (Zoccali C. Nephrol. Dial. Transplant 15: 454-7, 2000). These conventional risk factors, however, do not adequately explain the high mortality rates from cardiovascular causes in the patient population. Recent observations suggest that certain abnormalities in calcium and phosphorus metabolism, resulting in a raised serum calcium-phosphorus product (Ca.times.P) contribute to the development of arterial calcification, and possibly to cardiovascular disease, in patients with end-stage renal disease (Goodman, W. et al. N. Engl. J. Med. 342: 1478-83, 2000; Guerin, A. et al. Nephrol. Dial. Transplant 15:1014-21, 2000; Vattikuti, R. & Towler, D. Am. J. Physiol. Endocrinol. Metab. 286: E686-96, 2004).

Another hallmark of advanced CKD is secondary hyperparathyroidism (HPT), characterized by elevated parathyroid hormone (PTH) levels and disordered mineral metabolism. The elevations in calcium, phosphorus, and Ca.times.P observed in patients with secondary HPT have been associated with an increased risk of vascular calcification (Chertow, G. et al. Kidney Int. 62: 245-52, 2002; Goodman, W. et al. N. Engl. J. Med. 342: 1478-83, 2000; Raggi, P. et al. J. Am. Coll. Cardiol. 39: 695-701, 2002). Commonly used therapeutic interventions for secondary HPT, such as calcium-based phosphate binders and doses of active vitamin D sterols can result in hypercalcemia and hyperphosphatemia (Chertow, G. et al. Kidney Int. 62: 245-52, 2002; Tan, A. et al. Kidney Int 51: 317-23, 1997; Gallieni, M. et al. Kidney Int 42: 1191-8, 1992), which are associated with the development or exacerbation of vascular calcification.

Vascular calcification is an important and potentially serious complication of chronic renal failure. Two distinct patterns of vascular calcification have been identified (Proudfoot, D & Shanahan, C. Herz 26: 245-51, 2001), and it is common for both types to be present in uremic patients (Chen, N. & Moe, S. Semin Nephrol 24: 61-8, 2004). The first, medial calcification, occurs in the media of the vessel in conjunction with a phenotypic transformation of smooth muscle cells into osteoblast-like cells, while the other, atherogenesis, is associated with lipid-laden macrophages and intimal hyperplasia.

Medial wall calcification can develop in relatively young persons with chronic renal failure, and it is common in patients with diabetes mellitus even in the absence of renal disease. The presence of calcium in the medial wall of arteries distinguishes this type of vascular calcification from that associated with atherosclerosis (Schinke T. & Karsenty G. Nephrol Dial Transplant 15: 1272-4, 2000). Atherosclerotic vascular calcification occurs in atheromatous plaques along the intimal layer of arteries (Farzaneh-Far A. JAMA 284: 1515-6, 2000). Calcification is usually greatest in large, well-developed lesions, and it increases with age (Wexler L. et al. Circulation 94: 1175-92, 1996; Rumberger J. et al. Mayo Clin Proc 1999; 74: 243-52). The extent of arterial calcification in patients with atherosclerosis generally corresponds to severity of disease. Unlike medial wall calcification, atherosclerotic vascular lesions, whether or not they contain calcium, impinge upon the arterial lumen and compromise blood flow. The localized deposition of calcium within atherosclerotic plaques may happen because of inflammation due to oxidized lipids and other oxidative stresses and infiltration by monocytes and macrophages (Berliner J. et al. Circulation 91: 2488-96, 1995).

Some patients with end-stage renal disease develop a severe form of occlusive arterial disease called calciphylaxis or calcific uremic arteriolopathy. This syndrome is characterized by extensive calcium deposition in small arteries (Gipstein R. et al. Arch Intern Med 136: 1273-80, 1976; Richens G. et al. J Am Acad. Dermatol. 6: 537-9, 1982). In patients with this disease, arterial calcification and vascular occlusion lead to tissue ischemia and necrosis. Involvement of peripheral vessels can cause ulceration of the skin of the lower legs or gangrene of the digits of the feet or hands. Ischemia and necrosis of the skin and subcutaneous adipose tissue of the abdominal wall, thighs and/or buttocks are features of a proximal form of calcific uremic arteriolopathy (Budisavljevic M. et al. J Am Soc Nephrol. 7: 978-82, 1996; Ruggian J. et al. Am. J. Kidney Dis. 28: 409-14, 1996).

This syndrome occurs more frequently in obese individuals, and women are affected more often than men for reasons that remain unclear (Goodman W. J. Nephrol. 15(6): S82-S85, 2002).

Current therapies to normalize serum mineral levels or to decrease, inhibit, or prevent calcification of vascular tissues or implants are of limited efficacy and cause unacceptable side effects. Therefore, there exists a need for an effective method of inhibiting and preventing vascular calcification.

"Vascular calcification," as used herein, means formation, growth or deposition of extracellular matrix hydroxyapatite (calcium phosphate) crystal deposits in blood vessels. Vascular calcification encompasses coronary, valvular, aortic, and other blood vessel calcification. The term includes atherosclerotic and medial wall calcification.

"Atherosclerotic calcification" means vascular calcification occurring in atheromatous plaques along the intimal layer of arteries.

"Medial calcification," "medial wall calcification," or "Monckeberg's sclerosis," as used herein, means calcification characterized by the presence of calcium in the medial wall of arteries.

2. Assessment of Vascular Calcification

Methods of detecting and measuring vascular calcification are well known in the art. In some aspects, methods of measuring calcification include direct methods of detecting and measuring extent of calcium-phosphorus depositions in blood vessels.

In some aspects, direct methods of measuring vascular calcification comprise in vivo imaging methods such as plain film roentgenography, coronary arteriography; fluoroscopy, including digital subtraction fluoroscopy; cinefluorography; conventional, helical, and electron beam computed tomography; intravascular ultrasound (IVUS); magnetic resonance imaging; and transthoracic and transesophageal echocardiography. Persons skilled in the art most commonly use fluoroscopy and EBCT to detect calcification noninvasively. Coronary interventionalists use cinefluorography and IVUS to evaluate calcification in specific lesions before angioplasty.

In some aspects, vascular calcification can be detected by plain film roentgenography. The advantage of this method is availability of the film and the low cost of the method, however, the disadvantage is its low sensitivity (Kelley M. & Newell J. Cardiol Clin. 1: 575-595, 1983).

In some aspects, fluoroscopy can be used to detect calcification in coronary arteries. Although fluoroscopy can detect moderate to large calcifications, its ability to identify small calcific deposits is low (Loecker et al. J. Am. Coll. Cardiol. 19: 1167-1172, 1992). Fluoroscopy is widely available in both inpatient and outpatient settings and is relatively inexpensive.

In some aspects, vascular detection can be detected by conventional computed tomography (CT). Because calcium attenuates the x-ray beam, computed tomography (CT) is extremely sensitive in detecting vascular calcification. While conventional CT appears to have better capability than fluoroscopy to detect coronary artery calcification, its limitations are slow scan times resulting in motion artifacts, volume averaging, breathing misregistration, and inability to quantify amount of plaque (Wexler et al. Circulation 94: 1175-1192, 1996).

In some aspects, calcification can be detected by helical or spiral computer tomography, which has considerably faster scan times than conventional CT. Overlapping sections also improve calcium detection. Coronary calcium imaging by helical CT has a sensitivity of 91% and a specificity of 52% when compared with angiographically significant coronary obstructive disease (Shemesh et al. Radiology 197: 779-783, 1995). Double-helix CT scanners appear to be more sensitive than single-helix scanners in detection of coronary calcification because of their higher resolution and thinner slice capabilities.

In some aspects, Electron Beam Computed Tomography (EBCT) can be used for detection of vascular calcification. EBCT uses an electron gun and a stationary tungsten "target" rather than a standard x-ray tube to generate x-rays, permitting very rapid scanning times. Originally referred to as cine or ultrafast CT, the term EBCT is now used to distinguish it from standard CT scans because modern spiral scanners are also achieving subsecond scanning times. For purposes of detecting coronary calcium, EBCT images are obtained in 100 ms with a scan slice thickness of 3 mm. Thirty to 40 adjacent axial scans are obtained by table incrementation. The scans, which are usually acquired during one or two separate breath-holding sequences, are triggered by the electrocardiographic signal at 80% of the RR interval, near the end of diastole and before atrial contraction, to minimize the effect of cardiac motion. The rapid image acquisition time virtually eliminates motion artifact related to cardiac contraction. The unopacified coronary arteries are easily identified by EBCT because the lower CT density of periarterial fat produces marked contrast to blood in the coronary arteries, while the mural calcium is evident because of its high CT density relative to blood. Additionally, the scanner software allows quantification of calcium area and density. An arbitrary scoring system has been devised based on the x-ray attenuation coefficient, or CT number measured in Hounsfield units, and the area of calcified deposits (Agatston et al. J. Am. Coll. Cardiol. 15:827-832, 1990). A screening study for coronary calcium can be completed within 10 or 15 minutes, requiring only a few seconds of scanning time. Electron beam CT scanners are more expensive than conventional or spiral CT scanners and are available in relatively fewer sites.

In some aspects, intravascular ultrasound (IVUS) can be used for detecting vascular calcification, in particular, coronary atherosclerosis (Waller et al. Circulation 85: 2305-2310, 1992). By using transducers with rotating reflectors mounted on the tips of catheters, it is possible to obtain cross-sectional images of the coronary arteries during cardiac catheterization. The sonograms provide information not only about the lumen of the artery but also about the thickness and tissue characteristics of the arterial wall. Calcification is seen as a hyperechoic area with shadowing: fibrotic noncalcified plaques are seen as hyperechoic areas without shadowing (Honye et al. Trends Cardiovasc Med. 1: 305-311, 1991). The disadvantages in use of IVUS, as opposed to other imaging modalities, are that it is invasive and currently performed only in conjunction with selective coronary angiography, and it visualizes only a limited portion of the coronary tree. Although invasive, the technique is clinically important because it can show atherosclerotic involvement in patients with normal findings on coronary arteriograms and helps define the morphological characteristics of stenotic lesions before balloon angioplasty and selection of atherectomy devices (Tuzcu et al. J. Am. Coll. Cardiol. 27: 832-838, 1996).

In some aspects, vascular calcification can be measured by magnetic resonance imaging (MRI). In some aspects, vascular calcification can be measured by transthoracic (surface) echocardiography, which is particularly sensitive to detection of mitral and aortic valvular calcification.

In some aspects, vascular calcification can be assessed ex vivo by Van Kossa method. This method relies upon the principle that silver ions can be displaced from solution by carbonate or phosphate ions due to their respective positions in the electrochemical series. The argentaffin reaction is photochemical in nature and the activation energy is supplied from strong visible or ultra-violet light. Since the demonstrable forms of tissue carbonate or phosphate ions are invariably associated with calcium ions the method can be considered as demonstrating sites of tissue calcium deposition.

Other methods of direct measuring calcification may include, but not limited to, immunofluorescent staining and densitometry. In another aspect, methods of assessing vascular calcification include methods of measuring determinants and/or risk factors of vascular calcification. Such factors include, but are not limited to, serum levels of phosphorus, calcium, and calcium.times.phosphorus product, parathyroid hormone (PTH), low-density lipoprotein cholesterol (LDL), high-density lipoprotein cholesterol (HDL), triglycerides, and creatinine. Methods of measuring these factors are well known in the art. Other methods of assessing vascular calcification include assessing factors of bone formation. Such factors include bone formation markers such as bone-specific alkaline phosphatase (BSAP), osteocalcin (OC), carboxyterminal propeptide of type I collagen (PICP), and aminoterminal propeptide of type I collagen (PINP); serum bone resorption markers such as cross-linked C-telopeptide of type I collagen (ICTP), tartrate-resistant acid phosphatase, TRACP and TRAP5B, N-telopeptide of collagen cross-links (NTx), and C-telopeptide of collagen cross-links (CTx); and urine bone resorption markers, such as hydroxyproline, free and total pyridinolines (Pyd), free and total deoxypyridinolines (Dpd), N-telopeptide of collagen cross-links (NTx), and C-telopeptide of collagen cross-links (CTx).

3. Methods of Treatment

In some aspects, the invention provides a method of inhibiting, decreasing or preventing vascular calcification in an individual. The method comprises administering to the individual a therapeutically effective amount of the disclosed TNAP inhibitor. In one aspect, administration of the disclosed compound retards or reverses the formation, growth or deposition of extracellular matrix hydroxyapatite crystal deposits. In another aspect, administration of the compound of the invention prevents the formation, growth or deposition of extracellular matrix hydroxyapatite crystal deposits.

Methods disclosed herein can be used to prevent or treat atherosclerotic calcification and medial calcification and other conditions characterized by vascular calcification. In one aspect, vascular calcification can be associated with chronic renal insufficiency or end-stage renal disease. In another aspect, vascular calcification can be associated with pre- or post-dialysis or uremia. In a further aspect, vascular calcification can be associated with diabetes mellitus I or II. In yet another aspect, vascular calcification can be associated with a cardiovascular disorder.

In some aspects, administration of an effective amount of a TNAP inhibitor can reduce serum PTH without causing aortic calcification. In another aspect, administration of a TNAP inhibitor can reduce serum creatinine level or can prevent increase of serum creatinine level. In another aspect, administration of a TNAP inhibitor can attenuates parathyroid (PT) hyperplasia.

TNAP inhibitors can be administered alone or in combination with other drugs for treating vascular calcification, such as vitamin D sterols and/or RENAGEL®. Vitamin D sterols can include calcitriol, alfacalcidol, doxercalciferol, maxacalcitol or paricalcitol.

The TNAP inhibitors disclosed herein can be used with calcimimetics, vitamins and their analogs, antibiotics, lanthanum carbonate, lipid-lowering agents, such as LIPITOR®, anti-hypertensives, anti-inflammatory agents (steroidal and non-steroidal), inhibitors of pro-inflammatory cytokine (ENBREL®, KINERET®), and cardiovascular agents.

In some aspects, the compositions disclosed herein can be administered before, concurrently, or after administration of calcimimetics, vitamin D sterols and/or RENAGEL®. The dosage regimen for treating a disease condition with the combination therapy disclosed herein is selected in accordance with a variety of factors, including the type, age, weight, sex and medical condition of the patient, the severity of the disease, the route of administration, and the particular compound employed, and thus can vary widely.

In some aspects, TNAP inhibitors can be administered before or after administration of vitamin D sterolsIn some aspects, TNAP inhibitors can be co-administered with vitamin D sterols. The methods disclosed herein can be practiced to attenuate the mineralizing effect of calcitriol on vascular tissue. In some aspects, the methods disclosed herein can be used to reverse the effect of calcitriol of increasing the serum levels of calcium, phosphorus and calcium-phosphorus product (CaxP) thereby preventing or inhibiting vascular calcification. In some aspects, the methods disclosed herein can be used to stabilize or decrease serum creatinine levels. In some aspects, in addition to creatinine level increase due to a disease, a further increase in creatinine level can be due to treatment with vitamin D sterols such as calcitriol.

In addition, TNAP inhibitors can be administered in conjunction with surgical and non-surgical treatments. In one aspect, the methods disclosed herein can be practiced in injunction with dialysis.

4. Administration

The disclosed compounds and compositions can be administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

It is further understood and herein contemplated that the disclosed inhibitors can be administered in conjunction with balloons tipped catheters and/or stents. It is contemplated herein that the stents, catheters, and/or balloons can be linked with the TNAP inhitors or administered concurrently with the use. By "linking" or "linked" is meant any method of placing a TNAP inhibitor onto the stent such as soaking, coating, infusing, or any known chemical methods. Also contemplated herein are time released methods of attaching a TNAP inhibitor to a balloon or stent. Thus, for example disclosed herein are stents used for treatment of a vascualar condition, wherein the stent has been coated with a TNAP inhibitor. Also disclosed herein are methods of provides a method of inhibiting, decreasing or preventing vascular calcification comprising administering to an individual a stent, balloon, and/or cathator that has been linked to a TNAP inhibitor. Thus, for example disclosed herein are methods of inhibiting, decreasing or preventing vascular calcification comprising administering to a subject a vascular stent coated with a TNAP inhibitor.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The exact amount of the compositions required can vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. Thus, effective dosages and schedules for administering the compositions can be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage can vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products.

For example, a typical daily dosage of the TNAP inhibitor used alone might range from about 1 μg/kg to up to 100 mg/kg of body weight or more per day, depending on the factors mentioned above.

The compositions disclosed herein may be administered prophylactically to patients or subjects who are at risk for or who have been newly diagnosed with vascular calcification.

The disclosed compositions and methods can also be used for example as tools to isolate and test new drug candidates for a variety of vascular calcification.related diseases.

Disclosed herein are methods for inhibiting tissue-nonspecific alkaline phosphatases comprising, contacting in vivo, in vitro, or ex vivo a tissue-nonspecific alkaline phosphatase with an effective amount of one or more compounds disclosed herein.

Further disclosed herein are methods for preventing or controlling one or more cardiovascular diseases comprising, administering to a person in need of treatment an effective amount of one or more compounds disclosed herein.

Yet further disclosed is the use of a disclosed compound for making a medicament useful for treating one or more cardiovascular diseases. Cardiovascular diseases include vascular calcification and arterial calcification, Still further disclosed is the use of a disclosed compound in a medicament.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

C. Definitions

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents.

As used in the specification and the appended claims, the singular forms "a," "an" and "the" include plural referents unless the context clearly dictates otherwise. Thus, for example, reference to "a compound," "a formulation," or "a drug" includes mixtures of two or more such compounds, formulations, drugs, and the like.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

As used herein, the terms "Optional" or "optionally" means that the subsequently described event or circumstance may or may not occur, and that the description includes instances where said event or circumstance occurs and instances where it does not.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. In particular, "administration" can be by bolus injection with a syringe and needle, or by infusion through a catheter in place within a vessel. A vessel can be an artery or a vein. Administration can be continuous or intermittent. In one aspect, systemic delivery of payloads by transdermal administration into subcutaneous circulation using the solid lipid nanoparticles disclosed herein can be accomplished in combination with a chemical penetration enhancer.

As used herein, the term "subject" means any target of administration. The subject can be an animal, for example, a mammal. In a further example, the subject can be a human. In an even further example, the subject can be a cell.

As used herein, the term "prodrug," means an agent that is not necessarily biologically active when administered but, upon administration can be converted to a bioactive agent through metabolism or some other mechanism. A prodrug can comprise any covalently bonded substance that can release the active parent drug or other formulas or compounds disclosed herein in vivo when such pro-drug is administered to a subject.

Throughout the description and claims of this specification, the word "comprise" and variations of the word, such as "comprising" and "comprises," means "including but not limited to," and is not intended to exclude, for example, other additives, components, integers or steps.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

The following chemical hierarchy is used throughout the specification to describe and enable the scope of the present invention and to particularly point out and distinctly claim the units which comprise the compounds of the present invention, however, unless otherwise specifically defined, the terms used herein are the same as those of the artisan of ordinary skill. The term "hydrocarbyl" stands for any carbon atom-based unit (organic molecule), said units optionally containing one or more organic functional group, including inorganic atom comprising salts, inter alia, carboxylate salts, quaternary ammonium salts. Within the broad meaning of the term "hydrocarbyl" are the classes "acyclic hydrocarbyl" and "cyclic hydrocarbyl" which terms are used to divide hydrocarbyl units into cyclic and non-cyclic classes.

As it relates to the following definitions, "cyclic hydrocarbyl" units may comprise only carbon atoms in the ring (carbocyclic and aryl rings) or may comprise one or more heteroatoms in the ring (heterocyclic and heteroaryl). For "carbocyclic" rings the lowest number of carbon atoms in a ring are 3 carbon atoms; cyclopropyl. For "aryl" rings the lowest number of carbon atoms in a ring are 6 carbon atoms; phenyl. For "heterocyclic" rings the lowest number of carbon atoms in a ring is 1 carbon atom; diazirinyl. Ethylene oxide comprises 2 carbon atoms and is a $C_2$ heterocycle. For "heteroaryl" rings the lowest number of carbon atoms in a ring is 1 carbon atom; 1,2,3,4-tetrazolyl. The following is a non-limiting description of the terms "acyclic hydrocarbyl" and "cyclic hydrocarbyl" as used herein.

A. Substituted and Unsubstituted Acyclic Hydrocarbyl:
   For the purposes of the present invention the term "substituted and unsubstituted acyclic hydrocarbyl" encompasses 3 categories of units:
1) linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 3-carboxypropyl ($C_3$), and the like.
2) linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.
3) linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3- ynyl ($C_7$), 6-hydroxy-6-methylhept-3-yn-2-yl ($C_8$), 5-hydroxy-5-ethylhept-3-ynyl ($C_9$), and the like.

B. Substituted and Unsubstituted Cyclic Hydrocarbyl:

For the purposes of the present invention the term "substituted and unsubstituted cyclic hydrocarbyl" encompasses 5 categories of units:

1) The term "carbocyclic" is defined herein as "encompassing rings comprising from 3 to 20 carbon atoms, wherein the atoms which comprise said rings are limited to carbon atoms, and further each ring can be independently substituted with one or more moieties capable of replacing one or more hydrogen atoms." The following are non-limiting examples of "substituted and unsubstituted carbocyclic rings" which encompass the following categories of units:
   i) carbocyclic rings having a single substituted or unsubstituted hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), decalinyl ($C_{10}$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$).
   ii) carbocyclic rings having two or more substituted or unsubstituted fused hydrocarbon rings, non-limiting examples of which include, octahydropentalenyl ($C_8$), octahydro-1H-indenyl ($C_9$), 3a4,5,6,7,7a-hexahydro-3H-inden-4-yl ($C_9$), decahydroazulenyl ($C_{10}$).
   iii) carbocyclic rings which are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3- dimethyl[2.2.1]heptan-2-yl, bicyclo[2.2.2]octanyl, and bicyclo[3.3.3]undecanyl.

2) The term "aryl" is defined herein as "units encompassing at least one phenyl or naphthyl ring and wherein there are no heteroaryl or heterocyclic rings fused to the phenyl or naphthyl ring and further each ring can be independently substituted with one or more moieties capable of replacing one or more hydrogen atoms." The following are non-limiting examples of "substituted and unsubstituted aryl rings" which encompass the following categories of units:
   i) $C_6$ or $C_{10}$ substituted or unsubstituted aryl rings; phenyl and naphthyl rings whether substituted or unsubstituted, non-limiting examples of which include, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyano-naphthylen-1-yl ($C_{10}$).
   ii) $C_6$ or $C_{10}$ aryl rings fused with 1 or 2 saturated rings non-limiting examples of which include, bicyclo[4.2.0] octa-1,3,5-trienyl ($C_8$), and indanyl ($C_9$).

3) The terms "heterocyclic" and/or "heterocycle" are defined herein as "units comprising one or more rings having from 3 to 20 atoms wherein at least one atom in at least one ring is a heteroatom chosen from nitrogen (N), oxygen (O), or sulfur (S), or mixtures of N, O, and S, and wherein further the ring which comprises the heteroatom is also not an aromatic ring." The following are non-limiting examples of "substituted and unsubstituted heterocyclic rings" which encompass the following categories of units:
   i) heterocyclic units having a single ring containing one or more heteroatoms, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), isoxazolyl ($C_3$), thiazolidinyl ($C_3$), isothiazolyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_8$), and 1,2,3,4-tetrahydro-quinoline ($C_9$).
   ii) heterocyclic units having 2 or more rings one of which is a heterocyclic ring, non-limiting examples of which include hexahydro-1H-pyrrolizinyl ($C_7$), 3a,4,5,6,7,7a-hexahydro-1H-benzo[d]imidazolyl ($C_7$), 3a,4,5,6,7,7a-hexahydro-1H-indolyl($C_8$), 1,2,3,4-tetrahydroquinolinyl ($C_9$), and decahydro-1H-cycloocta[b]pyrrolyl ($C_{10}$).

4) The term "heteroaryl" is defined herein as "encompassing one or more rings comprising from 5 to 20 atoms wherein at least one atom in at least one ring is a heteroatom chosen from nitrogen (N), oxygen (O), or sulfur (S), or mixtures of N, O, and S, and wherein further at least one of the rings which comprises a heteroatom is an aromatic ring." The following are non-limiting examples of "substituted and unsubstituted heterocyclic rings" which encompass the following categories of units:
   i) heteroaryl rings containing a single ring, non-limiting examples of which include, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), furanyl ($C_4$), thiopheneyl ($C_4$), pyrimidinyl ($C_4$), 2-phenylpyrimidinyl ($C_4$), pyridinyl ($C_5$), 3-methylpyridinyl ($C_5$), and 4-dimethylaminopyridinyl ($C_5$)
   ii) heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-d]pyrimidinyl ($C_6$), pyrido[2,3-d]pyrimidinyl ($C_7$), 2-phenylbenzo[d]thiazolyl ($C_7$), 1H-indolyl ($C_8$), 4,5,6,7-tetrahydro-1-H-indolyl ($C_8$), quinoxalinyl ($C_8$), 5-methylquinoxalinyl ($C_8$), quinazolinyl ($C_8$), quinolinyl ($C_9$), 8-hydroxy-quinolinyl ($C_9$), and isoquinolinyl ($C_9$).

5) $C_1$-$C_6$ tethered cyclic hydrocarbyl units (whether carbocyclic units, $C_6$ or $C_{10}$ aryl units, heterocyclic units, or heteroaryl units) which connected to another moiety, unit, or core of the molecule by way of a $C_1$-$C_6$ alkylene unit. Non-limiting examples of tethered cyclic hydrocarbyl units include benzyl $C_1$-($C_6$) having the formula:

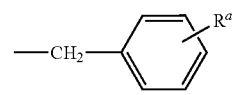

wherein $R^a$ is optionally one or more independently chosen substitutions for hydrogen. Further examples include other aryl units, inter alia, (2-hydroxyphenyl)hexyl $C_6$-($C_6$); naphthalen-2-ylmethyl $C_1$-($C_{10}$), 4-fluorobenzyl $C_1$-($C_6$), 2-(3-hydroxy-phenyl)ethyl $C_2$-($C_6$), as well as substituted and unsubstituted $C_3$-$C_{10}$ alkylenecarbocyclic units, for example, cyclopropylmethyl $C_1$-($C_3$), cyclopentylethyl $C_2$-($C_5$), cyclohexylmethyl $C_1$-($C_6$). Included within this category are substituted and unsub stituted $C_1$-$C_{10}$ alkylene-heteroaryl units, for example a 2-picolyl $C_1$-($C_6$) unit having the formula:

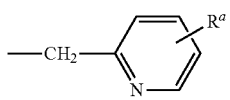

wherein $R^a$ is the same as defined above. In addition, $C_1$-$C_{12}$ tethered cyclic hydrocarbyl units include $C_1$-$C_{10}$ alkyleneheterocyclic units and alkylene-heteroaryl units, non-limiting examples of which include, aziridinylmethyl $C_1$-($C_2$) and oxazol-2-ylmethyl $C_1$-($C_3$).

For the purposes of the present invention carbocyclic rings are from $C_3$ to $C_{20}$; aryl rings are $C_6$ or $C_{10}$; heterocyclic rings are from $C_1$ to $C_9$; and heteroaryl rings are from $C_1$ to $C_9$.

For the purposes of the present invention, and to provide consistency in defining the present invention, fused ring units, as well as spirocyclic rings, bicyclic rings and the like, which comprise a single heteroatom will be characterized and referred to herein as being encompassed by the cyclic family corresponding to the heteroatom containing ring, although the artisan may have alternative characterizations. For example, 1,2,3,4-tetrahydroquinoline having the formula:

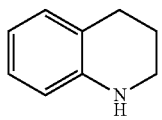

is, for the purposes of the present invention, considered a heterocyclic unit. 6,7-Dihydro-5H-cyclopentapyrimidine having the formula:

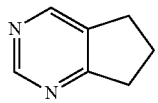

is, for the purposes of the present invention, considered a heteroaryl unit. When a fused ring unit contains heteroatoms in both a saturated ring (heterocyclic ring) and an aryl ring (heteroaryl ring), the aryl ring will predominate and determine the type of category to which the ring is assigned herein for the purposes of describing the invention. For example, 1,2,3,4-tetrahydro-[1,8]naphthyridine having the formula:

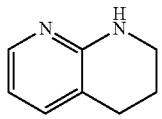

is, for the purposes of the present invention, considered a heteroaryl unit.

The term "substituted" is used throughout the specification. The term "substituted" is applied to the units described herein as "substituted unit or moiety is a hydrocarbyl unit or moiety, whether acyclic or cyclic, which has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms may be replaced. For example, 4-hydroxyphenyl is a "substituted aromatic carbocyclic ring (aryl ring)", (N,N-dimethyl-5-amino)octanyl is a "substituted $C_8$ linear alkyl unit, 3-guanidinopropyl is a "substituted $C_3$ linear alkyl unit," and 2-carboxypyridinyl is a "substituted heteroaryl unit."

The following are non-limiting examples of units which can substitute for hydrogen atoms on a carbocyclic, aryl, heterocyclic, or heteroaryl unit:
i) $C_1$-$C_4$ linear or branched alkyl; for example, methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$);
ii) —$OR^{30}$; for example, —OH, —$OCH_3$, —$OCH_2CH_3$, —$OCH_2CH_2CH_3$;
iii) —$C(O)R^{30}$; for example, —$COCH_3$, —$COCH_2CH_3$, —$COCH_2CH_2CH_3$;
iv) —$C(O)OR^{30}$; for example, —$CO_2CH_3$, —$CO_2CH_2CH_3$, —$CO_2CH_2CH_2CH_3$;
v) —$C(O)N(R^{30})_2$; for example, —$CONH_2$, —$CONHCH_3$, —$CON(CH_3)_2$;
vi) —$N(R^{30})_2$; for example, —$NH_2$, —$NHCH_3$, —$N(CH_3)_2$, —$NH(CH_2CH_3)$;
vii) halogen: —F, —Cl, —Br, and —I;
viii) —$CH_mX_n$; wherein X is halogen, m is from 0 to 2, m+n=3; for example, —$CH_2F$, —$CHF_2$, —$CF_3$, —$CCl_3$, or —$CBr_3$; and
ix) —$SO_2R^{30}$; for example, —$SO_2H$; —$SO_2CH_3$; —$SO_2C_6H_5$
wherein each $R^{30}$ is independently hydrogen, substituted or unsubstituted $C_1$-$C_4$ linear, branched, or cyclic alkyl; or two $R^{30}$ units can be taken together to form a ring comprising 3-7 atoms. Substituents suitable for replacement of a hydrogen atom are further defined herein below.

The compounds disclosed herein include all salt forms, for example, salts of both basic groups, inter alia, amines, as well as salts of acidic groups, inter alia, carboxylic acids. The following are non-limiting examples of anions that can form salts with basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: sodium, lithium, potassium, calcium, magnesium, bismuth, and the like.

D. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1 i. Expression and Preparation of Test Enzymes

Expression plasmids containing a secreted epitope-tagged TNAP, PLAP and IAP were transfected into COS-1 cells for transient expression using a standard electroporation method. Medium was replaced to Opti-MEM 24 hours later, and the serum free media containing secreted proteins were collected 60 hours after electroporation. Conditioned medium was dialyzed against TBS containing 1 mM $MgCl_2$ ad 20 µM $ZnCl_2$ (to remove phosphate) and filtrated with a 2 µm cellulose acetate filter.

ii. High Throughput Screening a. TNAP Colorimetric Assay

A TNAP stock solution was diluted 120-fold and about 12 ul of diluted TNAP solution were dispensed into 96 well microtiter plates with half area bottom (Costar, Corning, N.Y.) by an auto dispenser (Matrix, Hudson, N.H.). A robotic liquid handler, Biomek™ FX (Beckman Coulter, Fullerton, Calif.) dispensed about 2.5 µl of each compound (dissolved in 10% DMSO) from the library plates. Plates were incubated at room temperature for at least one hour to allow TNAP to interact with each compound prior to addition of about 10.5 µl substrate solution (1.19 mM pNPP). After about 30 minutes of incubation, $A_{405\,nm}$ was measured with a microtiter plate reader, Analyst™ HT (Molecular Devices, Sunnyvale, Calif.). Both the enzyme (TNAP) and substrate (pNPP) solution were made in diethanolamine (DEA) buffers; the final reaction contains 1M DEA-HCl buffer, pH about 9.8, containing about 1 mM $MgCl_2$ and about 20 µM $ZnCl_2$. The concentration of TNAP and pNPP (final about 0.5 mM) were adjusted to obtain $A_{405\,nm}$~0.4, while maintaining good sensitivity to the known inhibitors levamisole and phosphate, used as positive controls. $K_m$ obtained with a 1/120 dilution of TNAP and a fixed incubation period of about 30 minutes, was 0.58+0.081 mM.

b. TNAP Luminescence Assay

Compound aliquots (4 uL @ 100 uM in 10% DMSO) were added with about 8 uL of TNAP working solution, prepared by 800-fold dilution of TNAP in 2.5-fold assay buffer (250 mM DEA, pH 9.8, 2.5 mM $MgCl_2$, 0.05 mM $ZnCl_2$). CDP-star substrate solution (about 8 uL of 125 uM in water) was added to each well. The final concentration of CDP-star was equal its Km value determined in the assay buffer. Plates (white 384-well small volume Greiner 784075) were incubated at room temperature for about 0.5 hour and luminescence signal was measured using an EnVision plate reader (PerkinElmer). Levamisole (1 mM final concentration) or 2% DMSO were utilized as positive and negative controls, respectively. Dose-response confirmation was performed under similar conditions using 10-point 2-fold serial dilution of compounds.

iii. Enzyme Kinetic Experiments

To determine the inhibition selectivity for inhibitor candidates, human TNAP, PLAP or IAP were added to microtiter plates followed by addition of the substrate pNPP (0.5 mM) and activity was measured in 1 M DEA-HCl buffer, pH 9.8 or in 1 M Tris-HCl buffer, pH 7.5, containing 1 mM $MgCl_2$ and 20 µM $ZnCl_2$, in the presence of potential inhibitors (0-30 µM). TNAP, PLAP and IAP activities were adjusted to an approximate $\Delta A_{405\,nm}$, equivalent to 1, measured after 30 min. Residual AP activity in the presence of inhibitors was expressed as percentage of the control activity. To investigate the mechanism of inhibition, double reciprocal plots of enzyme activity (expressed as $mA_{405\,nm}\,min^{-1}$) vs. substrate concentration were constructed, in the presence of various concentrations of added inhibitors (0-30 µM). The y-axis intercepts of the 1/v vs. 1/[S] plots, were then plotted vs. [I] to graphically extract $K_i$ values as the x-intercept in this plot. The numerical values from y- and x-intrecepts were derived via linear regression analysis, using software Prism 3.02 (GraphPad Software, CA). These analyses were performed, using pNPP as a substrate in 1 M DEA-HCl buffer, pH 9.8, as well as in 1 M Tris-HCl buffer, pH 7.5, to determine $K_i$ at optimal and physiological pH respectively. Inhibitors were further tested and sorted based on their kinetic properties at pH 7.4 using $PP_i$, the relevant natural substrate of TNAP. In this part of the study, pyrophosphate sodium salt (99% ACS reagent, Sigma-Aldrich, St Louis, Mo.) was used as a substrate. Amounts of released phosphate were measured using the Biomol Green Reagent (Biomol Research Laboratories, Inc., Plymouth Meeting, Pa.). Finally, to document the potency of selected inhibitors in physiological media, TNAP inhibition by compound 5804079 (0-30 µM) was studied at pH 7.4, during catalysis of 0.1 mM pNPP, in the presence of increasing concentrations of $Na_2HPO_4$ (0-10 mM) and pyrophosphate (0-40 mM).

Compound docking was performed using the Flexx program, part of the Sybyl package from Trios, Inc. Formal charges were used for protein and compound atoms. Heteroatoms (phosphate, zincs and magnesium) were considered as part of the pocket while docking.

iv. Tissue Preparation and Morphological Analysis

Whole-mount skeletal preparations were prepared by removal of skin and viscera of mice followed by a 1-week immersion in 100% ethanol, followed by 100% acetone. Samples were then transferred to a 100% ethanol solution containing 0.01% Alizarin Red S, 0.015% Alcian Blue 8GX, and 0.5% acetic acid for three weeks. Samples were then destained with 1% (vol/vol) KOH/50% glycerol solution. Cleared samples were stored in 100% glycerol.

v. Isolation and Culture of Primary VSMCs

Vascular SMCs were isolated from explants using a collagenase digestion method and the smooth muscle phenotype was confirmed by RT-PCR analysis for smooth muscle α-actin. One mouse aorta provided on average, $5\times10^5$ cells. These cells were cultured (in triplicate) at a density of $3\times10^4$ cells/$cm^2$ using α-MEM supplemented with β-glycerophosphate (10 mM) and 50 µg/ml ascorbic acid for 3 weeks. To quantify calcium deposited in these cultures, either the o-cresolphthalein complexone method[31] or the standard Alizarin Red method was used.

vi. $PP_i$ Hydrolysis by Whole Aortas Ex Vivo

Rats were sacrificed and aortas perfused with Hanks salt solution to remove blood. The aortas were then removed and, after the adventitia was dissected away, were cut into rings approximately 2 mm in length. Four rings were placed in 1 ml of DMEM without serum containing the compounds to be tested. After 90 min at 37° C., sodium $PP_i$ (final concentration 1 µM) and [$^{32}$P]$P_i$ (final concentration 1 µCurie/ml) were added and 6 samples were removed over 4 hours. $P_i$ was separated from $PP_i$ by adding 800 µl of 0.028 M ammonium molybdate in 0.75 M $H_2SO_4$ to the samples and extracting with 1600 µl of isobutanol and petroleum ether (4:1). $^{32}$P was counted in the organic phase by Cerenkov radiation. Hydrolysis of $PP_i$ was linear over 4 hours and the rate was determined by linear regression.

Table 1 indicates the inhibition constants for (6S)-6-phenyl-2,3,5,6-tetrahydro-imidazo[2,1-b][1,3]thiazole (levamisole) as compared to compounds disclosed herein.

TABLE 1

| Compounds | $K_i$ (μM) @ pH 9.8 | $K_i$ (μM) @ pH 7.5 |
|---|---|---|
| 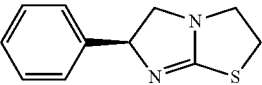<br>(6S)-6-phenyl-2,3,5,6-tetrahydroimidazo[2,1-b][1,3]thiazole | 21.4 ± 0.001 | 17.0 ± 0.02 |
| 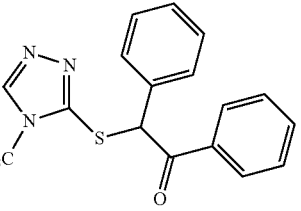<br>$N^2$-phenyl-6-[(5-phenyl-1H-1,2,4-triazol-3-ylthio)methyl]-1,3,5-triazine-2,4-diamine | 5.6 ± 1.6 | 6.4 ± 1.6 |
| 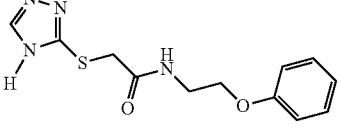<br>2-((5-(2-methoxyphenyl)-4H-1,2,4-triazol-3-ylthio)methyl)pyridine | 5.6 ± 0.7 | 33 ± 5.8 |
| 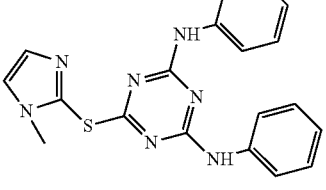<br>6-(1-methyl-1H-imidazol-2-ylthio)-$N^2,N^4$-diphenyl-1,3,5-triazine-2,4-diamine | 6.5 ± 1.4 | 2.8 ± 0.4 |

Table 2 shows the reduction in the rate of hydrolysis of $PP_i$ in aortic rat rings by the compounds shown in Table 1.

TABLE 2

| Compounds | $PP_i$ hydrolysis (nmol/g/min) | % Inhibition |
|---|---|---|
| Control | 0.32 ± 0.032 | 0.0 |
| Vehicle | 0.312 ± 0.017 | 2.5 |
| 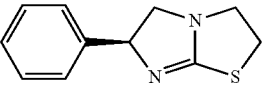<br>(6S)-6-phenyl-2,3,5,6-tetrahydroimidazo[2,1-b][1,3]thiazole | 0.252 ± 0.047 | 21.2 |

TABLE 2-continued

| Compounds | $PP_i$ hydrolysis (nmol/g/min) | % Inhibition |
|---|---|---|
| 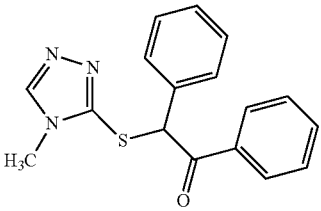<br>$N^2$-phenyl-6-[(5-phenyl-1H-1,2,4-triazol-3-ylthio)methyl]-1,3,5-triazine-2,4-diamine | 0.269 ± 0.032 | 15.9 |
| 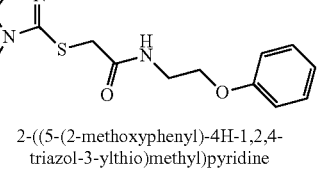<br>2-((5-(2-methoxyphenyl)-4H-1,2,4-triazol-3-ylthio)methyl)pyridine | 0.249 ± 0.046 | 22.2 |
| 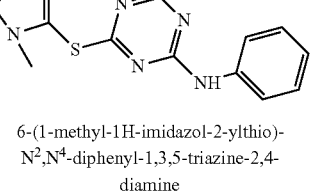<br>6-(1-methyl-1H-imidazol-2-ylthio)-$N^2,N^4$-diphenyl-1,3,5-triazine-2,4-diamine | 0.192 ± 0.041 | 39.9 |

2. Example 2

Figure 1B:
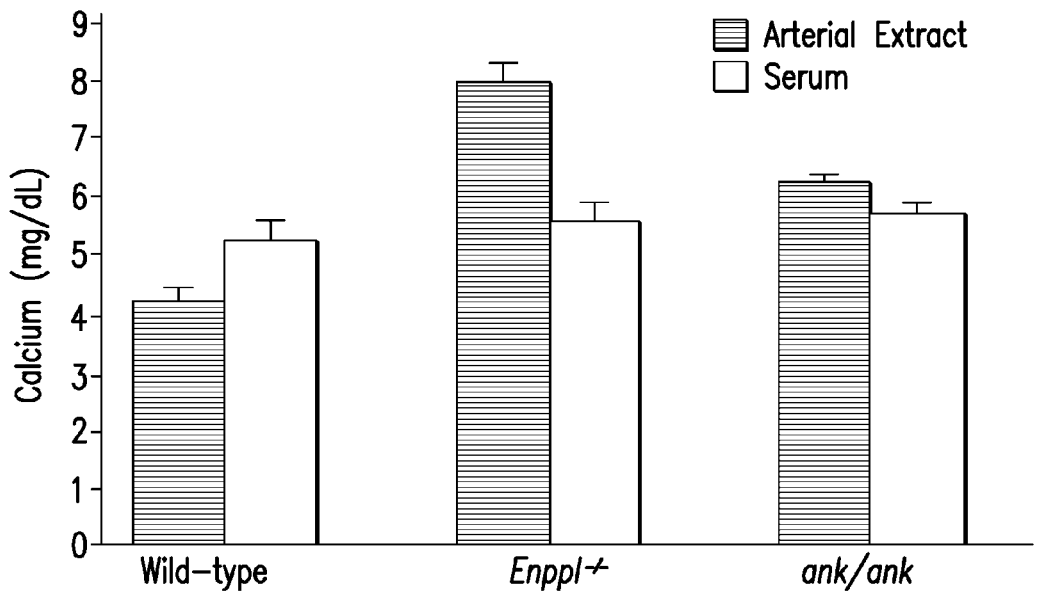
FIG. 1B shows the quantification of calcium deposits in Enpp1$^{-/-}$, ank/ank, and control (Wt) mice demonstrates that Enpp1$^{-/-}$ mice have a higher degree of calcification than ank/ank mice.

Deficiency of NPP1 function can lead to idiopathic infantile arterial calcification in humans and mice Linkage of a dysfunction of Enpp1 to arterial calcification suggests that abnormal $PP_i$ metabolism can be an important regulatory factor for vascular smooth muscle cell (V SMC) differentiation and function. Given the coordinated function of NPP1 and ANK in establishing extracellular $PP_i$ concentrations and the similarity of the calcification abnormalities found in the $Enpp1_{-/-}$ and the ank/ank mutant mice it can be expected that the similarities would also extend to the arterial calcification sites. The extent and severity of aortic calcification was compared in $Enpp1^{-/-}$ and ank/ank mice. Whole mount preparations of heart and aorta were dissected and stained with Alizarin Red to visualize calcium deposition. The presence of multiple foci of aortic calcification could be seen (FIG. 1A) in $Enpp1^{-/-}$ mice while none are evident in control mice. Similar qualitative results were obtained for the ank/ank mice. The amount of calcium deposited in WT, $Enpp1^{-/-}$ and ank/ank aortas was quantified. Using mice at 3 months of age, the data obtained indicate a higher degree of calcification in $Enpp1^{-/-}$ and ank/ank compared to wt control animals. More calcification was also found in $Enpp1^{-/-}$ mice than in ank/ank mice (FIG. 1B), a result that agrees with the more severe calcification phenotype that was observed in the $Enpp1^{-/-}$ mice.

Figure 1C:
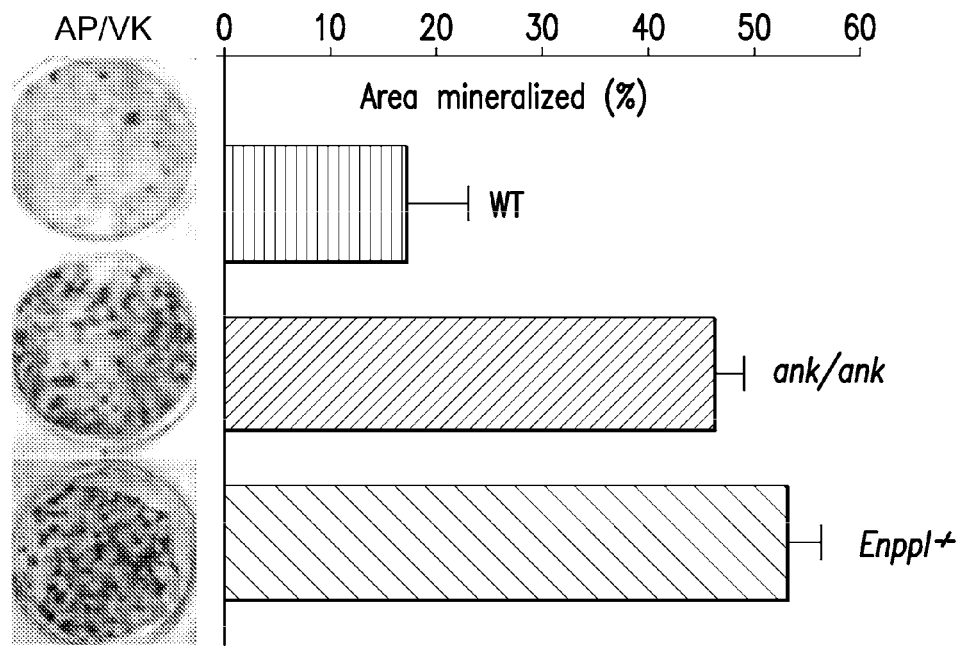
FIG. 1C shows that VSMCs from Enpp1$^{-/-}$ and ank/ank mice display a TNAP activity level higher than the control (Wt) activity level. VSMCs from Enpp1$^{-/-}$ and ank/ank mice also produce significantly more mineral than control (Wt) cells.

Given that arterial calcification can be more severe in $Enpp1^{-/-}$ than in ank/ank mice $Enpp1^{-/-}$ mice were chosen for subsequent in vitro experiments to determine the putative involvement of TNAP in the ectopic calcification process. Using a collagenase digestion method, VSMCs were isolated and identified them by immunofluorescence and RT-PCR detection of SMC α-actin. Hence, a population of cells was obtained in which, on average, 89% stained positive for SMC α-actin. Using these VSMC cultures, it was determined that WT VSMCs express TNAP activity. It was also determined that WT VSMCs, when cultured in the presence of β-glycerophosphate and ascorbic acid, can lay down mineral in a manner similar (e.g., kinetically similar) to that of osteoblast cultures. It was further determined that VSMCs from Enpp1$^{-/-}$ and ank/ank mutant mice display a higher TNAP activity than WT cells, and that they produce significantly more mineral than WT cells (FIG. 1C). While not wishing to be bound by theory, it was surmised that by inhibiting the up-regulated pyrophosphatase TNAP activity, it would be possible to restore the normal ePP$_i$ levels, which in turn would contribute to suppressing HA deposition in the vasculature. To do this efficiently, the screening of comprehensive chemical libraries was carried out in order to identify and characterize novel lead compounds that could enable the development of potent drug-like inhibitor of TNAP's physiological pyrophosphatase function.

An assay to screen chemical libraries containing 53,280 compounds was optimized. These included: a) the Spectrum Collection (MicroSource, Gaylordsville, Conn., U.S.A.) containing 2000 compounds (25 plates, 80 compounds/plate); about half of the collection contains known bioactive agents, permitting the evaluation of hundreds of marketed drugs and biochemical standards; the other half of the collection includes pure natural products and their derivatives; b) the LOPAC$^{1280}$ Collection (Sigma Aldrich, St. Louis, Mo., U.S.A.), containing 1280 pharmacologically active compounds; this library contains effector molecules for major target classes and all of the compounds in this collection are available for powder re-supply from SIGMA; and c) the Chembridge DIVERSet Collection (from Chembridge, San Diego, Calif., U.S.A) that contains 50,000 diverse, pre-designed compounds (625 plates, 80 compounds per plate); this collection was selected via a an approach based on 3D pharmacophore analysis to cover a broad spectrum of biologically relevant pharmacophore diversity space.

Figure 2:
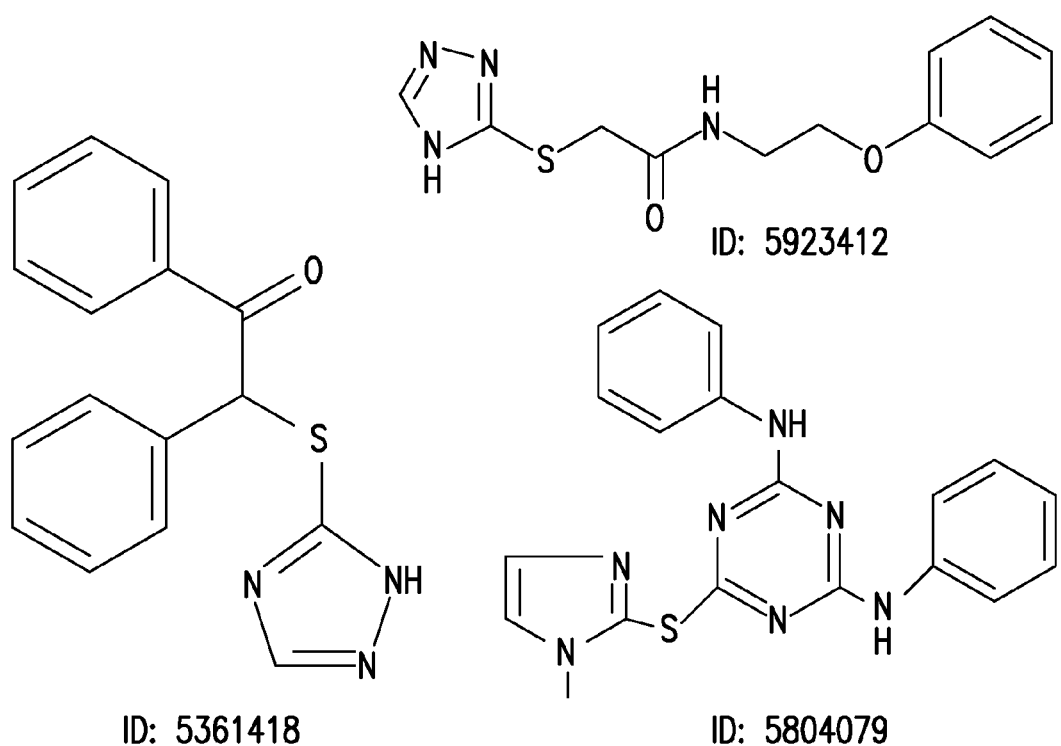
FIG. 2 shows the structures of three novel and effective TNAP inhibitors are defined. The nitrogen content of these three compounds ranges from 3-7 N atoms per inhibitor.

Screening the chemical libraries was based on a 96-well plate assay using 0.5 mM pNPP as substrate. Concentrations of about 30 µM of the uncompetitive inhibitor levamisole and about 300 µM of the competitive inhibitor P$_i$ were used in each individual assay plate as positive controls. The concentration of the chemical library compounds in the reaction mixture was about 10 µM. After each daily run of assay, manual testing of any compound which had shown more than 20% inhibition was carried out. A total of eleven hits with reproducible inhibition were re-tested and at least four compounds were identified as effective TNAP inhibitors: one was levamisole, a well-known weak AP inhibitor, contained within the 2000 Spectrum Collection of known drugs and presently used as a positive control during our screening. The other three corresponded to structures shown in FIG. 2. The physicochemical property of these compounds is summarized in Table I. Although not a limiting aspect of the compounds disclosed herein, all three compounds conform to Lipinski's rule of 5, i.e., have a molecular weight of less that 500; have less than five H-bond donors; have less than five H-bond acceptors; have less than 10 rotational bonds and an octanol/water repartition coefficient (LogP)<5. Their nitrogen content ranges from 3-7 N atoms per inhibitor (FIG. 2).

Figure 3:
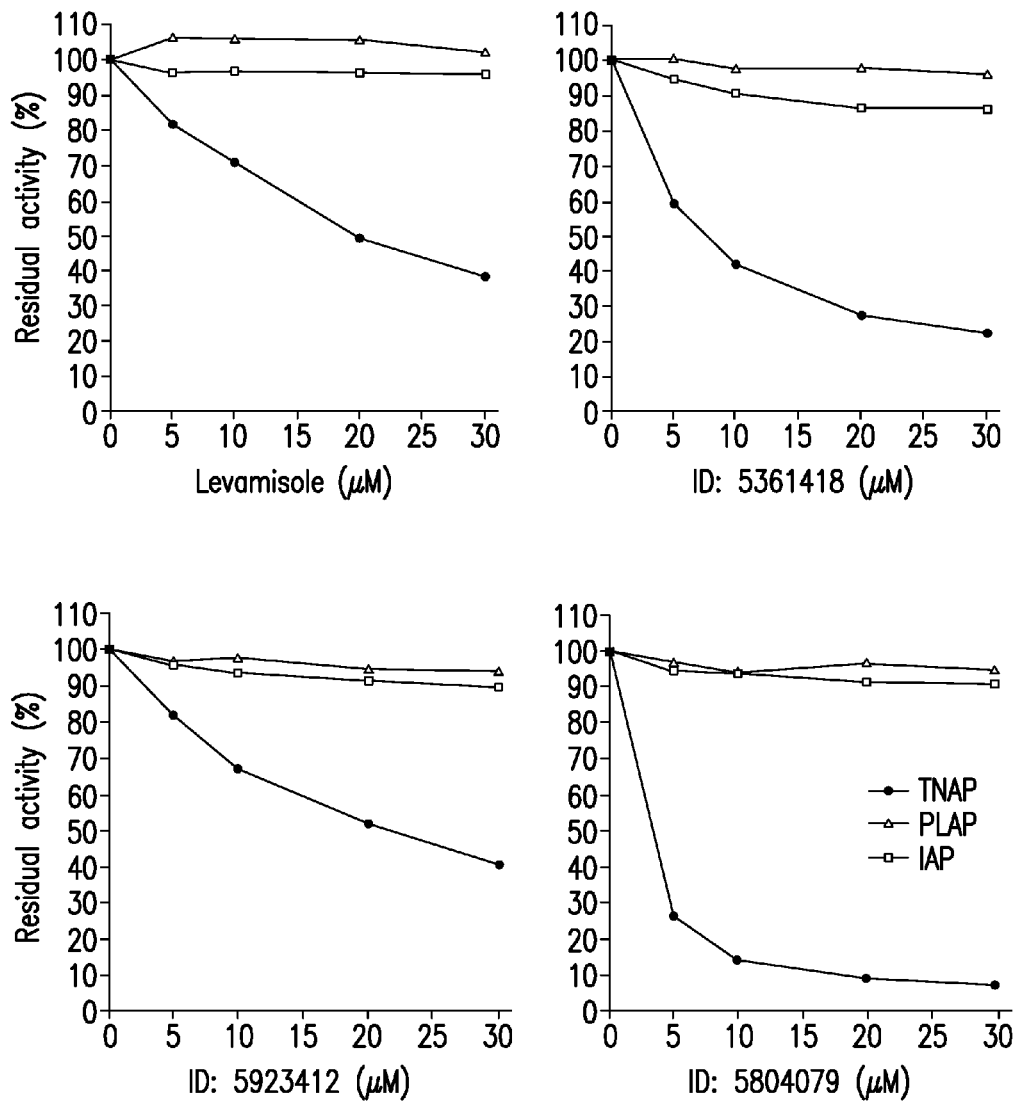
FIG. 3 shows that increasing concentrations of inhibitors (0-30 μM) reduce TNAP, PLAP, and IAP activity levels.
Figure 4A:
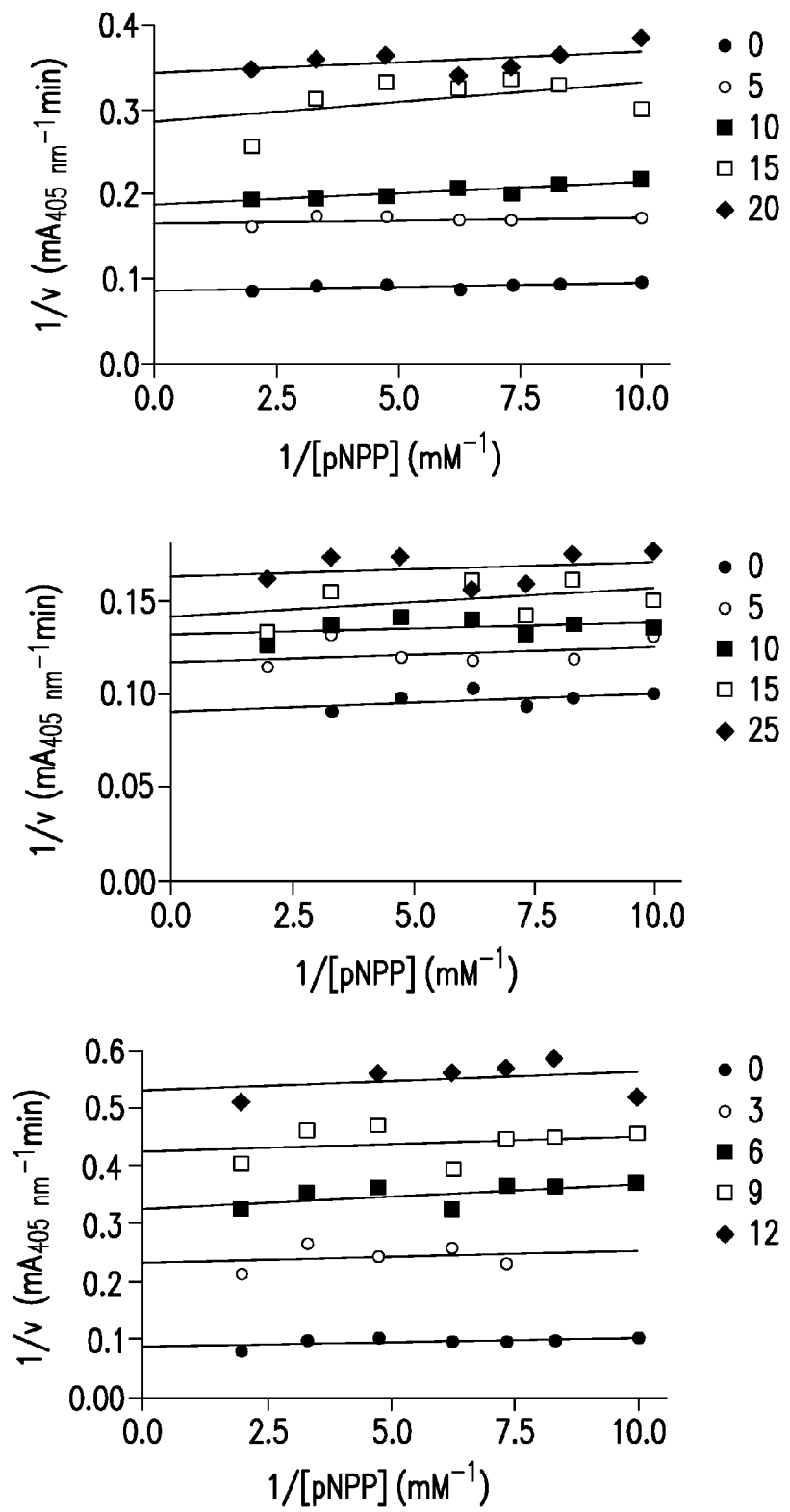
FIG. 4A shows the double reciprocal plots of 1/v v. 1/[S] for various concentrations show parallel lines for the three novel inhibitors. These plots indicate that each TNAP inhibitor acts in an uncompetitive manner.
Figure 4B:
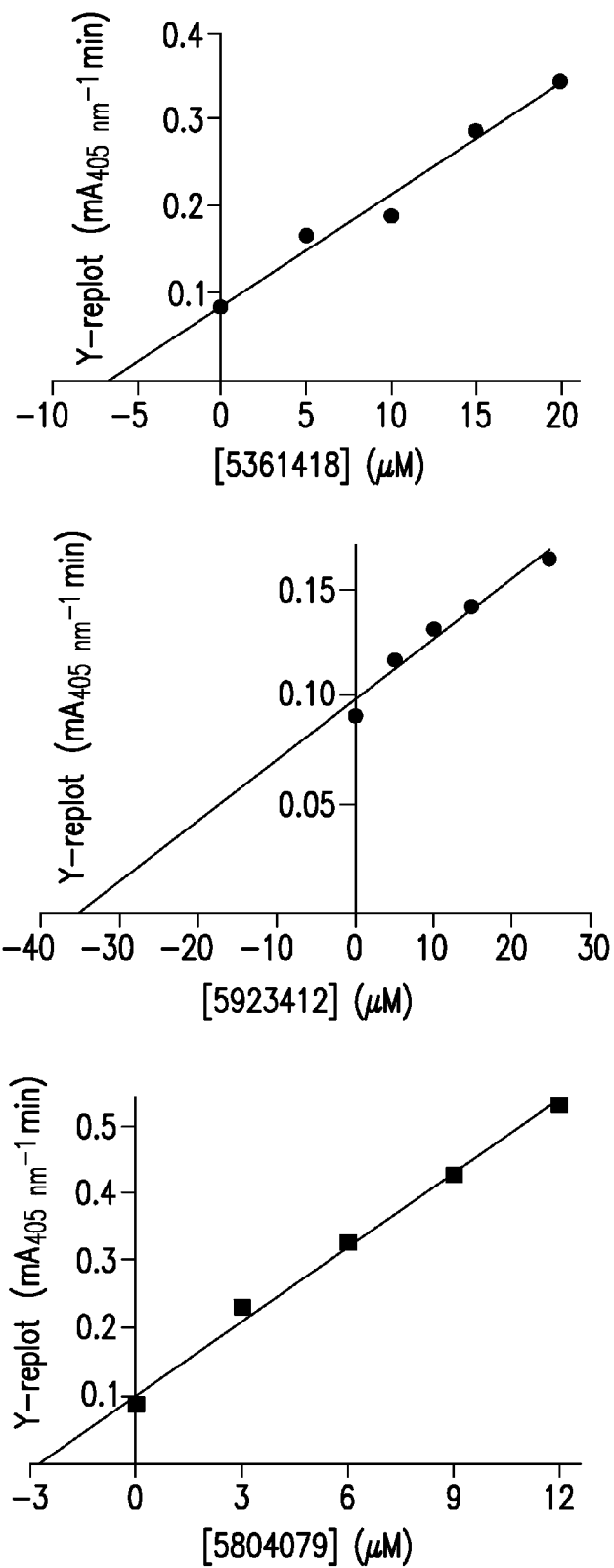
FIG. 4B shows the secondary re-plots of the y-intercepts determine the K$_i$ and therefore determine the potency for each novel inhibitor.

None of the three identified TNAP inhibitors appeared to inhibit, either at pH 9.8 or at physiological pH, other relevant human APs, such as PLAP or IAP that share 50% and 52% sequence identity with TNAP. FIG. 3 shows the inhibition of TNAP, PLAP and IAP for increasing concentrations (0-30 µM) of the inhibitors, at physiological pH. Furthermore, none of the inhibitors had any effect on PHOSPHO1, a novel phosphatase proposed to be involved in the initiation of MV-mediated calcification. The double reciprocal plots of 1/v vs. 1/[S], for various inhibitor concentrations, showed parallel lines for all 3 inhibitors, indicating that each TNAP inhibitor can act in an uncompetitive manner, both at pH 9.8 and at physiological pH (FIG. 4A). Secondary re-plots of the y-intercepts (FIG. 4B) afforded which can describing the potency for each inhibitor. Compound 5804079 had the lowest K$_i$ value at physiological pH, i.e., can be about 10-fold more potent than the frequently used inhibitor levamisole (Table II). In addition, it can be more potent at pH 7.5 than at pH 9.8.

Figure 5A:
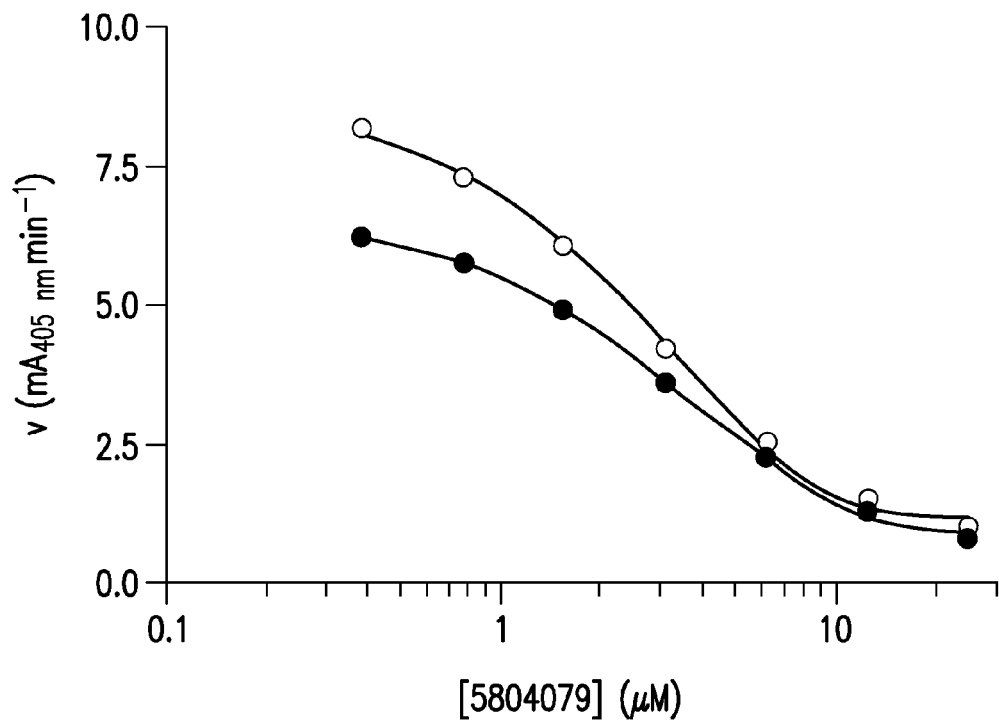
FIG. 5A shows that at concentrations largely exceeding those for inhibitor or substrate, the presence of the competitive inhibitor P$_i$ does not affect the potency of compound 5804079.
Figure 5B:
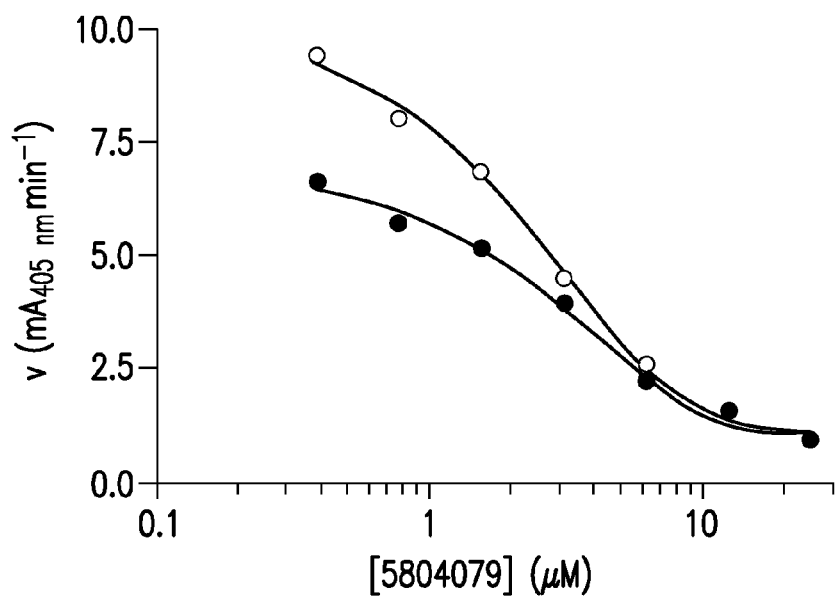
FIG. 5B shows that at high concentrations of PP$_i$ does not affect the degree of inhibition by compound 5804079.

FIG. 5A shows that the potency of compound 5804079 is not affected by the presence of the competitive inhibitor P$_i$, at concentrations largely exceeding those for inhibitor or substrate. FIG. 5B shows that also the degree of inhibition by compound 5804079 is not affected by high concentrations of PP$_i$, in agreement with the uncompetitive nature of this inhibitor, which does not have to compete with P$_i$ or PP$_i$ for binding to the enzyme, but only binds to the phospho-enzyme complex, once it is formed.

Figure 6A:
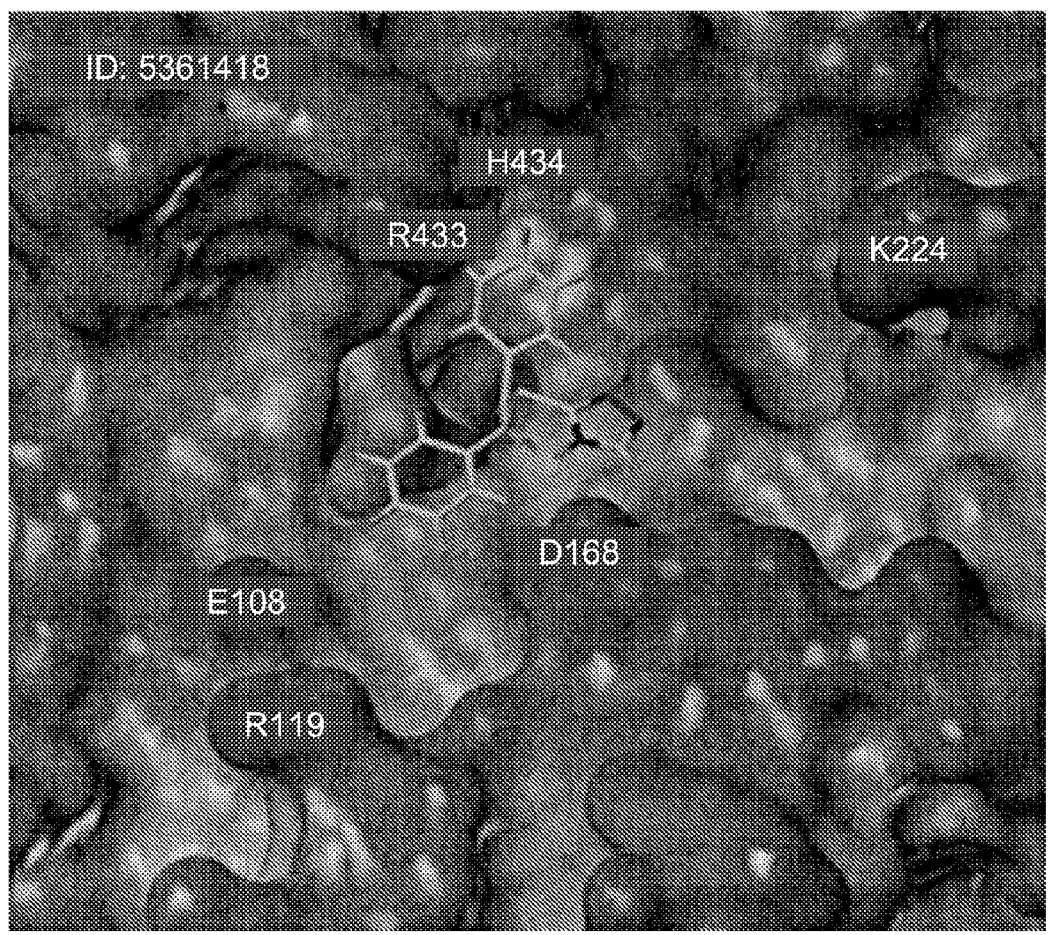
FIG. 6 shows that two of the three novel compounds predominantly dock into the R433/H434 region of the binding site.
Figure 6B:
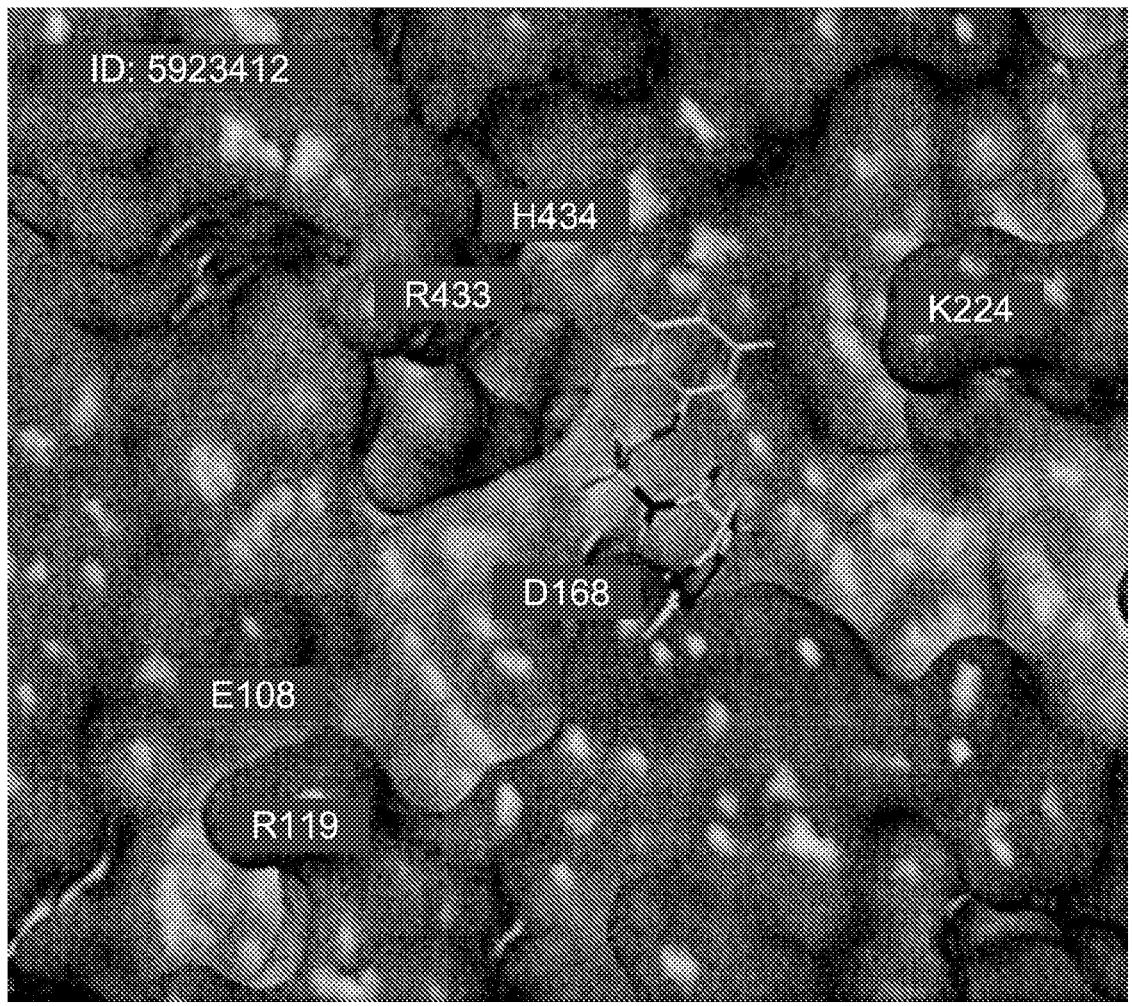
Figure 6C:
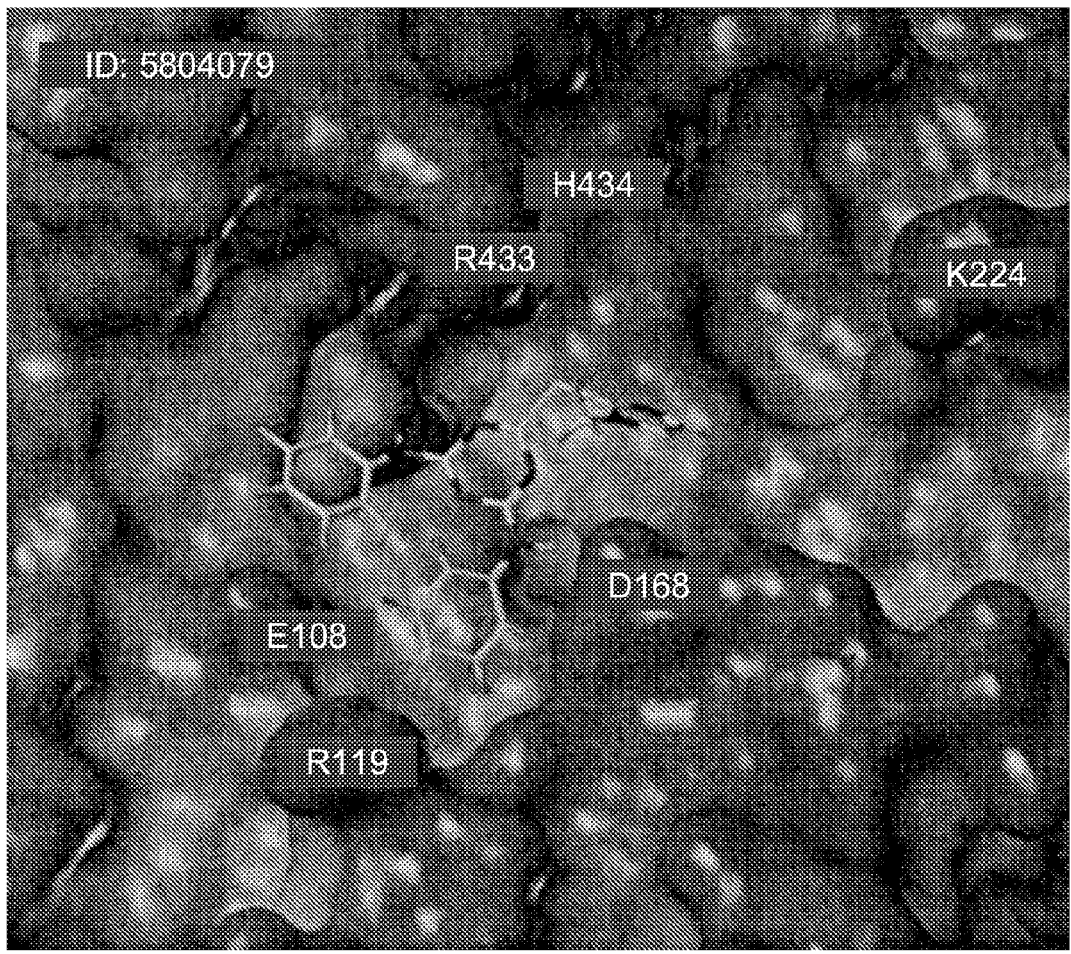

The likely positioning of three well-known inhibitors of AP activity, i.e., L-homorginine, levamisole and theophylline, in the active site of TNAP has recently been documented. Two distinct areas in the TNAP active site able to accommodate inhibitors were found; the first, comprising residues R433 and H434, accommodates hydrophobic ringed structures such as levamisole and theophylline, while the second, comprising residues E108/G109 can accommodate more hydrophilic extended inhibitors such a L-homoarginine. It was found that two of the three newly identified compounds predominantly dock into the R433/H434 region of the binding site (FIG. 6). Compound 5804079 appears to dock in a manner that spans both binding areas. This may in part explain the low K$_i$ for this compound, as well as its slightly better performance at pH 7.5.

Figure 7:
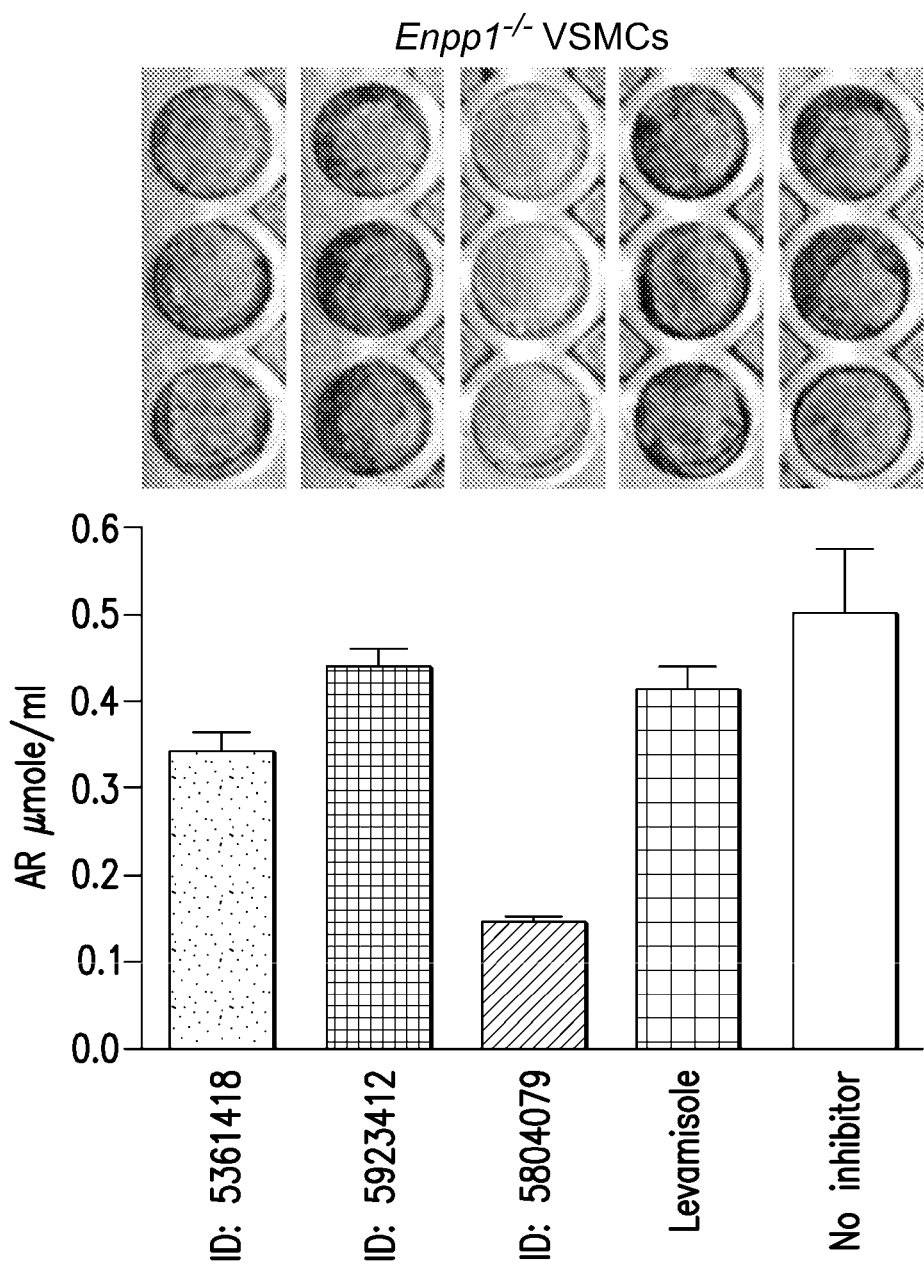
FIG. 7 shows that all four compounds inhibit, to some degree, mineralization in VSMCs.

To validate the inhibitory potential of all three inhibitors on in vitro calcification, the ability of all three compounds, using levamisole as control, to inhibit up-regulated TNAP activity in Enpp1$^{-/-}$ VSMCs was tested. All four compounds at least partially inhibited mineralization in this culture system (FIG. 7), with compound 5804079 being the most inhibitory, compatible with TNAP neutralization in this more physiological setting.

Furthermore, to measure the degree of pyrophosphatase inhibition by the new TNAP inhibitors, an ex vivo organ culture system in whole aortas was used. For this analysis, rat rather than mouse aortas were selected, as they are larger and easier to dissect. This analysis also showed that compound 5804079 was most effective in suppressing endogenous pyrophosphatase activity at the site of vascular calcification (Table III) at the maximal concentration of 30 µM (chosen for all these highly aromatic inhibitors to avoid solubility problems).

E. References

Ali S Y, Sajdera S W, Anderson H C 1970 Isolation and characterization of calcifying matrix vesicles from epiphyseal cartilage. Proc Natl Acad Sci USA 67:1513-1520.

Bhopale G M, Bhatnagar B S 1984 Serum protein profile of mice during infection of Ancylostoma caninum and after the administration of tetramisole and levamisole. J Hyg Epi Micro Immuno 128:455-459.

Bucay N, Sarosi I, Dunstan C R, Morony S, Tarpley J, Capparelli C, Scully S, Tan H L, Xu W, Lacey D L, Boyle W J, Simonet W S 1998 osteoprotegerin-deficient mice develop early onset osteoporosis and arterial calcification. Genes Dev 12:1260-1268.

Detrano R C, Doherty T M, Davies M J, Stary H C 2000 Predicting coronary events with coronary calcium: pathophysiologic and clinical problems. Curr Probl Cardiol 25:374-402.

Di Mauro, S., Manes, T., Hessle, H., Kozlenkov, A., Pizauro, J. M., Hoylaerts, M. F. and Milián, J. L. Kinetic characterization of hypophosphatasia mutations with physiological substrates. J. Bone & Min. Res. 17: 1383-1391 (2002).

Doherty T M, Uzui H, Fitzpatrick L A, Tripathi P V, Dunstan C R, Asotra K, Rajavashisth T B 2002 Rationale for the role of osteoclast-like cells in arterial calcification. Faseb J 16:577-582.

Eisenberg E, Shklar G 1977 Levamisole and hamster pouch carcinogenesis. Oral Sur Oral Med Oral Path 43:562-571.

Harmey D, Hessle L, Narisawa S, Johnson K, Terkeltaub R, Milián J L 2004 Concerted regulation of inorganic pyrophosphate and osteopontin by Akp2, Enpp1 and Ank. An integrated model of the pathogenesis of mineralization disorders. Am J Pathol 164: 1199-1209.

Harmey D, Johnson K A, Zelken J, Camacho N P, Hoylaerts M F, Noda M, Terkeltaub R, Milián J L 2006 Elevated osteopontin levels contribute to the hypophosphatasia phenotype in Akp2−/− mice. J Bone Min Res 21: 1377-1386.

Hessle L, Johnson K A, Anderson H C, Narisawa S, Sali A, Goding J W, Terkeltaub R, Milián J L 2002 Tissue-nonspecific alkaline phosphatase and plasma cell membrane glycoprotein-1 are central antagonistic regulators of bone mineralization. Proc Natl Acad Sci USA 99:9445-9449.

Ho A M, Johnson M D, Kingsley D M 2000 Role of the mouse ank gene in control of tissue calcification and arthritis. Science 289:265-270.

Hoylaerts M F, Ding L, Narisawa S, Van Kerckhoven S, Milián J L 2006 Mammalian alkaline phosphatase catalysis requires active site structure stabilization via the N-terminal amino acid microenvironment. Biochemistry 45:9756-9766.

Hoylaerts M F, Manes T, Milián J L 1992 Molecular mechanism of uncompetitive inhibition of human placental and germ cell alkaline phosphatase. Biochem J 286:23-30.

Hsu H H, Anderson H C 1978 Calcification of isolated matrix vesicles and reconstituted vesicles from fetal bovine cartilage. Proc Natl Acad Sci USA 75:3805-3808.

Hsu H H, Camacho N P 1999 Isolation of calcifiable versicles from human atherosclerotic aortas. Atherosclerosis 143: 353-362.

Hsu H H T, Camacho N P, Sun F, Tawik, Ossama, Aono H 2000 Isolation of calcifiable vesicles from aortas of rabbits fed with high cholesterol diets. Atherosclerosis 153:337-348.

Hui M, Li S Q, Holmyard D, Cheng P 1997 Stable transfection of nonosteogenic cell lines with tissue nonspecific alkaline phosphatase enhances mineral deposition both in the presence and absence of beta-glycerophosphate: possible role for alkaline phosphatase in pathological mineralization. Calcified Tissue International 60:467-72.

Hui M, Tenenbaum H C 1998 New face of an old enzyme: alkaline phosphatase may contribute to human tissue aging by inducing tissue hardening and calcification. Anatomical Record 253:91-94.

Johnson K, Goding J, Van Etten D, Sali A, Hu S I, Farley D, Krug H, Hessle L, Milián J L, Terkeltaub R 2003 Linked deficiencies in extracellular PP(i) and osteopontin mediate pathologic calcification associated with defective PC-1 and ANK expression. J Bone Min Res 18:994-1004.

Johnson K, Polewski M, van Etten D, Terkeltaub R 2005 Chondrogenesis mediated by PPi depletion promotes spontaneous aortic calcification in NPP1−/− mice. Arterioscler Thromb Vasc Biol 25:686-691.

Johnson K A, Hessle L, Wennberg C, Mauro S, Narisawa S, Goding J, Sano K, Milián J L, Terkeltaub R 2000 Tissue-nonspecific alkaline phosphatase (TNAP) and plasma cell membrane glycoprotein-1 (PC-1) act as selective and mutual antagonists of mineralizing activity by murine osteoblasts. Am J Phys Regulatory and Integrative Physiology 279: R1365-1377.

Kim K M 1976 Calcification of matrix vesicles in human aortic valve and aortic media. Fed Proc 35:156-162.

Kozlenkov A, Hoylaerts M F, Ny T, Le Du M H, Milián J L 2004 Residues determining the binding specificity of uncompetitive inhibitors to tissue-nonspecific alkaline phosphatase. J Bone Min Res 19:1862-1872.

Lomashvili K, Cobbs S, Hennigar R, Hardcastle K, O'Neill W C 2004 Phosphate-induced vascular calcification: role of pyrophosphate and osteopontin. J. Am. Soc. Nephrol. 15: 1392-1401.

Mathieu P, Voisine P, Pepin A, Shetty R, Savard N, Dagenais F 2005 Calcification of human valve interstitial cells is dependent on alkaline phosphatase activity. J Heart Valve Disease 14:353-357.

Milián J L 2006 Mammalian alkaline phosphatases. From biology to applications in medicine and biotechnology. Wiley-VCH Verlag GmbH & Co, Weinheim, Germany pp. 1-322.

Myers D L, Harmon K J, Lindner V, Liaw L 2003 Alterations of arterial physiology in osteopontin-null mice. Arterioscler Thromb Vasc Biol 23:1021-1028.

Okawa A, Nakamura I, Goto S, Moriya H, Nakamura Y, Ikegawa S 1998 Mutation in Npps in a mouse model of ossification of the posterior longitudinal ligament of the spine. Nat Genet. 19:271-273.

Powe T A, Powers R D 1985 Periorchitis after tetramisole treatment in bulls implaned with Setaria labiatopapillos. J Am Vet Med Ass 186: 588-589.

Roberts S, Narisawa S, Harmey D, Millán J, Farquharson C 2007 Functional involvement of PHOSPHO1 in matrix vesicle-mediated skeletal calcification. J Bone Min Res In press.

Rutsch F, Ruf N, Vaingankar S, Toliat M R, Suk A, Hohne W, Schauer G, Lehmann M, Roscioli T, Schnabel D, Epplen J T, Knisely A, Superti-Furga A, McGill J, Filippone M, Sinaiko A R, Vallance H, Hinrichs B, Smith W, Ferre M, Terkeltaub R, Nurnberg P 2003 Mutations in ENPP1 are associated with 'idiopathic' infantile arterial calcification. Nat Genet. 34:379-381.

Rutsch F, Vaingankar S, Johnson K, Goldfine I, Maddux B, Schauerte P, Kalhoff H, Sano K, Boisvert W A, Superti-Furga A, Terkeltaub R 2001 PC-1 nucleoside triphosphate pyrophosphohydrolase deficiency in idiopathic infantile arterial calcification. Am J Pathol 158:543-554.

Sali A, Favaloro J M, Terkeltaub R, Goding J W: Germline deletion of the nucleoside triphosphate pyrophosphohydrolase (NTPPPH) plasma cell membrane glycoprotein-1 (PC-1) produces abnormal calcification of periarticular tissues. In Vanduffel L, Lemmems R (ed.) Ecto-ATPases and related ectoenzymes. Shaker Publishing B V, 1999, pp 267-282.

Shioi A, Katagi M, Okuno Y, Mori K, Jono S, Koyama H, Nishizawa Y 2002 Induction of bone-type alkaline phosphatase in human vascular smooth muscle cells: roles of tumor necrosis factor-alpha and oncostatin M derived from macrophages. Circ Res 91:9-16.

Shioi A, Nishizawa Y, Jono S, Koyama H, Hosoi M, Morii H 1995 Beta-glycerophosphate accelerates calcification in cultured bovine vascular smooth muscle cells. Arterioscler Thromb Vasc Biol 15:2003-2009.

Speer M Y, McKee M D, Guldberg R E, Liaw L, Yang H Y, Tung E, Karsenty G, Giachelli C M 2002 Inactivation of the osteopontin gene enhances vascular calcification of matrix Gla protein-deficient mice: evidence for osteopontin as an inducible inhibitor of vascular calcification in vivo. J Exp Med 196:1047-1055.

Steitz S A, Speer M Y, Curing a G, Yang H Y, Haynes P, Aebersold R, Schinke T, Karsenty G, Giachelli C M 2001 Smooth muscle cell phenotypic transition associated with calcification: upregulation of Cbfal and downregulation of smooth muscle lineage markers. Circ Res 89:1147-1154.

Steitz S A, Speer M Y, McKee M D, Liaw L, Almeida M, Yang H, Giachelli C M 2002 Osteopontin inhibits mineral deposition and promotes regression of ectopic calcification. Am J Pathol 161:2035-2046.

Taal B G, van Tinteren H, Zoetmulder F A, NACCP group 2001 Adjuvant 5FU plus levamisole in colonic or rectal cancer; improved survival in stage II and III. Brit J Cancer 85:1437-1443.

Tanimura A, McGregor D H, Anderson H C 1986 Calcification in atherosclerosis. I. Human studies. J Exp Pathol 2:261-273.

Tanimura A, McGregor D H, Anderson H C 1986 Calcification in atherosclerosis. II. Animal studies. J Exp Pathol 2:275-297.

Tintut Y, Alfonso Z, Saini T, Radcliff K, Watson K, Bostrom K, Demer L L 2003 Multilineage potential of cells from the artery wall. Circulation 108:2505-2510.

Tintut Y, Patel J, Territo M, Saini T, Parhami F, Demer L L 2002 Monocyte/macrophage regulation of vascular calcification. Circulation 105:650-655.

von der Recke P, Hansen M A, Hassager C 1999 The association between low bone mass at the menopause and cardiovascular mortality. Am J Med 106:273-278.

Wada T, McKee M D, Steitz S, Giachelli C M 1999 Calcification of vascular smooth muscle cell cultures: inhibition by osteopontin. Circ Res 84:166-178.

Watson K E, Bostrom K, Ravindranath R, Lam T, Norton B, Demer L L 1994 TGF-beta 1 and 25-hydroxycholesterol stimulate osteoblast-like vascular cells to calcify. J Clin Invest 93:2106-2113.

Wennberg C, Hessle L, Lundberg P, Mauro S, Narisawa S, Lerner U H, Milián J L 2000 Functional characterization of osteoblasts and osteoclasts from alkaline phosphatase knockout mice. J Bone Min Res 15:1879-1888.

Witte R S, Cnaan A, Mansour E G, Barylak E, Harris J E, Schutt A J 2001 Comparison of 5-fluorouracil alone, 5-fluorouracil with levamisole, and 5-fluorouracil with hepatic irradiation in the treatment of patients with residual, nonmeasurable, intra-abdominal metastasis after undergoing resection for colorectal carcinoma. Cancer 91:1020-1028.

What is claimed is:

1. A method of treating vascular calcification in a subject, comprising administering one or more compounds having one of the following formula:

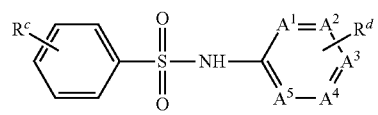

Formula I

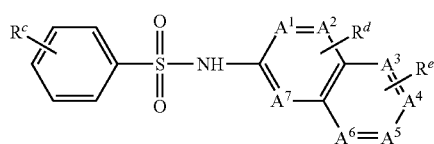

Formula II wherein $A^2$ represents —N—;
wherein $A^1$, $A^3$, $A^4$, $A^5$, $A^6$, and $A^7$ each independently represent —C—;
wherein $R^c$ is in the ortho position;
wherein the $R^c$, $R^d$, and $R^e$ substitutions are each independently chosen from:
  i) halogen;
  ii) hydroxyl;
  iii) $C_1$-$C_4$ alkyl;
  iv) $C_1$-$C_4$ alkoxy;
  v) substituted or unsubstituted heterocyclic;
  vi) substituted or unsubstituted heteroaryl;
  vii) substituted or unsubstituted aryl;
  viii) amino;
  ix) mono-$C_1$-$C_4$ alkylamino;
  x) di-$C_1$-$C_4$ alkylamino;
  xi) nitro; and
  xii) cyano,
  wherein the compound is not 2,5-dimethoxy-N-(quinolin-3-yl)benzene-sulfonamide;
  2-methoxy-5-methyl-N-(pyridine-3-yl)benzene-sulfonamide;
  2-ethoxy-5-methyl-N-(pyridine-3-yl)benzenesulfonamide; or
  N-[(3-1H-1,2,4,-triazol-3-ylthio)-4-hydroxyphenyl]-2,5-dimethoxybenzenesulfonamide; and
  wherein the compounds are TNAP inhibitors.

2. The method of claim 1, wherein the compound has one of the following formula:

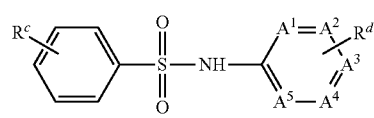

Formula I

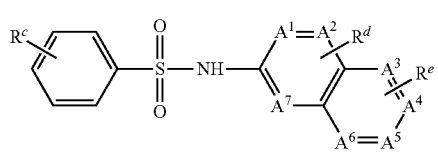

Formula II wherein further the substitutions are each independently chosen from:
  i) halogen;
  ii) hydroxyl;
  iii) $C_1$-$C_4$ alkyl;
  iv) $C_1$-$C_4$ alkoxy;
  v) substituted or unsubstituted heterocyclic;
  vi) substituted or unsubstituted heteroaryl;
  vii) substituted or unsubstituted aryl;

viii) amino;
ix) mono-$C_1$-$C_4$ alkylamino;
x) di-$C_1$-$C_4$ alkylamino;
xi) nitro; and
xii) cyano.

3. The method of claim 2, wherein further the substitutions are each independently chosen from:
i) halogen;
ii) hydroxyl;
iii) $C_1$-$C_4$ alkyl;
iv) $C_1$-$C_4$ alkoxy;
v) substituted or unsubstituted heterocyclic;
vi) substituted or unsubstituted heteroaryl;
vii) substituted or unsubstituted aryl; and
viii) nitro.

4. The method of claim 3, wherein further the substitutions are each independently chosen from:
i) hydroxyl;
ii) halogen;
iii) $C_1$-$C_4$ alkyl;
iv) $C_1$-$C_4$ alkoxy;
v) substituted or unsubstituted heteroaryl; and
vi) nitro.

5. A method of inhibiting or reducing the severity or incidence of vascular calcification in a subject, comprising administering one or more compounds having one of the following formula:

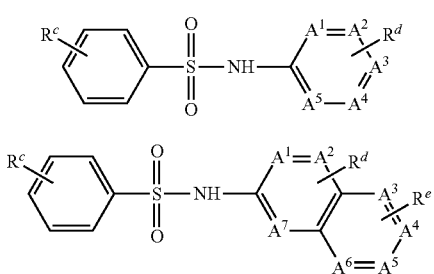

Formula I

Formula II wherein $A^2$ represents —N—;
wherein $A^1$, $A^3$, $A^4$, $A^5$, $A^6$, and $A^7$ each independently represent —C—;
wherein $R^c$ is in the ortho position;
wherein the $R^b$, $R^c$, $R^d$, and $R^e$ substitutions are each independently chosen from:
i) halogen;
ii) hydroxyl;
iii) $C_1$-$C_4$ alkyl;
iv) $C_1$-$C_4$ alkoxy;
v) substituted or unsubstituted heterocyclic;
vi) substituted or unsubstituted heteroaryl;
vii) substituted or unsubstituted aryl;
viii) amino;
ix) mono-$C_1$-$C_4$ alkylamino;
x) di-$C_1$-$C_4$ alkylamino;
xi) nitro; and
xii) cyano,
wherein the compound is not 2,5-dimethoxy-N-(quinolin-3-yl)benzene-sulfonamide;
2-methoxy-5-methyl-N-(pyridine-3-yl)benzene-sulfonamide;
2-ethoxy-5-methyl-N-(pyridine-3-yl)benzenesulfonamide; or
N-[(3-1H-1,2,4,-triazol-3-ylthio)-4-hydroxyphenyl]-2,5-dimethoxybenzenesulfonamide; and
wherein the compounds are TNAP inhibitors.

6. The method of claim 5, wherein the compound has one of the following formula:

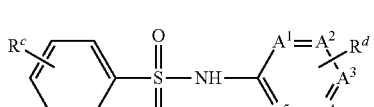

Formula I

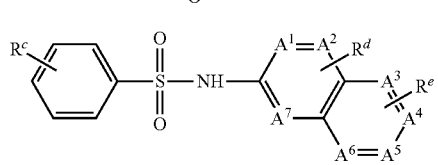

Formula II wherein further the substitutions are each independently chosen from:
i) halogen;
ii) hydroxyl;
iii) $C_1$-$C_4$ alkyl;
iv) $C_1$-$C_4$ alkoxy;
v) substituted or unsubstituted heterocyclic;
vi) substituted or unsubstituted heteroaryl;
vii) substituted or unsubstituted aryl;
viii) amino;
ix) mono-$C_1$-$C_4$ alkylamino;
x) di-$C_1$-$C_4$ alkylamino;
xi) nitro; and
xii) cyano.

7. The method of claim 6, wherein further the substitutions are each independently chosen from:
i) halogen;
ii) hydroxyl;
iii) $C_1$-$C_4$ alkyl;
iv) $C_1$-$C_4$ alkoxy;
v) substituted or unsubstituted heterocyclic;
vi) substituted or unsubstituted heteroaryl;
vii) substituted or unsubstituted aryl; and
viii) nitro.

8. The method of claim 7, wherein further the substitutions are each independently chosen from:
i) hydroxyl;
ii) halogen;
iii) $C_1$-$C_4$ alkyl;
iv) $C_1$-$C_4$ alkoxy;
v) substituted or unsubstituted heteroaryl; and
vi) nitro.

9. The method of claim 1, wherein administration of one or more compounds retards or reverses the formation, growth or deposition of extracellular matrix hydroxyapatite crystal deposits.

10. The method of claim 2, wherein administration of one or more compounds retards or reverses the formation, growth or deposition of extracellular matrix hydroxyapatite crystal deposits.

11. The method of claim 1, wherein $R^c$ is ortho-methoxy.

12. The method of claim 11, wherein the compound has the formula:

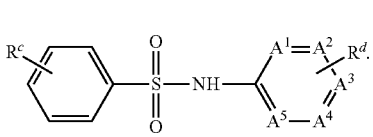

Formula I

13. The method of claim 5, wherein $R^c$ is ortho-methoxy.

14. The method of claim 13, wherein the compound has the formula:
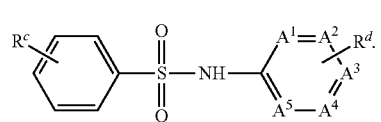
Formula I

UNITED STATES PATENT AND TRADEMARK OFFICE
CERTIFICATE OF CORRECTION

| | |
|---|---|
| PATENT NO. | : 8,686,003 B2 |
| APPLICATION NO. | : 13/313756 |
| DATED | : April 1, 2014 |
| INVENTOR(S) | : Jose Luis Millan and Eduard Sergienko |

It is certified that error appears in the above-identified patent and that said Letters Patent is hereby corrected as shown below:

In the Specification

In Column 1, Lines 19 through 21, please replace:
"Research leading to this invention was funded in part by the National Institutes of Health, grant no. NIH-DE12889. The U.S. Government has certain rights in this invention."

With:
"This invention was made with government support under R01 DE012889, and U54 HG003916 awarded by the National Institutes of Health. The government has certain rights in the invention."

Signed and Sealed this
Seventeenth Day of September, 2024

Katherine Kelly Vidal
*Director of the United States Patent and Trademark Office*